United States Patent
Dubald et al.

(10) Patent No.: US 11,279,944 B2
(45) Date of Patent: Mar. 22, 2022

(54) OF HERBICIDE TOLERANCE TO 4-HYDROXYPHENYLPYRUVATE DIOXYGENASE (HPPD) INHIBITORS BY DOWN-REGULATION OF HPPD EXPRESSION IN SOYBEAN

(71) Applicant: BASF AGRICULTURAL SOLUTIONS SEED US LLC, Florham Park, NJ (US)

(72) Inventors: Manuel Dubald, Research Triangle Park, NC (US); Marc Linka, Duesseldorf (DE)

(73) Assignee: BASF AGRICULTURAL SOLUTIONS SEED US LLC, Florham Park, NJ (US)

( * ) Notice: Subject to any disclaimer, the term of this patent is extended or adjusted under 35 U.S.C. 154(b) by 0 days.

(21) Appl. No.: 16/758,830

(22) PCT Filed: Oct. 18, 2018

(86) PCT No.: PCT/US2018/056464
§ 371 (c)(1),
(2) Date: Apr. 23, 2020

(87) PCT Pub. No.: WO2019/083810
PCT Pub. Date: May 2, 2019

(65) Prior Publication Data
US 2021/0238625 A1  Aug. 5, 2021

Related U.S. Application Data

(60) Provisional application No. 62/576,569, filed on Oct. 24, 2017.

(51) Int. Cl.
*C12N 15/82* (2006.01)
*A01H 6/54* (2018.01)
*C12N 9/02* (2006.01)

(52) U.S. Cl.
CPC ......... *C12N 15/8274* (2013.01); *A01H 6/542* (2018.05); *C12N 9/0069* (2013.01); *C12Y 113/11027* (2013.01)

(58) Field of Classification Search
CPC ............ C12N 15/8274; C12N 15/8218; C12Y 113/11027
See application file for complete search history.

(56) References Cited

U.S. PATENT DOCUMENTS

2013/0097726 A1*  4/2013  Ader ..................... A01N 65/00
                                                          800/278
2017/0166918 A1*  6/2017  Dubald ................ C12N 9/0069

FOREIGN PATENT DOCUMENTS

WO  2014043435 A1  3/2014
WO  2015135881 A1  9/2015
WO  2016128470 A1  8/2016

OTHER PUBLICATIONS

Norris, Susan R., Terrence R. Barrette, and Dean DellaPenna. "Genetic dissection of carotenoid synthesis in *arabidopsis* defines plastoquinone as an essential component of phytoene desaturation." The Plant Cell 7.12 (1995): 2139-2149 (Year: 1995).*
Norris, Susan R., Xiaohua Shen, and Dean Della Penna. "Complementation of the *Arabidopsis* pds1 mutation with the gene encoding p-hydroxyphenylpyruvate dioxygenase." Plant physiology 117.4 (1998): 1317-1323. (Year: 1998).*
Tsegaye, Yoseph, David K. Shintani, and Dean DellaPenna. "Overexpression of the enzyme p-hydroxyphenolpyruvate dioxygenase in *Arabidopsis* and its relation to tocopherol biosynthesis." Plant Physiology and Biochemistry 40.11 (2002): 913-920. (Year: 2002).*
International Search Report and Written Opinion in PCT/US2018/056464 dated Jan. 15, 2019.

* cited by examiner

*Primary Examiner* — Weihua Fan
(74) *Attorney, Agent, or Firm* — Arent Fox LLP

(57) ABSTRACT

A method for conferring tolerance to a 4-hydroxyphenylpyruvate dioxygenase (HPPD) inhibitor herbicide in a plant includes reducing expression of at least one HPPD enzyme in the plant.

14 Claims, 9 Drawing Sheets

Specification includes a Sequence Listing.

```
PfHPPD                        ---------------MADLYENPKG------------------------LNGF  14
Avena_sativa                  --MPPTPAT-ATGAAAAAVTPEHAARS----FPRVVRVNPRSDRFPVLSF  43
Avena_sativa__del             --MPPTPAT-ATGAAAAAVTPEHAARS----FPRVVRVNPRSDRFPVLSF  43
Zea_mays                      ---MGPTPTAAAAGAAVAAASAAEQSAFPLVGHRNFVRFNPRSDRFHTLAF  48
Streptomyces_avermitilis      --MTQTTEHTPDTARQADFFP---------------------VKGM      29
Arabidopsis_thaliana          --NGHQNAAVSENQNHDGSAASSPGFKLVG-PSKFVRENPKSDRFYVKRF  47
Hordeum_vulgare               ---MPPTPTTPAATGAAAAVTPEHAPP------HRKVRPNPRSDRFHTLSF  43
Daucus_carota                 ---MGKK--QSEARILSGNSSNTSPATPKLVG-PNNFVRANPKSDHFAVKRF  46
Mycosphaerella_graminicola    ---MAPGALLVTSQNFPTSPLYDEDGYVPAP-------AALVVGGEVNYRGY  42
Coccicoides_imnitis           ---MAPAADSPTLQPAQPSDLN-------------------QYRGY      24
Axmi309H                      ---------------MADLYENPKG------------------------LMGF  14
Axmi428H                      MNAPLTQSNASUFQTWDNPKG------------------------TDGF  25

PfHPPD                        SFIEFASPTPGTLEPIFEINGFTKVATHRSKN-------VHLYRQGEINL  57
Avena_sativa                  HHVELWCADAASAAGRFSPALGAPLAARSDLSTGNSRHASLLLRSGALAF  93
Avena_sativa__del             HHVELWCADAASAAGRFSPALGAPLAARSDLSTGNSRHASLLLRSGALAF  93
Zea_mays                      HHVELWCADAASAAGRFSPGLGAPLAARSDLSTGNSAHASLLLRSGSLSF  98
Streptomyces_avermitilis      DAVVFAVGNAKQAA-RYSTAFGMQLVAYSRPENGSRETASYVLTNGSARF  78
Arabidopsis_thaliana          HHIEFWCGDATNVARRFSWGLOMRPSARSDLSTONMVHASYLLTSGELRF  97
Hordeum_vulgare               HHVEFWCADAASAAGRFAPALGAPLAARSDLSTGNSRHASQLLRSGSLAF  92
Daucus_carota                 HHIEFWCGDATNTSRRFSWGLGMPLVAKSDLSTGNSVHASYLVRSANLSF  96
Mycosphaerella_graminicola    HHARNWYGNAKQVAQFYITRMCFSFVAHKGLETGSRFFASHVQNNGVRF  92
Coccicoides_imnitis           DHVRNYVGNAKQAATYYVTRMCFSKVAYRGLETGSKAVASKVVRNNSITF  74
Axmi309H                      SFIEFASPTPGTLEPIFEINGFTKVATHRSKN-------VHLYRQGAINL  57
Axmi428H                      RFVEYAARDFVAMGQLFERNGFQAIAKHRRKN-------VTLYRQGEINF  68

PfHPPD                        ILNNEPNS-------------------IASYFAAEHGPSVCGNAFRVK  86
Avena_sativa                  LFTAFYAFPPQBA-ATRAATASIPSFSADAARTFAAAHGLAVRSVSVRVA  142
Avena_sativa__del             LFTAFYAFPPQBA-AT-AATASIPSFSADAARTFAAAHGLAVRSVSVRVA  141
Zea_mays                      LFTAPYAN------GADAATAALPSFSAAAARSFAAEHGLAVRAVALRVA  142
Streptomyces_avermitilis      VLTSVIKPATPRG---HPLA----------DHVAEHGLGVVDLAIEVP  107
Arabidopsis_thaliana          LFTAPVSPSLSAGEIKPTTTASIPSFDHGSCRSFYSSRGLGVRAVAIEVE  147
Hordeum_vulgare               LFTAPYAN------GCDAATASLPSFSADAARRFSADHGIAVRSVALRVA  136
Daucus_carota                 VPTAFVSPSTTT----SSGSAAIPSFSASGFHSFAAKHGLAVRAIALEVA  142
Mycosphaerella_graminicola    VPTSPVRSSARQT---LKAAPLADQARLDRNYDNLDKHGDSVKDVAFSVD  139
Coccicoides_imnitis           ILTSPLRSVEQAS---RFPB----DEALLKEIRAHLERHGDGVKDVAPSVD  118
Axmi309H                      ILNNEPNS-------------------VASYFAAEHGPSVCGNAFRVK  86
Axmi428H                      IINAEPDS--------------------FAQRFAKLHGPSVCAIAIRVN  97

PfHPPD                        DSQKAYNRALELGAQPIHIDTGPM----ELNLPAIKGIGGAPLYLIDRFG  132
Avena_sativa                  DAABAFRVSVAKGARPAFAPADLG---HGFOLAEVELYGDVVLRFVSYPD  189
Avena_sativa__del             DAABAFRVSVAKGARPAFAPADLG---HGFOLAEVELYGDVVLRFVSYPD  188
Zea_mays                      DAEDAFRASVAAGARPAFGPVDLG---RGFRLAEVELYGDVVLRYVSYPD  189
Streptomyces_avermitilis      DARAAHAYAIEKGARSVAEPYELKDEKGTVVLAKIATYSETRHTLNERTG  157
Arabidopsis_thaliana          DAESAFSISVANGAIPSSPPIVLN---SAVTIAEVKLYGDVVLRYVSYKA  194
Hordeum_vulgare               DAAEAFRASRNEGARPAFAPVDLG---RGFAFAEVELYGDVVLRFVSKPD  183
Daucus_carota                 DVAAAFEASVARGARPASAPVELD---DQARLAEVELYGDVVLRFVSFGK  189
Mycosphaerella_graminicola    DVLAVYENAVANGAKSVSSPHTGSCDKGDVISAAIKTYGDTTRTFIQPTT  189
Coccicoides_imnitis           CVESVFSAAVRNGAEVVSDVPTVEDEDQIKNATIETYGETTRTLIERSG  168
Axmi309H                      DSQKAYNRALELGAQPIHTSGPM----ELNLPAIKGIGGAPLYLIDRFG  130
Axmi428H                      DAKYAYERATSLGANGYAQQAAPG----ELSIPAIKGIGDSLIYFIDKWR  143
```

FIG. 1A

```
PfHPPD                    --EGS---------SIYDIDFVYLEG----VERNPVGAGLKVIDHLTENVYR 169
Avena_sativa              ETD-----------LPFLPGFERVS-----SPGAVDYGLTRFDHVVGN--V 222
Avena_sativa_del          ETD-----------LPFLPGFERVS-----SPGAVDYGLTRFDHVVGN--V 221
Zea_mays                  GAAG----------EPFLPGFECVA-----SPGAADYGLSRFDHIVGN--V 223
Streptomyces_avermitilis  YDG-----------PYLPGYVAAAPIVEPSAHK---TPQAIDHCVGNVEL 193
Arabidopsis_thaliana      EDTEK---------SEFLPGFERVEDA--ESFP-LDYGIRRLDHAVGN--V 233
Hordeum_vulgare           GTD-----------VPFLPGFEGVT-----NPEAVDYGLTRFDHRVVGN--V 216
Daucus_carota             EE------------GLFLPGFEAVEGT--ASPPDLDYGIRRLDHAVGN--V 204
Mycosphaerella_graminicola YTD-----------PFLPGYRSCTTVDGANKFLPPVRLEAIDHCVGNQDW 259
Coccicoides_immitis       YRG-----------GPMPGYRPESRADATSKFLPKVVLERIDHCVGNQDW 267
Axmi309H                  --EGS---------SIYDIDFVPLEG----VDRNPVGRGLKIIDHLTENVYR 169
Axmi428H                  OKNGAKDGDLGNISFPVDFEFLPG----ADLHPEGLGLTTIDHLTNVYR 190
                                                                      *

PfHPPD                    GRMVYWANFYEKLFNFREAKYF---DIKGEYTGLTSEAMSAPDGMIRIFL 216
Avena_sativa              PEMAPVIDYRKSPLGPHEPAEPTAEDVGTTESGLNSVVLANNSEAVLLPL 272
Avena_sativa_del          PEMAPVIDYNKSPLSPHEPAEPTAEDVGTTESGLNSVVLANNSEAVLLPL 271
Zea_mays                  PELAPAAAYPAGPTGPHEPAEPTTEDVGTAESGLNSMVLANNSENVLLPL 273
Streptomyces_avermitilis  GRMNERVGPYNKVRGPTNMKEPVGDDIATEVSALMSKVVADKTLKVKFPI 243
Arabidopsis_thaliana      PELGPALTYVAGPTGFKQPAEPTADDVGTARSGLNSAVLASNDSMVLLPI 281
Hordeum_vulgare           PELAPAAAYIAGFTGPHSPAEPTAEDVGTTESGLNSVVLANNSEGVLLPL 266
Daucus_carota             TELGPVVEYIEGFTGFHSPAEPTAEDVGTLESGLNSVVLANNSEMVLLPL 274
Mycosphaerella_graminicola LEMSDACDPYERCLSFHRFNGVDDKDICTEFSALKSIVNASPNQVVEKPI 278
Coccicoides_immitis       DEKEPVCDYYEKILGFHRFNGVDDKDICTEFSALKSIVMASPNDIVEKPI 317
Axmi309H                  GRMAYWANFYEKLFNFREIRYF---DIKGEYTGLTSKAKTAPDGMTRIPL 216
Axmi428H                  GPMAELAEFYERIFNFREIRYF---DIESQATGVKSKAKTSPCGKTRIPI 237
                                                                      *

PfHPPD                    NE--ESSKGAGQIEEFLKQFNSEGIQKVAPLTDDLVKTWSDALKKI----G 260
Avena_sativa              NEPVEGTERRSQIQTYLEYHGSPGVQHIALASNDVLRTLERMARTPMSG 322
Avena_sativa_del          NEPVEGTKRRSQIQTYLEYHGSPGVQHIALASNDVLRTLERMARTPMSG 321
Zea_mays                  NEPVEGTKRPSQIQTYLEHHGSPGVQHMALASPDVLPTLSMQARSAMGG 323
Streptomyces_avermitilis  NRPALAKK-KSQIDRYLEFYGSACVQHIALNTSDIVETEVPTNRAA----G 288
Arabidopsis_thaliana      NEPVHGTKRKSQIQTYLEHHEGAGLQHLALMSRDIFRTLRENRKRSSIGG 331
Hordeum_vulgare           NEPVEGTKRPSQIQTFLEHHGSPGVQHIAVASSDVLRTLSKMEARSAMGG 316
Daucus_carota             NRPVYGTERKSQIQTYLSNHEGAGVQHLALVSETIFRTLREMERKSCLSG 324
Mycosphaerella_graminicola NEPAKGKE-KSQIEEYVDFYGSPGVQHIALRTPNIFEAVSNLESR----G 323
Coccicoides_immitis       NEPAKRKK-QSQIERYVDFYNGASVQRIALRTNNIIDAITELKAD----G 362
Axmi309H                  NE--ESSKGAGGIEEFLKQFNGESIQRVAPLTDDLVKTWDQLKKI----G 260
Axmi428H                  NE--ERDKACGIQRYLDWYRGESIQRIALGSTSLYDTVDGLQWS----G 281
                                    *  * *       *    *

PfHPPD                    NRFMTAPPDTYYEKLEGRLPDHGEPVDQLQARGILLDGSSVEGDERLLLQ 310
Avena_sativa              PEFMAPPQAKYYPGVRRIAGDVLS--SRQIKECQELGVLVDRDRQNVLLQ 370
Avena_sativa_del          PEFMAPPQAKYYPGVRRIAGDVLS--SRQIKECQELGVLVDRDQSNVLLQ 369
Zea_mays                  PEFMAPFTSDYDGVRRAGDVLT--EAQIKEQGELGVLVDRDRQSVLLQ 371
Streptomyces_avermitilis  VQFLEFP-DSYYDTLGKWVGDT----RVPVGTLRELEILARORDEGYLLQ 333
Arabidopsis_thaliana      PDFMPSPPTYYQNLKKRVGDVLS--DDQIKECEELGILVDRDRQGTLLQ 379
Hordeum_vulgare           PDFLPPPLPKYYPGVRRLAGDVLS--EAQIKECQELGVLVDRDRQSVLLQ 364
Daucus_carota             PEFMPSPPTYYSNLANFVGDVLS--DRQIKEEELGILLVDRDRQTLLLQ 372
Mycosphaerella_graminicola VEFISVP-DTYYRNMRLFLKAAGMKLRESFDIIQKLNILIDFDSGYLLQ 372
Coccicoides_immitis       TEFIKVP-ETYYEDMKIRLKEQELVLDEDFETLKSLDILIDFDSGYLLQ 361
Axmi309H                  NRFMTAPPDTYYEKLEGRLFNRGEPVDQLQSRGILLKGASDKEDKRLLLQ 310
Axmi428H                  IYLMNTR-ETYYELLPKRIPDLQEPIPELLARNILVDGQPGR----LLLQ 326
                                  **                     ***
```

FIG. 1B

```
PfHPPD              IPSETLMG--PVFFEFIQRK--------------GKDGFGRGNFKALFE 343
Avena_sativa        IPTKPVGDRPTPFLEMIQRIGCMEKDEVOQEYQKGCGCGSFGKGNFSELFK 430
Avena_sativa_del    IPTKPVGDRPTPFLEMIQRIGCMEKDEVOQEYQKGCGCGSFGKGNFSELFK 419
Zea_mays            IPTKPVGDRPTLFLEIIQRIGCMEKDEKQEYQKGCGCGSFGKGNFSQLFK 421
Streptomyces_avermitilis  IPTKPVGDRPTVFFEIIEPN--------------GSMGFGKGSFYALFE 368
Arabidopsis_thaliana IPTKPLGDRPTIFIEIIQPVGCMEKIEBGKAYQSGGCGSFGKGNFSELFK 429
Hordeum_vulgare     IPTKPVGDRPTLFLEMIQRIGCMEKDEBGEDYQKGCGSFGKGNFSELFK 414
Daucus_carota       IPTKPVGDRPTLFIEIIQRVGCMLKDDACQNYQKGCGSFGKGNFSELFK 432
Mycosphaerella_graminicola  LFTKPLMGRPTVFIEIIQRN--------------NPDGFGAGNFKSLPE 407
Coccicoides_immitis  LFTKHLMGRPTVFIEIIQRN--------------NPSGFGAGNFRALFE 386
Azmi309H            IFSETLMG--PVFFEFIQRK--------------GKDGFGEGNFKALFE 343
Azmi428H            IFSENQLG--PIFFEFIQRK--------------GNSGFGEGNFKALFE 359
                    :*::       ..*;*;*:*              . *** *** **:

PfHPPD              SIERDQVRRGVLTAD-------- 358
Avena_sativa        SIEDYEKSLRVKQSVVAQKS--- 440
Avena_sativa_del    SIEDYEKSLRVKQSVVAQKS--- 439
Zea_mays            SIEDYEKSLRAKQAAAAAAQGS  444
Streptomyces_avermitilis  AIERKQEYRGNL---------- 380
Arabidopsis_thaliana SIEEYEKTLEAKQLVG------- 448
Hordeum_vulgare     SIEDYEKSLEAKQSAAVQGS--- 434
Daucus_carota       SIEEYEKTLEAKQITEEAAA--- 443
Mycosphaerella_graminicola  AIERKQELRGNL---------- 419
Coccicoides_immitis  AIERKQALRGTLI--------- 399
Azmi309H            SIERDQVRRGVLATS------- 358
Azmi428H            TMELDQMRRGVLKT-------- 373
                    ::*  :
```

FIG. 1C

Query ID lcl|Query_143245
Description PfHPPD
Molecule type amino acid
Query Length 358

Subject ID lcl|Query_143247
Description PfHPPDevo41
Molecule type amino acid
Subject Length 358

| Score | Expect | Method | Identities | Positives | Gaps |
|---|---|---|---|---|---|
| 726 bits(1874) | 0.0 | Compositional matrix adjust. | 354/358(99%) | 354/358(98%) | 0/358(0%) |

```
Query   1    MADLYENPMGLMGFEFIEFASPTPGTLEPIFEIMGFTKVATHRSKNVHLYRQGEINLILN   60
             MADLYENPMGLMGFEFIEFASPTPGTLEPIFEIMGFTKVATHRSKNVHLYRQGEINLILN
Sbjct   1    MADLYENPMGLMGFEFIEFASPTPGTLEPIFEIMGFTKVATHRSKNVHLYRQGEINLILN   60

Query   61   NEPNSIASYFAAEHGPSVCGMAFRVKDSQKAYNRALELGAQPIHIDTGPMELNLPAIKGI  120
             NEPNSIASYFAAEHGPSVCGMAFRVKDSQKAYNRALELGAQPIHIDTGPMELNLPAIKGI
Sbjct   61   NEPNSIASYFAAEHGPSVCGMAFRVKDSQKAYNRALELGAQPIHIDTGPMELNLPAIKGI  120

Query   121  GGAPLYLIDRFGEGSSIYDIDFVYLEGVERNPVGAGLKVIDHLTHNVYRGRMVYWANFYE  180
             GGAPLYLIDRFGEGSSIYDIDFVYLEGVERNPVGAGLKVIDHLTHNVYRGRMVYWANFYE
Sbjct   121  GGAPLYLIDRFGEGSSIYDIDFVYLEGVERNPVGAGLKVIDHLTHNVYRGRMVYWANFYE  180

Query   181  KLFNFREARYFDIKGEYTGLTSKAMSAPDGMIRIPLNEESSKGAGQIEEFLMQFNGEGIQ  240
             KLFNFREARYFDIKGEYTGLTSKAMSAPDGMIRIPLNEESSKGAGQIEEFLMQFNGEGIQ
Sbjct   181  KLFNFREARYFDIKGEYTGLTSKAMSAPDGMIRIPLNEESSKGAGQIEEFLMQFNGEGIQ  240

Query   241  HVAFLTDDLVKTWDALKKIGMRFMTAPPDTYYEMLEGRLPDHGEPVDQLQARGILLDGSS  300
             HVAFLTDDLVKTWDALKKIGMRFMTAPPDTYYEMLEGRLPDHGEPVDQLQARGILLDGSS
Sbjct   241  HVAFLTDDLVKTWDALKKIGMRFMTAPPDTYYEMLEGRLPDHGEPVDQLQARGILLDGSS  300

Query   301  VEGDKRLLLQIFSETLMGPVFFEFIQRKGDDGFGEGNFKALFESIERDQVRRGVLTAD   358
             VEGDKRLLLQIFSETLMGPVFFEFIQRKGDDGFG  NF  LFESIERDQVRRGVLTAD
Sbjct   301  VEGDKRLLLQIFSETLMGPVFFEFIQRKGDDGFGPWNFAQLFESIERDQVRRGVLTAD   358
```

FIG. 2

OF HERBICIDE TOLERANCE TO 4-HYDROXYPHENYLPYRUVATE DIOXYGENASE (HPPD) INHIBITORS BY DOWN-REGULATION OF HPPD EXPRESSION IN SOYBEAN

CROSS-REFERENCE TO RELATED APPLICATIONS

This application is a National Stage Entry of PCT/US2018/056464, filed Oct. 18, 2018, which claims priority to U.S. provisional application No. 62/576,569, filed Oct. 24, 2017, the disclosures of each of which are hereby incorporated by reference in their entireties.

FIELD OF THE INVENTION

This invention relates to plant molecular biology, particularly, downregulation of 4-hydroxyphenylpyruvate dioxygenases (HPPDs) that confer improved tolerance to 4-hydroxyphenylpyruvate dioxygenase (HPPD) inhibitor herbicides in soybean.

BACKGROUND OF THE INVENTION

The 4-hydroxyphenylpyruvate dioxygenases (HPPDs) are enzymes which catalyze the reaction in which para-hydroxyphenylpyruvate (abbreviated herein as HPP), a tyrosine degradation product, is transformed into homogentisate (abbreviated herein as HG), the precursor in plants of tocopherol and plastoquinone (Crouch N. P. et al. (1997), Tetrahedron, 53, 20, 6993-7010, Fritze et al. (2004), Plant Physiology 134:1388-1400). Tocopherol acts as a membrane-associated antioxidant. Plastoquinone, firstly acts as an electron carrier between PSII and the cytochrome b6/f complex and secondly, is a redox cofactor for phytoene desaturase, which is involved in the biosynthesis of carotenoids.

Up to now, more than 1000 nucleic acid sequences from various organisms present in the NCBI database were annotated as coding for a putative protein having an HPPD domain. But for most of those, it has not been proven that the protein would have an HPPD enzymatic activity either in an in vitro assay or in an in planta approach, nor that such HPPD protein can confer herbicide tolerance to HPPD inhibitor herbicides when expressed in a plant. Several HPPD proteins and their primary sequences have been described in the state of the art, in particular the HPPD proteins of bacteria such as *Pseudomonas* (Rüetschi et al., Eur. J. Biochem., 205, 459-466, 1992, WO96/38567), Kordia (WO2011/076889) Synechococcus (WO2011/076877), and *Rhodococcus* (WO2011/076892), of protists such as Blepharisma (WO2011/076882), of euryarchaeota such as Picrophilus (WO2011/076885) of plants such as *Arabidopsis* (WO96/38567, GENBANK® AF047834), carrot (WO 96/38567, GENBANK® 87257), *Avena sativa* (WO2002/046387, WO2011/068567), wheat (WO2002/046387), *Brachiaria platyphylla* (WO2002/046387), *Cenchrus echinatus* (WO2002/046387), *Lolium rigidum* (WO2002/046387), *Festuca arundinacea* (WO2002/046387), *Setaria faberi* (WO 2002/046387), *Eleusine indica* (WO2002/046387), Sorghum (WO2002/046387, WO2012/021785), corn (WO2012/021785), Coccicoides (GENBANK® COITRP), of *Coptis japonica* (WO2006/132270), *Chlamydomonas reinhardtii* (ES 2275365; WO2011/145015), or of mammals such as mouse or pig.

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo protection normally provided by carotenoids (Norris et al. (1995), Plant Cell 7: 2139-2149). Bleaching of photosynthetically active tissues leads to growth inhibition and plant death.

Some molecules which inhibit HPPD, and which inhibit transformation of the HPP into homogentisate while binding specifically to the enzyme, have proven to be very effective herbicides.

At present, most commercially available HPPD inhibitor herbicides belong to one of these chemical families:
1) the triketones, e.g. sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione]; tembotrione [i.e. 2-[2-chloro-4-(methylsulfonyl)-3-[(2,2,2,-tri-fluoroethoxy)methyl] benzoyl]-1,3-cyclohexanedione]; tefuryltrione [i.e. 2-[2-chloro-4-(methylsulfonyl)-3-[[(tetrahydro-2-furanyl)methoxy] methyl]benzoyl]-1,3-cyclohexanedione]]; bicyclopyrone [i.e. 4-hydroxy-3-[[2-[(2-methoxyethoxy)methyl]-6-(trifluoromethyl)-3-pyridinyl]carbonyl]bicyclo[3.2.1]oct-3-en-2-one]; Benzobicyclon [i.e. 3-(2-chloro-4-mesylbenzoyl)-2-phenylthiobicyclo[3.2.1]oct-2-en-4-one];
2) the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-dione;
3) the isoxazoles, e.g. isoxaflutole [i.e. (5-cyclopropyl-4-isoxazolyl)[2-(methylsulfonyl)-4-(trifluoromethyl)phenyl] methanone]. In plants, isoxaflutole is rapidly metabolized in DKN, a diketonitrile compound which exhibits the HPPD inhibitor property;
4) the pyrazolinates, e.g. topramezone [i.e. [3-(4,5-dihydro-3-isoxazolyl)-2-methyl-4-(methylsulfonyl) phenyl](5-hydroxy-1-methyl-1H-pyrazol-4-yl)methanone], and pyrasulfotole [i.e. (5-hydroxy-1,3-dimethylpyrazol-4-yl(2-mesyl-4-trifluaromethylphenyl)methanone]; pyrazofen [i.e. 2-[4-(2,4-dichlorobenzoyl)-1,3-dimethylpyrazol-5-yloxy] acetophenone];
5) N (1,2,5-oxadiazol-3-yl)benzamides (WO2011/035874) and N-(1,3,4-oxadiazol-2-yl)benzamides (WO2012/126932), e.g. 2-methyl-N-(5-methyl-1,3,4-oxadiazol-2-yl)-3-(methylsulfonyl)-4-(trifluoromethyl)benzamide (hereinafter also named "Cmpd. 1");
6) N-(tetrazol-5-yl)- or N-(triazol-3-yl)arylcarboxamides (WO2012/028579), e.g. 2-chloro-3-ethoxy-4-(methylsulfonyl)-N-(1-methyl-1H-tetrazol-5-yl)benzamide (hereinafter also named "Cmpd.2"); 4-(difluoromethyl)-2-methoxy-3-(methylsulfonyl)-N-(1-methyl-1H-tetrazol-5-yl)benzamide (hereinafter also named "Cmpd. 3"); 2-chloro-3-(methylsulfanyl)-N-(1-methyl-1H-tetrazol-5-yl)-4-(trifluoromethyl) benzamide (hereinafter also named "Cmpd. 4"); 2-(methoxymethyl)-3-(methylsulfinyl)-N-(1-methyl-1H-tetrazol-5-yl)-4-(trifluoromethyl)benzamide (hereinafter also named "Cmpd. 5");
7) Pyridazinone derivatives as described in WO2013/050421 and WO2013/083774;
8) Substituted 1,2,5-oxadiazoles as described in WO2013/072300 and WO2013/072402; and
9) Oxoprazin derivatives as described in WO2013/054495.

These HPPD inhibitor herbicides can be used against grass and/or broad leaf weeds in field of crop plants that display metabolic tolerance, such as maize (*Zea mays*), rice (*Oryza Sativa*) and wheat (*Triticum aestivum*) in which they are rapidly degraded (Schulz et al. (1993), FEBS letters, 318, 162-166; Mitchell et al. (2001), Pest Management Science, Vol 57, 120-128; Garcia et al. (2000), Biochem., 39, 7501-7507; Pallett et al. (2001), Pest Management Science, Vol 57, 133-142). In order to extend the scope of use of these HPPD inhibitor herbicides, several efforts have been developed in order to confer to plants, particularly plants without or with an underperforming metabolic tolerance, a tolerance level acceptable under agronomic field conditions.

Besides the attempt of by-passing HPPD-mediated production of homogentisate (U.S. Pat. No. 6,812,010), overexpressing the sensitive enzyme so as to produce quantities of the target enzyme in the plant which are sufficient in relation to the herbicide has been performed (WO96/38567). Overexpression of HPPD resulted in better pre-emergence tolerance to the diketonitrile derivative (DKN) of isoxaflutole (IFT), but the tolerance level was not sufficient for tolerance to post-emergence treatment (Matringe et al. (2005), Pest Management Science 61: 269-276).

A third strategy was to mutate the HPPD in order to obtain a target enzyme which, while retaining its properties of catalyzing the transformation of HPP into homogentisate, was less sensitive to HPPD inhibitors than the native HPPD before mutation.

This strategy has been successfully applied for the production of plants tolerant to 2-cyano-3-cyclopropyl-1-(2-methylsulphonyl-4-trifluoromethylphenyl)-propane-1,3-dione and to 2-cyano-1-[4-(methylsulphonyl)-2-trifluoromethylphenyl]-3-(1-methylcyclopropyl)propane-1,3-dione (EP496630), two HPPD inhibitor herbicides belonging to the diketonitriles family (WO99/24585). Pro215Leu, Gly336Gu, Gly336Ile, and more particularly Gly336Trp (positions of the mutated amino acid are indicated with reference to the *Pseudomonas fluorescens* HPPD) were identified as mutations which are responsible for an increased tolerance to treatment with these diketonitrile herbicides.

More recently, introduction of a *Pseudomonas fluorescens* HPPD gene into the plastid genome of tobacco and soybean was shown to be more effective than nuclear transformation, conferring tolerance to post-emergence application of isoxaflutole (Dufourmantel et al. (2007), Plant Biotechnol J.5(1):118-33).

In WO2004/024928, the inventors sought to increase the prenylquinone biosynthesis (e.g., synthesis of plastoquinones, tocopherols) in the cells of plants by increasing the flux of the HPP precursor into the cells of these plants. This was done by connecting the synthesis of said precursor to the "shikimate" pathway by overexpression of a prephenate dehydrogenase (PDH) enzyme. They also noted that the transformation of plants with a gene encoding a PDH enzyme and a gene encoding an HPPD enzyme makes it possible to increase the tolerance of said plants to HPPD inhibitors.

In WO2009/144079, nucleic acid sequences encoding a HPPD with specific mutations at position 336 of the *Pseudomonas fluorescens* HPPD protein and their use for obtaining plants which are tolerant to HPPD inhibitor herbicides was disclosed.

In WO2002/046387, several domains of HPPD proteins originating from plants were identified that may be relevant to confer tolerance to various HPPD inhibitor herbicides, but neither in planta nor biochemical data were shown to confirm the impact of the as described domain functions.

In WO2008/150473, the combination of two distinct tolerance mechanisms—a modified *Avena sativa* gene coding for a mutant HPPD enzyme and a CYP450 Maize monooxygenase (nsf1 gene)—was exemplified in order to obtain an improved tolerance to HPPD inhibitor herbicides, but no data were disclosed demonstrating the synergistic effects based on the combination of both proteins.

Further, in US2011/0173718, a method to generate plants tolerant to HPPD inhibitors by overexpressing not only a gene coding for a tolerant HPPD, as for example from *Avena sativa*, but also in combination with several plant genes coding for an HST (homogentisate solanesyltransferase) protein was disclosed. However, the level of tolerance to selected HPPD inhibitor herbicides was rather limited.

In WO2011/094199 and US2011/0185444, the tolerance of several hundreds of soybean wild type lines to the HPPD inhibitor isoxaflutole was evaluated. Very few lines displayed reasonable levels of tolerance to the herbicides. The putative QTL (quantitative trait loci) responsible for the tolerance was identified. In this region of the genome, a gene coding for an ABC transporter was identified as being the main trait responsible for the improved tolerance to the HPPD inhibitor herbicide observed. However, transgenic plants expressing the identified genes did not display any improvement in tolerance to the tested HPPD inhibitor herbicides.

In WO2010/085705, several mutants of the *Avena sativa* HPPD were disclosed. It was shown that some of the variants displayed improved tolerance in vitro to the triketone "mesotrione," however, only very few mutants were expressed in tobacco plants. Additionally, none of the tobacco plants expressing these mutants displayed improved tolerance to mesotrione or isoxaflutole compared to tobacco plants expressing the wild type *Avena sativa* HPPD gene.

US 2012/0042413 describes polypeptides having HPPD activity but also showing a certain insensitivity to at least one HPPD inhibitor and further suggests a certain set of mutations at different positions of HPPD enzymes and finally discloses biochemical data as well as tolerance levels of plants containing few of such mutated HPPDs. In EP 2453012, several mutants of HPPD were described; however, the improved tolerance of the described mutants was not demonstrated in planta against several HPPD inhibitor herbicides.

WO2014/043435 describes mutant HPPD enzymes derived from the native *Pseudomonas fluorescens* HPPD nucleotide sequence (Pf-HPPD, 1077 bp, as described in WO2009/144079) having HPPD activity with broad tolerance to HPPD inhibitor herbicides as demonstrated by biochemical data and tolerance levels of plant containing several of the disclosed Pf-HPPD mutant enzymes.

SUMMARY OF THE INVENTION

Compositions and methods for conferring tolerance to HPPD inhibitor herbicides are provided.

Disclosed herein is a double-stranded ribonucleic acid (dsRNA) comprising a sense region with at least 94% sequence identity to a portion of at least 19 consecutive nucleotides of one or more endogenous HPPD gene(s) and an antisense region comprising a second sequence complementary to said sense region. In a preferred embodiment, a dsRNA comprising a sense region with at least 94% sequence identity to a portion of at least 19 consecutive nucleotides of SEQ ID NO: 89 and/or SEQ ID NO: 90 and an antisense region comprising a second sequence complementary to said sense region is disclosed herein. In one embodiment, the dsRNA sense region has at least 99% or has 100% sequence identity to a portion of at least 19 consecutive nucleotides of one or more endogenous HPPD gene(s), such as SEQ ID NO: 89 and/or SEQ ID NO: 90. In some embodiments, the dsRNA of the invention is expressed in a plant cell.

Also disclosed herein is a DNA comprising a promoter functional in a host cell, and a DNA encoding a dsRNA comprising a first and a second region, wherein said first region comprises a sequence with at least 94% sequence identity to a portion of at least 19 consecutive nucleotides of one or more endogenous HPPD genes and wherein said second region is complementary to said first region. In some embodiments, the HPPD gene is a sequence selected from the group consisting of: the RNA form of SEQ ID NO: 89 and/or SEQ ID NO: 90. In one embodiment of the invention, the host cell is a bacterial cell, a yeast cell, or a plant cell.

Also disclosed herein is a chimeric gene comprising the following operably linked DNA: (a) a plant-expressible promoter; (b) a DNA region which when transcribed yields a double-stranded RNA molecule targeting one or more endogenous HPPD genes of a plant, said RNA molecule comprising a first and second RNA region wherein: (i) said first RNA region comprises a nucleotide sequence of at least 19 consecutive nucleotides having at least 94% sequence identity to the nucleotide sequence of said gene; (ii) said second RNA region comprises a nucleotide sequence complementary to said at least 19 consecutive nucleotides of said first RNA region; and (iii) said first and second RNA region are capable of base-pairing to form a double-stranded RNA molecule between at least said 19 consecutive nucleotides of said first and second region; and (c) optionally, a 3' end region comprising transcription termination and polyadenylation signals functioning in plant cells. In one embodiment of the invention, the first RNA region comprises a nucleotide sequence of at least 19 consecutive nucleotides having at least 95% sequence identity SEQ ID NO: 89 and/or SEQ ID NO: 90. In another embodiment of the invention, the said first RNA region comprises at least 19 consecutive nucleotides of SEQ ID NO: 89 and/or SEQ ID NO: 90. In yet another embodiment of the invention, between said first and second RNA region, a spacer region containing a plant intron is present. In one embodiment of the invention, the promoter is a constitutive promoter. In yet another embodiment of the invention, a plant cell, plant or seed comprising the chimeric gene or the double-stranded RNA molecule described above is provided.

In a further embodiment, nucleotides encoding herbicide tolerant polypeptides are co-expressed with the dsRNA of the invention. In some embodiments, the herbicide tolerant polypeptide is an HPPD enzyme. In a preferred embodiment, the HPPD enzyme is a mutant HPPD enzyme derived from *Pseudomonas fluorescens* (Pf-HPPD). In a more preferred embodiment, the HPPD enzyme is an HPPD protein set forth in any of SEQ ID NOs: 1-59 and 78-88, as well as fragments and functional variants thereof.

Also disclosed herein is a method to increase tolerance to HPPD inhibitor herbicides, the method comprising introducing a dsRNA construct that targets one or more endogenous HPPD genes in a plant. In some embodiments, the dsRNA targets the nucleotide sequence of SEQ ID NO: 89 and/or SEQ ID NO: 90. In some embodiments, the method further comprises introducing a nucleotide sequence encoding an herbicide tolerant polypeptide in a plant. In some embodiments, the herbicide tolerant polypeptide encoded by the nucleotide sequence is an HPPD enzyme. In a preferred embodiment, the HPPD enzyme is a mutant HPPD enzyme derived from *Pseudomonas fluorescens* (Pf-HPPD). In a more preferred embodiment, the HPPD enzyme is an HPPD protein set forth in any of SEQ ID NOs: 1-59 and 78-88, as well as fragments and functional variants thereof.

Transformed plants, plant cells, tissues, and seeds that are tolerant to HPPD inhibitor herbicides by the introduction of the nucleic acids of the invention into the genome of the plants, plant cells, tissues, and seeds are also provided herein.

BRIEF DESCRIPTION OF THE FIGURES

FIG. 1 shows an alignment of amino acid sequence of HPPDs from microbial and plant species, including *Pseudomonas fluorescens* (SEQ ID NO: 1), *Avena sativa* (SEQ ID NO:63), a variant of the HPPD from *Avena sativa* (SEQ ID NO:64), *Zea mays* (SEQ ID NO:65), *Streptomyces avermitilis* (SEQ ID NO:69), *Arabidopsis thaliana* (SEQ ID NO:66), *Hordeum vulgare* (SEQ ID NO:67), *Daucus carota* (SEQ ID NO:68), *Mycosphaerella graminicola* (SEQ ID NO:70), and *Coccicoides immitis* (SEQ ID NO:71).

FIG. 2 shows an alignment of amino acid sequence of HPPD from *Pseudomonas fluorescens* (SEQ ID NO: 1) and recombinant Pf-HPPD-evo41 (SEQ ID NO: 16).

DETAILED DESCRIPTION OF THE INVENTION

Figure 3:
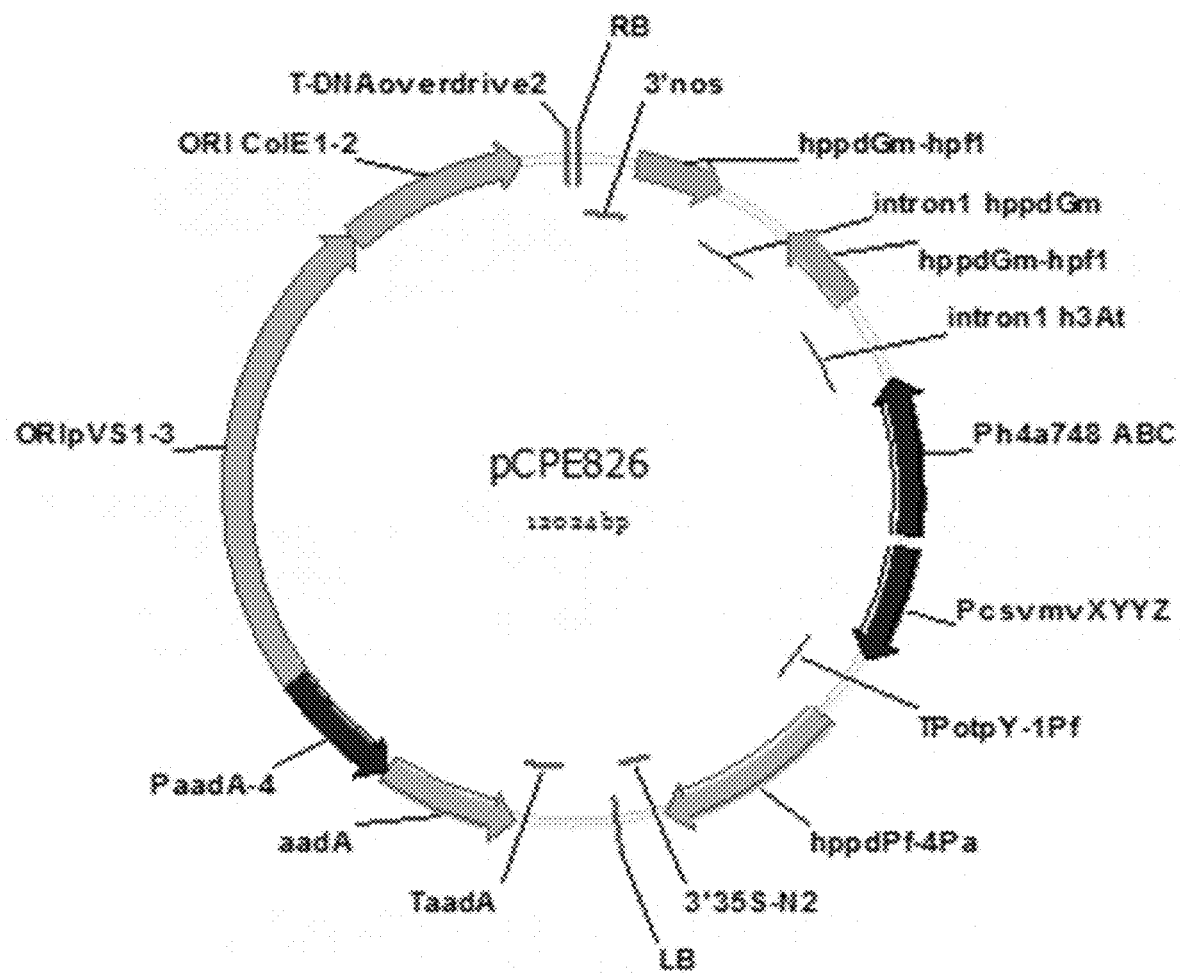
FIG. 3 shows a DNA construct in accordance with one embodiment of the present disclosure.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

Several efforts have been developed in order to confer to plants an agronomically-acceptable level of tolerance to a broad range of HPPD inhibitor herbicides, including by-passing HPPD-mediated production of homogentisate (U.S. Pat. No. 6,812,010), overexpressing the sensitive enzyme so as to produce quantities of the target enzyme in the plant which are sufficient in relation to the herbicide (WO96/38567), and mutating the HPPD in order to obtain a target enzyme which, while retaining its properties of catalyzing the transformation of HPP into homogentisate, is less sensitive to HPPD inhibitors than is the native HPPD before mutation.

Despite these successes obtained for the development of plants showing tolerance to several HPPD inhibitors herbicides described above, it is still necessary to develop and/or improve the tolerance of plants to newer or to several different HPPD inhibitors, particularly HPPD inhibitors belonging to the classes of the triketones (e.g. sulcotrione, mesotrione, tembotrione, benzobicyclon and bicyclopyrone), the pyrazolinates (e.g., topramezone and pyrasulfotole), N-(1,2,5-Oxadiazol-3-yl)benzamides (WO 2011/035874), and N-(tetrazol-4-yl)- or N-(triazol-3-yl) arylcarboxamides (WO2012/028579).

Thus, the present invention provides improved compositions and methods for regulating HPPD inhibitor herbicide tolerance. The inventors of the present disclosure surprisingly found that down-regulation of HPPD in soybean resulted in an improvement in herbicide tolerance to HPPD inhibitors.

Terms

As used herein, the singular form "a", "an" and "the" includes plural references unless the context clearly dictates otherwise. For example, the term "a cell" includes a plurality of cells, including mixtures thereof.

As used herein, the term "gene" refers to a DNA sequence involved in producing a RNA or polypeptide or precursor thereof. The polypeptide or RNA can be encoded by a full-length coding sequence or by intron-interrupted portions of the coding sequence, such as exon sequences. In one embodiment of the invention, the gene target is a HPPD gene.

As used herein, the term "oligonucleotide" refers to a molecule comprising a plurality of deoxyribonucleotides or ribonucleotides. Oligonucleotides may be generated in any manner, including chemical synthesis, DNA replication, reverse transcription, polymerase chain reaction, or a combination thereof. In one embodiment, the present invention embodies utilizing the oligonucleotide in the form of dsRNA as means of interfering with the expression of one or more HPPD enzymes. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

As used herein, the term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

As used herein, "dsRNA" refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single stranded RNA, but contains at least 19 nucleotides double-stranded RNA. In one embodiment of the invention, the dsRNA is a hairpin RNA which contains a loop or spacer sequence between the sense and antisense sequences of the gene targeted, preferably such hairpin RNA spacer region contains an intron.

As used herein, the term "gene silencing" refers to lack of (or reduction of) gene expression as a result of, though not limited to, effects at a genomic (DNA) level such as chromatin re-structuring, or at the post-transcriptional level through effects on transcript stability or translation. Evidence suggests that RNA interference (RNAi) is a major process involved in transcriptional and posttranscriptional gene silencing. Because RNAi exerts its effects at the transcriptional and/or post-transcriptional level, it is believed that RNAi can be used to specifically inhibit alternative transcripts from the same gene.

As used herein, the terms "interfering with" or "inhibiting" (expression of a target sequence) refers to the ability of a small RNA, such as an siRNA or a miRNA, or other molecule, to measurably reduce the expression and/or stability of molecules carrying the target sequence. A target sequence can include a DNA sequence, such as a gene or the promoter region of a gene, or an RNA sequence, such as an mRNA. "Interfering with" or "inhibiting" expression contemplates reduction of the end-product of the gene or sequence, e.g., the expression or function of the encoded protein or a protein, nucleic acid, other biomolecule, or biological function influenced by the target sequence, and thus includes reduction in the amount or longevity of the mRNA transcript or other target sequence. In some embodiments, the small RNA or other molecule guides chromatin modifications which inhibit the expression of a target sequence. It is understood that the phrase is relative, and does not require absolute inhibition (suppression) of the sequence. Thus, in certain embodiments, interfering with or inhibiting expression of a target sequence requires that, following application of the small RNA or other molecule (such as a vector or other construct encoding one or more small RNAs), the sequence is expressed at least 5% less than prior to application, at least 10% less, at least 15% less, at least 20% less, at least 25% less, or even more reduced. Thus, in some particular embodiments, application of a small RNA or other molecule reduces expression of the target sequence by about 30%, about 40%, about 50%, about 60%, or more. In specific examples, where the small RNA or other molecule is particularly effective, expression is reduced by 70%, 80%, 85%, 90%, 95%, or even more.

As used herein, the term "RNA interference" (RNAi) refers to gene silencing mechanisms that involve small RNAs (including miRNA and siRNA) are frequently referred to under the broad term RNAi. Natural functions of RNAi include protection of the genome against invasion by mobile genetic elements such as transposons and viruses, and regulation of gene expression.

RNA interference results in the inactivation or suppression of expression of a gene within an organism. RNAi can be triggered by one of two general routes. First, it can be triggered by direct cellular delivery of short-interfering RNAs (siRNAs, usually about 21 nucleotides in length and delivered in a dsRNA duplex form with two unpaired nucleotides at each 3' end), which have sequence complementarity to a RNA that is the target for suppression. Second, RNAi can be triggered by one of several methods in which siRNAs are formed in vivo from various types of designed, expressed genes. These genes typically express RNA molecules that form intra- or inter-molecular duplexes (dsRNA) or a "hairpin" configuration which are processed by natural enzymes (DICER or DCL) to form siRNAs. In some cases, these genes express "hairpin"-forming RNA transcripts with perfect or near-perfect base-pairing; some of the imperfect hairpin-forming transcripts yield a special type of small RNA, termed microRNA (miRNA). In either general method, it is the siRNAs (or miRNAs) that function as "guide sequences" to direct an RNA-degrading enzyme (termed RISC) to cleave or silence the target RNA. In some cases, it is beneficial to integrate an RNAi-inducing gene into the genome of a transgenic organism. An example would be a plant that is modified to suppress a specific gene by an RNAi-inducing transgene. In most methods that are currently in practice, RNAi is triggered in transgenic plants by transgenes that express a dsRNA (either intramolecular or hairpin, or intermolecular in which two transcripts anneal to form dsRNA).

As used herein, the term "RNA silencing" is a general term that is used to indicate RNA-based gene silencing or RNAi.

As used herein, the term "silencing agent" or "silencing molecule", refers to a specific molecule, which can exert an influence on a cell in a sequence-specific manner to reduce or silence the expression or function of a target, such as a target gene or protein. Examples of silencing agents include nucleic acid molecules such as naturally occurring or synthetically generated small interfering RNAs (siRNAs), naturally occurring or synthetically generated microRNAs (miRNAs), naturally occurring or synthetically generated dsRNAs, and antisense sequences (including antisense oligonucleotides, hairpin structures, and antisense expression vectors), as well as constructs that code for any one of such molecules.

As used herein, the term "small interfering RNA" (siRNA) refers to a RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity.

The term "chimeric" when referring to a gene or DNA sequence is used to refer to a gene or DNA sequence comprising at least two functionally relevant DNA fragments (such as promoter, 5'UTR, coding region, 3'UTR, intron) that are not naturally associated with each other, such as a fusion of functionally relevant DNA fragments from different sources to form a plant-expressible chimeric gene expressing a dsRNA targeting a HPPD gene.

Sequences or parts of sequences which have "high sequence identity", as used herein, refers to the number of positions with identical nucleotides divided by the number of nucleotides in the shorter of the sequences, being higher than 95%, higher than 96%, higher than 97%, higher than 98%, higher than 99%, or between 96% and 100%. A target gene, or at least a part thereof, as used herein, preferably has high sequence identity to the dsRNA of the invention in order for efficient gene silencing to take place in the target pest. Identity in sequence of the dsRNA or siRNA with a part of the target gene RNA is included in the current invention but is not necessary.

For the purpose of this invention, the "sequence identity" of two related nucleotide or amino acid sequences, expressed as a percentage, refers to the number of positions in the two optimally aligned sequences which have identical residues (x100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch 1970). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence X" is the nucleotide sequence which would be capable of forming a double-stranded DNA molecule with the represented nucleotide sequence, and which can be derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence.

In one embodiment of the invention, sense and antisense RNAs can be separately expressed in vitro or in host cells, e.g., from different chimeric gene constructs using the same or a different promoter or from a construct containing two convergent promoters in opposite orientation. These sense and antisense RNAs which are formed, e.g., in the same host cells, can then combine to form dsRNA. It is clear that whenever reference is made herein to a dsRNA chimeric gene or a dsRNA molecule, that such dsRNA formed, e.g., in plant cells, from sense and antisense RNA produced separately is also included. Also synthetically made dsRNA annealing RNA strands are included herein when the sense and antisense strands are present together.

A dsRNA "targeting" a HPPD gene, as used herein, refers to a dsRNA that is designed to be identical to or have high sequence identity to an endogenous HPPD gene in plants (the target gene), and as such is designed to silence such gene upon introduction to such plant. One dsRNA can target one or more homologous HPPD target genes in one plant or several homologous HPPD target genes in different plants. In one embodiment, the dsRNA of the invention targets multiple HPPD genes in soybean plants.

The dsRNA chimeric gene, encoding a dsRNA targeting a HPPD gene, can be stably inserted in a conventional manner into the genome of a single plant cell, and the so-transformed plant cell can be used in a conventional manner to produce a transformed plant that has increased resistance to HPPD inhibitor herbicides. For example, a disarmed Ti-plasmid, containing the dsRNA chimeric gene can be used to transform the plant cell, and thereafter, a transformed plant can be regenerated from the transformed plant cell using procedures known in the art. Other types of vectors can be used to transform the plant cell, using procedures such as direct gene transfer, pollen mediated transformation, plant RNA virus-mediated transformation, liposome-mediated transformation, and other methods such as the methods for transforming certain lines of corn (e.g., U.S. Pat. No. 6,140,553; Fromm et al., 1990, Bio/Technology 8, 833-839); Gordon-Kamm et al., 1990, The Plant Cell 2, 603-618) and rice (Shimamoto et al., 1989, Nature 338, 274-276; Datta et al., 1990, Bio/Technology 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (1988, Bio/Technology 6, 915) and Christou et al. (1990, Trends Biotechnology 8, 145) or the method of WO 00/42207.

The resulting transformed plant can be used in a conventional plant breeding scheme to produce more transformed plants with the same characteristics or to introduce the dsRNA chimeric gene in other varieties of the same or related plant species. Seeds, which are obtained from the transformed plants, contain the dsRNA gene as a stable genomic insert. Plants comprising a dsRNA in accordance with the invention include plants comprising or derived from root stocks of plants comprising the dsRNA chimeric gene of the invention, e.g., fruit trees or ornamental plants. Hence, any non-transgenic grafted plant parts inserted on a transformed plant or plant part are included in the invention since the RNA interference signal is transported to these grafted parts and any insects feeding on such grafted plant are similarly affected by the dsRNA or siRNA of the invention.

HPPD inhibitor herbicides of the present disclosure like those of the class of N (1,2,5-oxadiazol-3-yl)benzamides, N-(tetrazol-4-yl)- or N-(triazol-3-yl)arylcarboxamides, such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide, triketones, such as tembotrione, sulcotrione and mesotrione, the class of isoxazoles such as isoxaflutole, or of the class of pyrazolinates, such as pyrasulfotole and topramezone, particularly selected from tembotrione, sulcotrione, topramezone, bicyclopyrone, tefuryltrione, isoxaflutole, and mesotrione, have an outstanding herbicidal activity against a broad spectrum of economically important monocotyledonous and dicotyledonous annual harmful plants. The active substances also act efficiently on perennial harmful plants which produce shoots from rhizomes, wood stocks or other perennial organs and which are difficult to control. Within the meaning of the present invention, "herbicide" is understood as being a herbicidally active substance on its own or such a substance which is combined with an additive which alters its efficacy, such as, for example, an agent which increases its activity (a synergistic agent) or which limits its activity (a safener). The herbicide may further comprise solid or liquid adjuvants or carriers that are ordinarily employed in formulation technology (e.g. natural or regenerated mineral substances, solvents, dispersants, wetting agents, tackifiers, emulsifiers, growth promoting agents, and the like), as well as one or more additional herbicides and/or one or more pesticides (e.g., insecticides, virucides, microbicides, amoebicides, pesticides, fungicides, bacteriocides, nematocides, molluscicides, and the like).

The methods involve transforming organisms with nucleotide sequences encoding an HPPD inhibitor tolerance gene of the invention or otherwise introducing such HPPD inhibitor tolerance genes in organisms not containing them (e.g., by mating, cell fusion, or by crossing organisms containing an introduced HPPD inhibitor gene of the invention with organisms not containing it and obtaining progeny containing such gene). The nucleotide sequences of the invention are useful for preparing plants that show increased tolerance to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone. The HPPD inhibitor herbicide tolerance gene of the invention may also show tolerance towards the "coumarone-derivative herbicides" (described in WO2009/090401, WO2009/090402, WO2008/071918, WO2008/009908). In this regard, any one of the HPPD inhibitor herbicide tolerance genes of the invention can also be expressed in a plant also expressing a chimeric homogentisate solanesyltransferase (HST) gene or a mutated HST gene as described in WO2011/145015, WO2013/064987, WO2013/064964, or WO2010/029311, to obtain plants tolerant to HST inhibitor herbicides. As used herein, a "coumarone-derivative herbicide" or "HST inhibitor herbicide" encompasses compounds which fall under the IUPAC nomenclature of 5H-thiopyrano [4,3-b]pyridin-8-ol, 5H-thiopyrano[3,4-b]pyrazin-8-ol, oxathiino[5,6-b]pyridin-4-ol, and oxathiino[5, 6-b]pyrazin-4-ol.

Thus, by "HPPD inhibitor herbicide tolerance" gene of the invention is intended a gene encoding a protein that confers upon a cell or organism the ability to tolerate a higher concentration of an HPPD inhibitor herbicide than such cell or organism that does not express the protein, or to tolerate a certain concentration of an HPPD inhibitor herbicide for a longer time than such cell or organism that does not express the protein, or that confers upon a cell or organism the ability to perform photosynthesis, grow, and/or reproduce with less damage or growth inhibition observed than such cell or organism not expressing such protein. In various embodiments, the HPPD gene of the invention is selected from SEQ ID NO: 89 and/or SEQ ID NO: 90. An "HPPD inhibitor tolerance protein" includes a protein that confers upon a cell or organism the ability to tolerate a higher concentration of HPPD inhibitor herbicide than such cell or organism that does not express the protein, or to tolerate a certain concentration of HPPD inhibitor herbicide for a longer period of time than such cell or organism that does not express the protein, or that confers upon a cell or organism the ability to perform photosynthesis, grow, and/or reproduce with less damage or growth inhibition observed than such cell or organism not expressing such protein. By "tolerate" or "tolerance" is intended either to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide, such as the methods described in WO2011/100302, which is herein incorporated by reference in its entirety).

The HPPDs of the invention can be any endogenous HPPD protein. For the purposes of describing the HPPDs of the present invention, the terms "protein" and "polypeptide" and "enzyme" are used interchangeably.

In some embodiments, the HPPD protein is a soybean HPPD, such as the HPPD proteins set forth herein as SEQ ID NO: 92 and SEQ ID NO: 93.

In some embodiments, HPPD inhibitor tolerance is further enhanced by expressing at least one HPPD nucleic acid sequence encoding a polypeptide having HPPD activity, i.e., catalyzing the reaction in which para-hydroxyphenylpyruvate (HPP) is transformed into homogentisate. The catalytic activity of an HPPD enzyme may be defined by various methods well-known in the art. WO2009/144079 describes various suitable screening methods.

For the purposes of the present invention, a "reference" HPPD protein (or HPPD gene) is any HPPD protein or nucleic acid against which the HPPD protein or HPPD nucleic acid of the invention is being compared. For the purposes of describing the HPPD proteins of the present invention, the terms "protein" and "polypeptide" are used interchangeably. This reference HPPD can be a native plant, bacterial, or animal HPPD, or can be a mutated HPPD that is known in the art such as the PfP215L and PfG336W mutants described in International Patent Publication WO2009/144079 or can be either of the PfIPPDevo33, PfHIPPDevo36, PfIPPDevo37, PfIPPDevo40, or PfIPPDevo41, Axmi309H, Axmi428H, Axmi309H-Evo41, or Axmi428H-Evo41 proteins set forth herein as SEQ ID NO: 6, 7, 3, 8, 16, 58, 59, 54, and 56, respectively, which are also described in WO2014/043435, which is herein incorporated by reference. Such reference HPPD can be used to determine whether the HPPD protein or nucleic acid of the invention has a particular property of interest (e.g., improved, comparable or decreased HPPD inhibitor herbicide tolerance or HPPD enzyme activity; improved, comparable or decreased expression in a host cell; improved, comparable or decreased protein stability, and the like).

In various embodiments herein, the HPPD inhibitor herbicide tolerant protein encoded by a nucleic acid (including isolated, recombinant and chimeric genes thereof, vectors, host cells, plants, plant parts, and seeds comprising the nucleic acid, HPPD polypeptides and compositions thereof encoded by the nucleic acid, as well as methods of using the protein encoded by the nucleic acid for increasing tolerance of a plant to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) has been modified to contain one or more amino acid substitutions, including 2, 3, 4, 5, 6, or 7 amino acid substitutions, at the positions corresponding to amino acid positions 188, 189, 215, 335, 336, 339, and/or 340 of SEQ ID NO:1. By "corresponding to" is intended the nucleotide or amino acid position relative to that position in SEQ ID NO:1 when two (or more) sequences are aligned using standard alignment algorithms described elsewhere herein. A representative alignment of SEQ ID NO:1 with HPPD amino acid sequences from various microbial and plant species is shown in FIG. 1A-C. For example, amino acid positions 188, 189, 215, 335, 336, 339, and 340 of SEQ ID NO:1 correspond to amino acid positions 241, 242, 271, 412, 413, 416, and 417, respectively, of the HPPD from *Avena sativa* (SEQ ID NO:63); to amino acid positions 235, 236, 265, 406, 407, 410, and 411, respectively, of the HPPD from *Hordeum vulgare* (SEQ ID NO:67) and to amino acid positions 242, 243, 272, 413, 414, 417, and 418, respectively, of the HPPD from *Zea mays* (SEQ ID NO:65). Accordingly, depending on the length of the concerned HPPD amino acid sequence, having either additional or fewer residues than the sequence of SEQ ID NO:1, the corresponding position can be located at a position different from positions 188, 189, 215, 335, 336, 339, and 340 in such concerned HPPD protein.

In one embodiment, the HPPD of the present invention has been modified to comprise one or more amino acid substitution(s) selected from the group consisting of:

(a) a tryptophan, glycine, or serine at the amino acid position corresponding to amino acid position 188 of SEQ ID NO:1;

(b) a serine, cysteine, or arginine at the amino acid position corresponding to amino acid position 189 of SEQ ID NO:1;

(c) a proline, serine, histidine, alanine, glycine, or glutamine at the amino acid position corresponding to amino acid position 335 of SEQ ID NO:1;

(d) a serine or tryptophan at the amino acid position corresponding to amino acid position 336 of SEQ ID NO:1;

(e) a threonine, alanine, or serine at the amino acid position corresponding to amino acid position 339 of SEQ ID NO:1;

(f) a glutamine, alanine, valine, or glutamic acid at the amino acid position corresponding to amino acid position 340 of SEQ ID NO:1; and (g) a leucine at the amino acid position corresponding to amino acid position 215 of SEQ ID NO:1.

In another embodiment, the HPPD has been modified to comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In specific embodiments, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:1, wherein the HPPD has been modified to comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:1 and wherein said HPPD comprises the amino acid substitution(s) of:

(a) a tryptophan at amino acid position 188 and a tryptophan at amino acid position 336; or (b) a proline at amino acid position 335.

In yet another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:63, wherein the HPPD has been modified to comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1 and a serine at the amino acid position corresponding to amino acid position 336 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In yet another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:64, wherein the HPPD has been modified to comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1 and a serine at the amino acid position corresponding to amino acid position 336 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In yet another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:65, wherein the HPPD has been modified to comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, and a threonine at the amino acid position corresponding to amino acid position 339 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, and an alanine at the amino acid position corresponding to amino acid position 339 of SEQ ID NO:1; or (f) a proline at the amino acid position corresponding to amino acid position 335 of SEQ ID NO:1.

In another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence set forth herein as SEQ ID NO:57, or is encoded by a nucleotide sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the nucleotide sequence set forth herein as SEQ ID NO:60. The HPPD of this embodiment may further comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1; an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence set forth herein as SEQ ID NO:58, or is encoded by a nucleotide sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the nucleotide sequence set forth herein as SEQ ID NO:61. The HPPD of this embodiment may further comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1; an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 53%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence set forth herein as SEQ ID NO:59, or is encoded by a nucleotide sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the nucleotide sequence set forth herein as SEQ ID NO:62. The HPPD of this embodiment may further comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1; an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 85% sequence identity to the amino acid sequence set forth herein as SEQ ID NO:1, wherein the HPPD has been modified to comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 85% sequence identity to the amino acid sequence set forth herein as SEQ ID NO:1 and wherein said HPPD comprises the amino acid substitution(s) of:

(a) a tryptophan at amino acid position 188 and a tryptophan at amino acid position 336; or (b) a proline at amino acid position 335.

In another embodiment, the HPPD of the invention has at least 85% sequence identity to the amino acid sequence set forth herein as SEQ ID NO:57. The HPPD of this embodiment may further comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 85% sequence identity to the amino acid sequence set forth herein as SEQ ID NO:58. The HPPD of this embodiment may further comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

In another embodiment, the HPPD of the invention has at least 85% sequence identity to the amino acid sequence set forth herein as SEQ ID NO:59. The HPPD of this embodiment may further comprise amino acid substitution(s) of:

(a) a proline at the amino acid position corresponding to amino acid position 335 of SEQ ID NO:1 and a tryptophan at the amino acid position corresponding to amino acid position 336 of SEQ ID NO:1;

(b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;

(c) a tryptophan at the amino acid position corresponding to amino acid position 188 of SEQ ID NO:1 and a tryptophan at the amino acid position corresponding to amino acid position 336 of SEQ ID NO:1;

(d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1;

(e) a proline at the amino acid position corresponding to amino acid position 335 of SEQ ID NO:1, a tryptophan at the amino acid position corresponding to amino acid position 336 of SEQ ID NO:1; an alanine at the amino acid position corresponding to amino acid position 339 of SEQ ID NO:1, and a glutamine at the amino acid position corresponding to amino acid position 340 of SEQ ID NO:1; or (f) a proline at the amino acid position corresponding to amino acid position 335 of SEQ ID NO:1.

Any HPPD sequence can be modified to contain one or more of the substitutions disclosed herein. For example, the HPPD of the invention also encompasses any naturally-occurring bacterial, plant, or animal HPPD enzymes that has been modified to contain one or more of the substitutions described supra.

In arriving at the HPPD protein of the current invention, a starting amino acid sequence of an existing protein has to be modified by man by replacing at least one amino acid as defined in the present application, which is most conveniently done by modifying the DNA encoding such protein by replacing a certain codon by another codon encoding another amino acid.

Exemplary HPPD sequences that can be modified according to the present invention include those from bacteria, for example, of the *Pseudomonas* sp. type, for example *Pseudomonas fluorescens*, or otherwise cyanobacteria of the *Synechocystis* genus. The sequence can also be of plant origin, in particular derived from dicotyledonous plants, umbelliferous plants, or otherwise monocotyledonous plants. Advantageous examples which may be cited are plants such as tobacco, *Arabidopsis*, *Daucus carotta*, *Zea mays* (corn), wheat, barley, *Avena sativa*, *Brachiaria platyphylla*, *Cenchrus echinatus*, *Lolium rigidum*, *Festuca arundinacea*, *Setaria faberi*, *Eleusine indica*, Sorghum. The coding sequences, and the way of isolating and cloning them, are known in the art or described elsewhere herein (e.g., SEQ ID NO:63-76). In a particular embodiment of the invention, the HPPD that can be modified according to the present invention is from a bacterial origin, particularly from *Pseudomonas* sp., more particularly from *Pseudomonas fluorescens*, *Rhodococcus* sp., *Blepharisma japonicum*, *Synechococcus* sp., *Picrophilus torridus*, *Kordia algicida* or from a plant origin, including from *Arabidopsis thaliana*, *Sorghum bicolor*, *Oryza sativa*, *Triticum aestivum*, *Hordeum vulgare*, *Lolium rigidum*, or *Avena sativa*.

For the purposes of the present invention, the HPPD of the invention may also comprise further modifications, for example, wherein some amino acids (e.g., 1 to 10 amino acids) have been replaced, added or deleted for cloning purposes, to make a transit peptide fusion, and the like, which retains HPPD activity, i.e. the property of catalyzing the conversion of para-hydroxyphenylpyruvate to homogentisate, or can be any HPPD that can be further improved. For example, the HPPD that can be further improved by the modifications described herein can be the variant HPPD derived from *Pseudomonas fluorescens* set forth herein as SEQ ID NO:2, the variant HPPD from *Avena sativa* set forth herein as SEQ ID NO:64, the variant HPPD sequences set forth in any of SEQ ID NO:3-326, 383-389, 393, 395, and 397-459 in WO2012/021785, which is herein incorporated by reference in its entirety; the HPPD sequences set forth in any of SEQ ID NO:2-14 and 20-50 of WO2011/068567, which is herein incorporated by reference in its entirety; the HPPD sequences set forth in any of SEQ ID NO:15-26 of WO2010/085705, which is herein incorporated by reference in its entirety; an HPPD having one or more of the substitutions described in WO09/144079 or U.S. Pat. No. 6,245,968, each of which is herein incorporated by reference in its entirety; an HPPD having one or more of the substitutions described in Tables 1, 2, 5, or 6 of WO2010/085705; and/or an HPPD having one or more of the substitutions described in Table 1 of WO2011/068567; the variant HPPD sequences set forth in any of SEQ ID NO:3-59 of WO2014/043435; or an HPPD having one or more of the substitutions described in Table 1 of WO2015/0138394, which is herein incorporated by reference in its entirety.

In some embodiments, the nucleotide sequence of the invention (including isolated, recombinant and chimeric genes thereof, vectors, host cells, plants, plant parts, and seeds comprising the nucleic acid sequence, amino acid sequences and compositions thereof encoded by the nucleic acid sequence, as well as methods of using the nucleic acid sequence for increasing tolerance of a plant to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4)t 2-(methoxymethyl)-3-(methylsulfinyl)-N-(1-methyl-H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) encodes the amino acid sequence set forth in any one of SEQ ID NO:3-59 and 78-88, and fragments and variants thereof that encode a HPPD inhibitor herbicide tolerance polypeptide. Thus, in this embodiment, the HPPD of the invention comprises the amino acid sequence set forth in any of SEQ ID NO:3-59 and 78-88, and fragments and variants thereof, that confer tolerance to HPPD inhibitor herbicides in a host cell.

A. Methods for Measuring HPPD Inhibitor Tolerance

Any suitable method for measuring tolerance to HPPD inhibitor herbicides can be used to evaluate the transformants of the invention. Tolerance can be measured by monitoring the ability of a cell or organism to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide). In some embodiments, tolerance can be measured according to a visible indicator phenotype of the cell or organism transformed with a nucleic acid comprising the RNAi region designed to silence the endogenous HPPD protein(s) and/or the gene coding for the respective HPPD protein, or in an in vitro assay of the HPPD protein, in the presence of different concentrations of the various HPPD inhibitors. Dose responses and relative shifts in dose responses associated with these indicator phenotypes (formation of brown color, growth inhibition, bleaching, herbicidal effect etc.) are conveniently expressed in terms, for example, of GR50 (concentration for 50% reduction of growth) or MIC (minimum inhibitory concentration) values where increases in values correspond to increases in inherent tolerance to HPPD inhibitors, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance to HPPD inhibitors. Herbicides can suitably be applied pre-emergence or post emergence.

In various embodiments, tolerance level of the transformants of the invention can be screened via transgenesis, regeneration, breeding and spray testing of a test plant such as tobacco, or a crop plant such as soybean, corn, or cotton. In line with the results obtained by such screening, such plants are more tolerant, desirably tolerant to at least 2 times the normal dose recommended for field applications, even more preferably tolerant up to 4 times the normal dose recommended for field applications, to HPPD inhibitor herbicides (e.g., HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) than such plants that express normal levels of HPPD enzymes and/or do not contain any exogenous gene encoding an HPPD protein, or than plants that contain a gene comprising a reference HPPD-encoding DNA, for example, a *Pseudomonas fluorescens* HPPD-encoding DNA, under control of the same promoter as the nucleic acid encoding the HPPD protein of the invention. Accordingly, the term "capable of increasing the tolerance of a plant to at least one herbicide acting on HPPD" denotes a tolerance by the plant expressing the HPPD of the invention to at least 1×, 2×, or 3×, or 4×, or greater, the normal field dose of the HPPD inhibitor herbicide as compared to a plant only expressing its endogenous HPPD or a plant expressing a reference HPPD enzyme. In this regard, the term "herbicide acting on HPPD" is not limited to substances which are known and/or used as herbicides but to any substances which inhibit the catalytic activity of HPPD proteins.

Alternatively, at the quantitative level data like $pI_{50}$ ($pI_{50}$-value means the log value of the concentration of inhibitor necessary to inhibit 50% of the enzyme activity in molar concentration) can be obtained for the transformants of the invention and compared to a cell expressing normal levels of HPPD enzyme(s) and/or a reference HPPD sequence in the presence or absence of any respective HPPD inhibitor herbicide.

A specific, although non-limiting, type of assay that can be used to evaluate the transformants of the invention is a colorimetric assay. In this assay, a YT-broth-type culture medium with 1% agarose, 5 mM L-Tyrosine and 42 mM Succinate, which contains the selection agent for the vector pSE420 (Invitrogen, Karlsruhe, Germany) or a modified version of pSE420 (pSE420(RI)NX) is poured into deep well plates. *E. coli* culture in the exponential growth phase which contains the vector pSE420-HPPDx (HPPDx means any gene coding for a putative HPPD enzyme/protein) is applied to each well. After 16 hours at 37° C., the wells which do not contain the culture medium, those which have been seeded with an *E. coli* culture containing the empty vector pSE420 are transparent, or those which have been seeded with an *E. coli* culture containing a vector pSE420-HPPDx containing a gene coding for an inactive HPPD are transparent, while the wells seeded with an *E. coli* culture containing the vector pSE420-HPPDx coding for an active HPPD are brown. It has been previously demonstrated that this test reflects the HPPD activity, whatever the origin of this activity is, and allows the identification of HPPD activities (U.S. Pat. No. 6,768,044), i.e. at a qualitative level.

B. Methods of Reducing HPPD Expression in Plant Cells

In a preferred embodiment of the invention, HPPD expression is reduced using RNA interference as described above. Accordingly, one or more genes encoding HPPD may be targeted.

Information on how to design optimal dsRNA sequences once a target gene is known can be found with commercial providers, e.g., the companies Ambion and Cenix BioScience (Ambion Inc., 2130 Woodward Street, Austin, Tex. 78744-1832, USA; and Cenix BioScience GmbH, Pfotenhauerstr. 108, 01307 Dresden, Germany, see www.cenix-bioscience.com). Preferably, the dsRNAs to be used in this invention target at least one HPPD plant gene, or a HPPD plant gene portion of at least 19 consecutive nucleotides occurring in identical sequence or with high sequence identity in a several plant species. In one embodiment, a portion of a target HPPD gene sequence is selected which is present in several plant hosts with identical sequence or with high sequence identity, of a length sufficient to be capable of silencing the HPPD gene.

In one embodiment of this invention, the dsRNA or siRNA of the invention corresponds to an exon in the target gene.

Also, in the dsRNA chimeric gene of the invention a nuclear localization signal can be added as described in published US patent application 20030180945 (incorporated herein by reference).

As used herein, nucleotide sequences of RNA molecules may be identified by reference to DNA nucleotide sequences of the sequence listing. However, the person skilled in the art will understand whether RNA or DNA is meant depending on the context. Furthermore, the nucleotide sequence is identical except that the T-base is replaced by uracil (U) in RNA molecules.

The length of the first (e.g., sense) and second (e.g., antisense) nucleotide sequences of the dsRNA molecules of the invention may vary from about 10 nucleotides (nt) up to a length equaling the length in nucleotides of the transcript of the target gene. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known and which meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% With the corresponding target sequence, but higher sequence identity can also be used such as at least about 80%, at least about 85%, at least about 90%, at least about 95%, about 100%. The first nucleotide sequence can also be identical to the corresponding part of the target gene. However, it is advised that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is advised that the antisense nucleotide sequence always includes a sequence of 19 or 20, about 19 or about 20 consecutive nucleotides, although longer stretches of consecutive nucleotides such as about 50 nucleotides, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, the DNA molecules according to the invention may comprise a DNA region encoding a spacer between the DNA region encoding the first and second nucleotide sequences. As indicated in WO 99/53050 the spacer may contain an intron to enhance gene silencing. A particularly preferred intron functional in cells of plants is the pdk intron (*Flaveria trinervia* pyruvate orthophosphate dikinase intron 2; see WO99/53050 incorporated by reference), the delta 12 desaturase intron from *Arabidopsis* (Smith et al., 2000, Nature 407:319-20) or the intron of the rolA gene (Magrelli et al., 1994, Science 266: 1986-1988; Spena and Langenkemper, 1997, Genet. Res. 69:11-15).

In one embodiment of the invention, the dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can basepair amongst themselves.

"Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene.

Methods which are well known to those skilled in the art may be used to construct expression vectors containing sequences encoding HPPD gene and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) Current Protocols in Molecular Biology, John Wiley & Sons, New York, N.Y.

While the examples provided herein describe dsRNA constructs cloned from GenBank Accession Nos. NM_001248219.1 (gene ID: LOC100101901; *Glycine max*), it is contemplated that when read in conjunction with the teaching disclosed herein and the knowledge in the art, the construction of other dsRNA constructs targeting HPPD gene sequences of other plant species would be feasible to those skilled the in the art. For example, including but not limited to the HPPD gene/amino acid sequences disclosed herein, it is contemplated that a dsRNA construct targeting other plant species would increase tolerance to HPPD inhibitor herbicides in those plants. Additionally, it is contemplated that a single dsRNA construct would be effective in increasing tolerance to HPPD inhibitor herbicides in a plurality of plant species.

C. Methods of Introducing Mutations into HPPD Sequences

In the mutated HPPD protein encoded by the nucleic acid of the invention at least one amino acid has been replaced as defined above.

The replacement can be effected in the nucleic acid sequence which encodes the reference HPPD as defined above by any means which is appropriate for replacing, in the said sequence, the codon which encodes the amino acid to be replaced with the codon which corresponds to the amino acid which is to replace it, with the said codons being widely described in the literature and well known to the skilled person.

Several molecular biological methods can be used to achieve this replacement. A useful method for preparing a mutated nucleic acid sequence according to the invention and the corresponding protein comprises carrying out site-directed mutagenesis on codons encoding one or more amino acids which are selected in advance. The methods for obtaining these site-directed mutations are well known to the skilled person and widely described in the literature (in particular: Directed Mutagenesis: A Practical Approach, 1991, Edited by M. J. McPHERSON, IRL PRESS), or are methods for which it is possible to employ commercial kits (for example the QUIKCHANGE™ lightening mutagenesis kit from Qiagen or Stratagene). After the site-directed mutagenesis, it is useful to select the cells which contain a mutated HPPD which is less sensitive to an HPPD inhibitor by using an appropriate screening aid. Appropriate screening methods to achieve this have been described above.

Alternatively, a DNA sequence encoding the reference HPPD can be modified in silico to encode an HPPD protein having one or more of the substitutions recited herein, and then synthesized de novo. The nucleotide sequence encoding the mutated HPPD protein can be introduced into a host cell as described elsewhere herein.

D. Isolated Polynucleotides, and Variants and Fragments Thereof.

In some embodiments, the present invention comprises isolated or recombinant, polynucleotides. A "recombinant" polynucleotide or polypeptide/protein, or biologically active portion thereof, as defined herein is no longer present in its original, native organism, such as when contained in a heterologous host cell or in a transgenic plant cell, seed or plant. In one embodiment, a recombinant polynucleotide is free of sequences (for example, protein encoding or regulatory sequences) that naturally flank the nucleic acid (i.e., sequences located at the 5' and 3' ends of the nucleic acid) in the genomic DNA of the organism from which the polynucleotide is derived. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. In another embodiment, a "recombinant" polynucleotide is free of internal sequences (i.e. introns) that naturally occur in the genomic DNA of the organism from which the polynucleotide is derived. A typical example of such polynucleotide is a so-called Complementary DNA (cDNA). For example, in various embodiments, the isolated HPPD inhibitor herbicide tolerance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived. Nucleic acid molecules of the invention include those designed to silence the HPPD(s) of the invention and/or those that encode the HPPD of the invention. In some embodiments, the nucleic acid molecule of the invention is operably linked to a promoter capable of directing expression of the nucleic acid molecule in a host cell (e.g., a plant host cell or a bacterial host cell).

In some embodiments, the polynucleotides of the invention include fragments of HPPD genes for use in silencing endogenous HPPD genes by repression of transcription as discussed above, such as dsRNA, hairpin RNA, and/or complementary RNA.

The present invention further contemplates variants and fragments of any nucleic acid sequence encoding the amino acid sequences set forth in any of SEQ ID NO: 1-59 and 78-88. A "fragment" of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, contiguous nucleotides, or up to the number of nucleotides present in a full-length polynucleotide disclosed herein depending upon the intended use (e.g., an HPPD nucleic acid described herein). By "contiguous" nucleotides are intended nucleotide residues that are immediately adjacent to one another.

Fragments of the HPPD polynucleotides of the present invention generally will encode polypeptide fragments that retain the biological activity of the full-length HPPD inhibitor herbicide tolerance protein; i.e., herbicide-tolerance activity. By "retains herbicide tolerance activity" is intended that the fragment will have at least about 30%, at least about 50%, at least about 70%, at least about 80%, 85%, 90%, 95%, 100%, 110%, 125%, 150%, 175%, 200%, 250%, at least about 300% or greater of the herbicide tolerance activity of the full-length HPPD inhibitor herbicide tolerance protein disclosed herein as SEQ ID NO: 1-59 and 78-88. Methods for measuring herbicide tolerance activity are well known in the art and exemplary methods are described herein. In a non-limiting example, a fragment of the invention will be tolerant to the same dose of an HPPD inhibitor herbicide, or tolerant to 1×, 2×, 3×, 4×, or higher dose of an HPPD inhibitor herbicide, or the fragments will be as or more tolerant based on pI50 or Ki between the fragment and SEQ ID NO: 1-59 and 78-88.

A fragment of a polynucleotide that encodes a biologically active portion of a polypeptide of the invention will encode at least about 150, 175, 200, 250, 300, 350 contiguous amino acids, or up to the total number of amino acids present in a full-length polypeptide of the invention. In a non-limiting example, a fragment of a polynucleotide that encodes a biologically active portion of a HPPD protein having a proline at the amino acid position corresponding to amino acid position 335 of SEQ ID NO:1 and a phenylalanine or a tyrosine at the position corresponding to amino acid position 336 of SEQ ID NO:1 and, optionally, one or more amino acid substitutions at the positions corresponding to amino acid positions 172, 188, 200, 226, 339, and 340 of SEQ ID NO:1, including the HPPD protein set forth in any of SEQ ID NO: 1-59 and 78-88.

The invention also encompasses variant polynucleotides as described supra. "Variants" of the polynucleotide also include those sequences that encode the HPPD of the invention but that differ conservatively because of the degeneracy of the genetic code, as well as those that are sufficiently identical. In some embodiments, variants of the present invention will retain HPPD enzyme activity and HPPD herbicide inhibitor tolerance. The term "sufficiently identical" is intended a polypeptide or polynucleotide sequence that has at least about 53%, at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art will recognize that these values can be appropriately adjusted to determine corresponding identity of polypeptides encoded by two polynucleotides by taking into account codon degeneracy, amino acid similarity, reading frame positioning, and the like.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide tolerance. These herbicide tolerance proteins are encompassed in the present invention and may be used in the methods of the present invention. Naturally occurring allelic variants can be identified with the use of well-known molecular biology techniques, such as polymerase chain reaction (PCR) and hybridization techniques as outlined below. Variant polynucleotides also include synthetically derived polynucleotides that have been generated, for example, by using site-directed or other mutagenesis strategies but which still encode the polypeptide having the desired biological activity.

The skilled artisan will further appreciate that changes can be introduced by further mutation of the polynucleotides of the invention thereby leading to further changes in the amino acid sequence of the encoded polypeptides, without altering the biological activity of the polypeptides. Thus, variant isolated polynucleotides can be created by introducing one or more additional nucleotide substitutions, additions, or deletions into the corresponding polynucleotide encoding the HPPD of the invention, such that 1-5, 1-10, or 1-15 amino acid substitutions, additions or deletions, or 1, 2, 3, 4, 5, 6, 7, 8, 9, 10, 11, 12, 13, 14, or 15 amino acid substitutions, additions or deletions, are introduced into the encoded polypeptide. Further mutations can be introduced by standard techniques, such as site-directed mutagenesis and PCR-mediated mutagenesis, or gene shuffling techniques. Such variant polynucleotides are also encompassed by the present invention.

Variant polynucleotides can be made by introducing mutations randomly along all or part of the coding sequence, such as by saturation mutagenesis or permutational mutagenesis, and the resultant mutants can be screened for the ability to confer herbicide tolerance activity to identify mutants that retain activity.

Additional methods for generating variants include subjecting a cell expressing a protein disclosed herein (or library thereof) to a specific condition that creates a stress to the activity of the protein. Specific conditions can include (but are not limited to) changes in temperature, changes in pH, and changes in the concentrations of substrates or inhibitors. The protein library can be subjected to these conditions during the time of protein expression (e.g., in *E.* coli or other host) or following creation of a protein extract, or following protein purification.

The functional or enzymatic activity of the protein library that has been subjected to a stress condition can then be compared to the reference protein to identify proteins with improved properties. This activity comparison can be carried out as part of a growth screen or alternatively as part of an enzymatic assay that quantifies the activity of the protein. The properties that can be identified as improved can include HPPD inhibitor herbicide tolerance, changes in kinetic constants (including Km, Ki, $k_{cat}$), protein stability, protein thermostability, or protein temperature and pH optimum.

E. Isolated Proteins and Variants and Fragments Thereof

Herbicide tolerance polypeptides are also encompassed within the present invention. An herbicide tolerance polypeptide includes preparations of polypeptides having less than about 30%, 20%, 10%, or 5% (by dry weight) of non-herbicide tolerance polypeptide (also referred to herein as a "contaminating protein"). In the present invention, "herbicide tolerance protein" is intended an HPPD polypeptide disclosed herein. Fragments, biologically active portions, and variants thereof are also provided, and may be used to practice the methods of the present invention.

"Fragments" or "biologically active portions" include polypeptide fragments comprising a portion of an amino acid sequence encoding an herbicide tolerance protein and that retains herbicide tolerance activity. A biologically active portion of an herbicide tolerance protein can be a polypeptide that is, for example, 10, 25, 50, 100 or more amino acids in length. Such biologically active portions can be prepared by recombinant techniques and evaluated for herbicide tolerance activity.

By "variants" is intended proteins or polypeptides having an amino acid sequence that is at least about 53%, 60%, 65%, about 70%, 75%, about 80%, 85%, 90%, 91%, 92%, 93%, 94%, 95%, 96%, 97%, 98% or 99% identical to any of SEQ ID NO: 1-59 and 78-88, wherein said variant has HPPD enzyme activity and HPPD inhibitor herbicide tolerance One of skill in the art will recognize that these values can be appropriately adjusted to determine corresponding identity of polypeptides encoded by two polynucleotides by taking into account codon degeneracy, amino acid similarity, reading frame positioning, and the like.

For example, conservative amino acid substitutions may be made at one or more nonessential amino acid residues. A "nonessential" amino acid residue is a residue that can be altered from the reference sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or nonconserved alterations in the conserved residues.

Antibodies to the HPPD enzymes of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NO: 1-59 and 78-88 or a fragment thereof. In another embodiment, the antibody specifically binds to a fusion protein comprising an amino acid sequence selected from the amino acid sequence set forth in SEQ ID NO: 1-59 and 78-88, or a fragment thereof. In some embodiments, the antibody specifically binds to the region of the protein corresponding to amino acid position 178 of SEQ ID NO:1, or the region of the protein corresponding to amino acid position 188 of SEQ ID NO:1, or the region of the protein corresponding to amino acid position 200 of SEQ ID NO:1, or the region of the protein corresponding to amino acid position 226 of SEQ ID NO:1, or the region of the protein corresponding to amino acid positions 335-340 of SEQ ID NO:1. In other embodiments, the antibody specifically binds to the region of the protein corresponding to amino acid position 193 of SEQ ID NO: 59, or the region of the protein corresponding to amino acid position 209 of SEQ ID NO: 59, or the region of the protein corresponding to amino acid position 221 of SEQ ID NO: 59, or the region of the protein corresponding to amino acid position 247 of SEQ ID NO: 59, or the region of the protein corresponding to amino acid positions 351-356 of SEQ ID NO: 59.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

F. Gene Stacking

In the commercial production of crops, it is desirable to eliminate under reliable pesticidal management unwanted plants (i.e., "weeds") from a field of crop plants. An ideal treatment would be one which could be applied to an entire field but which would eliminate only the unwanted plants while leaving the crop plants unaffected. One such treatment system would involve the use of crop plants which are tolerant to an herbicide so that when the herbicide is sprayed on a field of herbicide-tolerant crop plants, the crop plants would continue to thrive while non-herbicide-tolerant weeds are killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

While a number of herbicide-tolerant crop plants are presently commercially available, an issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) *Weed Science* 50: 700-712; Owen and Zelaya (2005) *Pest Manag. Sci.* 61: 301-311). Transgenic plants which are tolerant to more than one herbicide have been described (see, e.g., WO2005/012515). However, improvements in every aspect of crop production, weed control options, extension of residual weed control, and improvement in crop yield are continuously in demand.

Silencing of the HPPD genes of the invention can be advantageously combined with expression of one or more HPPD protein or nucleotide sequences. In addition, HPPD silencing+HPPD expression is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides, according to their chemical structure, differ from HPPD inhibitor herbicides, and others which confer tolerance to certain insects, those which confer tolerance to certain diseases, DNAs that encodes RNAs that provide nematode or insect control, and the like.

Such genes are in particular described in published PCT Patent Applications WO91/02071 and WO95/06128 and in U.S. Pat. No. 7,923,602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769, 061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008, 547, 7,999,152, 7,998,703, 7,863,503, 7,714,188, 7,709,702, 7,666,644, 7,666,643, 7,531,339, 7,527,955, and 7,405, 074), or a gene encoding glyphosate oxidoreductase (for example, U.S. Pat. No. 5,463,175).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/ 074443), and which is described in application U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and genes encoding Dicamba monooxygenases conferring tolerance to dicamba (3,6-dichloro-2-methoxybenzoic acid) by metabolization (US 2008/0119361 and US 2008/0120739).

In various embodiments, the HPPD of the invention is stacked with one or more herbicide tolerant genes, including one or more additional HPPD inhibitor herbicide tolerant genes, and/or one or more genes tolerant to glyphosate and/or glufosinate. In one embodiment, the HPPD of the invention is combined with 2mEPSPS and bar.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326, 169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/ 47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from *Xenorhabdus* (as described in WO98/ 50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, the HPPD sequence of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYH-TOH2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYH-TOH2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDTO9Y (corn, ATCC Accession No PTA-13025, WO2013/012775A1).

G. Polynucleotide Constructs

The polynucleotides constructed to silence the HPPD genes of the present invention and/or encoding the HPPD polypeptides of the present invention may be modified to obtain or enhance expression in plant cells. The polynucleotides encoding the polypeptides identified herein may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e., promoter, particularly a heterologous promoter) operably-linked to one or more polynucleotides of interest, and/or a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

In a further embodiment, the present invention relates to a chimeric gene comprising a coding sequence comprising heterologous the nucleic acid of the invention operably linked to a plant-expressible promoter and optionally a transcription termination and polyadenylation region. "Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Nat. Acad. Sci. USA,* 76:760-764. Many suitable promoters for use in plants are well known in the art.

For instance, suitable constitutive promoters for use in plants include: the promoters from plant viruses, such as the peanut chlorotic streak caulimovirus (PCSV) promoter (U.S. Pat. No. 5,850,019); the 35S promoter from cauliflower mosaic virus (CaMV) (Odell et al. (1985) *Nature* 313:810-812); promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to silence the HPPD genes and/or express the HPPD proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PCSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639; and European Patent Application EP 0 633 317 A1.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science*, 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

H. Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods. See, for example, the methods for transforming plant cells and regenerating plants described in: U.S. Pat. Nos. 4,459,355, 4,536,475, 5,464,763, 5,177,010, 5,187,073, EP 267,159 A1, EP 604 662 A1, EP 672 752 A1, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174 A1, EP 486 233 A1, EP 486 234 A1, EP 539 563 A1, EP 674 725 A1, WO91/02071, WO95/06128, and WO2011/095460, each of which is herein incorporated by reference, particularly with respect to the transformation methods described therein.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The plant cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome. In various embodiments, the seed can be coated with at least one fungicide and/or at least one insecticide, at least one herbicide, and/or at least one safener, or any combination thereof.

I. Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}$P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by nucleotide sequences of the invention is then tested by hybridizing the filter to a radioactive probe derived from a GDC by methods known in the art (Sambrook and Russell (2001) supra). RNA can also be detected and/or quantified using reverse transcriptase PCR as known in the art (e.g., Green and Sambrook (2012) Molecular Cloning: A Laboratory Manual, 4$^{th}$ Edition, Cold Spring Harbor Laboratory Press, Woodbury, N.Y.).

Western blot, ELISA, lateral flow testing, and biochemical assays and the like may be carried out on the transgenic plants to determine the presence of protein encoded by the herbicide tolerance gene by standard procedures (Sambrook and Russell (2001) supra) using antibodies that bind to one or more epitopes present on the herbicide tolerance protein.

In one aspect of the invention, the HPPD genes described herein are useful as markers to assess transformation of bacterial or plant cells.

J. Use as a Marker for Transformation

The invention also relates to the use, in a method for transforming plants, of a nucleic acid which encodes an HPPD according to the invention as a marker gene or as a coding sequence which makes it possible to confer to the plant tolerance to herbicides which are HPPD inhibitors, and the use of one or more HPPD inhibitor(s) on plants comprising a nucleic acid sequence encoding a HPPD according to the invention. See, for example, U.S. Pat. No. 6,791,014, which is herein incorporated by reference in its entirety.

In this embodiment, an HPPD inhibitor can be introduced into the culture medium of the competent plant cells so as to bleach said cells before the transformation step. The bleached competent cells are then transformed with the gene for tolerance to HPPD inhibitors, as a selection marker, and the transformed cells which have integrated said selection marker into their genome become green, enabling them to be selected. Such a process makes it possible to decrease the time required for selecting the transformed cells.

Thus, one embodiment of the present invention consists of a method for transforming plant cells by introducing a heterologous gene into said plant cells with a gene for tolerance to HPPD inhibitors as selection markers, wherein the method comprises preparing and culturing competent plant cells capable of receiving the heterologous gene in a suitable medium and introducing a suitable amount of HPPD inhibitor into the suitable culture medium of the competent plant cells. The competent cells are then transformed with the heterologous gene and the selection marker, and the transformed cells comprising the heterologous gene are grown in a suitable medium and transformants selected therefrom. The transformed cells can then be regenerated into a fertile transformed plant.

K. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Crop plants are also of interest, including, for example, maize, sorghum, wheat, sunflower, tomato, crucifers, peppers, potato, cotton, rice, soybean, sugarbeet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

L. Methods for Increasing Plant Yield

Methods for increasing plant yield are provided. The methods comprise providing a plant comprising, or introducing into a plant or plant cell, a polynucleotide comprising a nucleotide sequence silencing an HPPD gene of the invention and/or encoding an HPPD of the invention, growing the plant or a seed thereof in a field, and producing a harvest from said plants or seeds. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant comprising an HPPD-silencing sequence and/or HPPD sequence of the invention is treated with an effective concentration of an HPPD inhibitor herbicide, such as one or more HPPD inhibitor herbicide(s) selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, where the herbicide application results in enhanced plant yield.

Methods for conferring herbicide tolerance in a plant or plant part are also provided. In such methods, a nucleotide sequence silencing an HPPD gene of the invention and/or encoding an HPPD of the invention is introduced into the plant, wherein expression of the polynucleotide results in HPPD inhibitor herbicide tolerance. Plants produced via this method can be treated with an effective concentration of an herbicide (such as one or more HPPD inhibitor herbicide(s) selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl) benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) and display an increased tolerance to the herbicide. An "effective concentration" of an herbicide in this application is an amount sufficient to slow or stop the growth of plants or plant parts that are not naturally tolerant or rendered tolerant to the herbicide.

M. Methods of Controlling Weeds in Afield

The present invention therefore also relates to a method of controlling undesired plants or for regulating the growth of plants in crops of plants comprising a nucleotide sequence silencing an HPPD gene according to the invention and/or encoding an HPPD according to the invention, where one or more HPPD inhibitor herbicides, for example, one or more HPPD inhibitor herbicides selected from the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, an effective concentration of one or more HPPD inhibitor herbicide(s), for example, one or more HPPD inhibitor herbicides selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl) benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, the class of isoxazoles preferably such as isoxaflutole, or of the class of pyrazolinates, preferably such as pyrasulfotole and topramezone, particularly selected from tembotrione, sulcotrione, topramezone, bicyclopyrone, tefuryltrione, isoxaflutole, and mesotrione, can be applied for example pre-planting (if appropriate also by incorporation into the soil), pre-emergence or post-emergence, and may be combined with the application of other herbicides to which the crop is naturally tolerant, or to which it is resistant via expression of one or more other herbicide resistance transgenes. See, e.g., U.S. App. Pub. No. 2004/0058427 and PCT App. Pub. No. WO98/20144. By "effective concentration" is intended the concentration which controls the growth or spread of weeds or other untransformed plants without significantly affecting the HPPD inhibitor-tolerant plant or plant seed. Those of skill in the art understand that application of herbicides can take many different forms and can take place at many different times prior to and/or throughout the seed planting and growth process. "Pre-emergent" application refers to an herbicide which is applied to an area of interest (e.g., a field or area of cultivation) before a plant emerges visibly from the soil. "Post-emergent" application refers to an herbicide which is applied to an area after a plant emerges visibly from the soil. In some instances, the terms "pre-emergent" and "post-emergent" are used with reference to a weed in an area of interest, and in some instances these terms are used with reference to a crop plant in an area of interest. When used with reference to a weed, these terms may apply to a particular type of weed or species of weed that is present or believed to be present in the area of interest. "Pre-plant incorporation" of an herbicide involves the incorporation of compounds into the soil prior to planting.

Thus, the present invention comprises a method of controlling weeds in a field comprising planting in a field a plant or a seed thereof in which one or more HPPD genes are silenced, optionally comprising an HPPD of the invention and applying to said plant or area surrounding said plant an effective concentration of one or more HPPD inhibitor herbicides.

In one embodiment of this invention, a field to be planted with plants (such as soybean, cotton, corn, or wheat plants, e.g.) containing an HPPD nucleotide sequence of the invention, can be treated with an HPPD inhibitor herbicide, such as isoxaflutole (IFT), before the plants are planted or the seeds are sown, which cleans the field of weeds that are killed by the HPPD inhibitor, allowing for no-till practices, followed by planting or sowing of the plants in that same pre-treated field later on (burndown application using an HPPD inhibitor herbicide). The residual activity of IFT will also protect the emerging and growing plants from competition by weeds in the early growth stages. Once the plants have a certain size, and weeds tend to re-appear, glufosinate or glyphosate, or an HPPD inhibitor or a mixture of an HPPD inhibitor with another herbicide such as glyphosate, can be applied as post-emergent herbicide over the top of the plants, when such plants are tolerant to said herbicides.

In another embodiment of this invention, a field in which seeds containing an HPPD nucleotide sequence of the invention were sown, can be treated with an HPPD inhibitor herbicide, such as IFT, before the plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing plants have no competition by weeds (pre-emergence application of an HPPD inhibitor herbicide). Once the plants have a certain size, and weeds tend to re-appear, glufosinate or glyphosate, or an HPPD inhibitor or a mixture of an HPPD inhibitor with another herbicide such as glyphosate, can be applied as post-emergent herbicide over the top of the plants, when such plants are tolerant to said herbicides.

In another embodiment of this invention, plants containing an HPPD nucleotide sequence of the invention, can be treated with an HPPD inhibitor herbicide, over the top of the plants that have emerged from the seeds that were sown, which cleans the field of weeds killed by the HPPD inhibitor, which application can be together with (e.g., in a spray tank mix), followed by or preceded by a treatment with glyphosate or glufosinate as post-emergent herbicide over the top of the plants (post-emergence application of an HPPD inhibitor herbicide (with or without glyphosate)), when such plants are tolerant to such herbicides.

Examples of individual representatives of the monocotyledonous and dicotyledonous weeds which can be controlled with an HPPD inhibitor herbicide include:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

HPPD inhibitor herbicides useful in the present invention, including but not limited to HPPD inhibitor herbicides of the class of N (1,2,5-oxadiazol-3-yl)benzamides; N-(tetrazol-4-yl)- or N-(triazol-3-yl)arylcarboxamides, such as 2-chloro-3-ethoxy-4-(methylsulfonyl)-N-(1-methyl-1H-tetrazol-5-yl) benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Interface-active ethylene oxide adducts], Wiss. Verlagsgesell, Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

N. Methods of Introducing Gene of the Invention into Another Plant

Also provided herein are methods of introducing the HPPD nucleotide sequence of the invention into another plant. The HPPD nucleotide sequence of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising an HPPD-silencing and/or HPPD nucleotide sequence of the invention with a second plant to produce F1 progeny plants and selecting F1 progeny plants that are tolerant to an HPPD inhibitor herbicide or that comprise the HPPD-silencing and/or HPPD nucleotide sequence of the invention. The methods may further comprise crossing the selected progeny plants with the first plant comprising the HPPD-silencing and/or HPPD nucleotide sequence of the invention to produce backcross progeny plants and selecting backcross progeny plants that are tolerant to an HPPD inhibitor herbicide or that comprise the HPPD-silencing and/or HPPD nucleotide sequence of the invention. Methods for evaluating HPPD inhibitor herbicide tolerance are provided elsewhere herein. The methods may further comprise repeating these steps one or more times in succession to produce selected second or higher backcross progeny plants that are tolerant to an HPPD inhibitor herbicide or that comprise the HPPD-silencing and/or HPPD nucleotide sequence of the invention.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., HPPD inhibitor herbicide tolerance) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc.).

O. Methods of Obtaining a Plant Product

The present invention also relates to a process for obtaining a commodity product, comprising harvesting and/or milling the grains from a crop comprising an HPPD sequence of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL

Example 1

To determine whether a heterologous HPPD gene could fully substitute the soybean endogenous HPPD (SEQ ID NO: 89) in genetically modified (GM) events, a bacterial Pf-HPPD mutant, e.g., recombinant Pf-HPPD-evo41 (SEQ ID NO: 16), and a RNAi construct inhibiting the expression of endogenous HPPD-Gm gene were used to transform soybean plant cells.

FIG. 2 shows an alignment of the amino acid between Pf-HPPD (SEQ ID NO: 1) (Query) and Pf-HPPD-evo41 (Sbjct). Pf-HPPD-evo41 (SEQ ID NO:16) has a proline at the amino acid position corresponding to amino acid position 335, a tryptophan at the amino acid position corresponding to amino acid position 336, an alanine at the amino acid position corresponding to amino acid position 339, and a glutamine at the amino acid position corresponding to amino acid position 340 of Pf-HPPD (SEQ ID NO:1).

FIG. 3 shows a DNA construct, e.g., pCPE826, used for expressing Pf-HPPD-evo41 and simultaneously inhibiting the expression of the endogenous HPPD (HPPD-Gm) in soybean. pCPE826 includes a DNA coding sequence for Pf-HPPD-evo41 driven by a Cassava vein mosaic virus promoter (CsVMV) and a RNAi (hairpin) cassette designed to silence the endogenous soybean HPPD (HPPD-Gm). RNAi cassette includes an RNAi insert as operably linked components: (i) a sense polynucleotide strand comprising at least 20 contiguous nucleotides from the sequence as set forth in SEQ ID NO: 89 operably linked to the *Arabidopsis* histone H4 promoter (Ph4A748abc) in the sense orientation, (ii) a spacer sequence, e.g., intron 1 (SEQ ID NO: 94) of HPPD-Gm, (iii) the polynucleotide strand of (i) in the anti-sense orientation, and (iv) a transcription terminator sequence.

Figure 4:
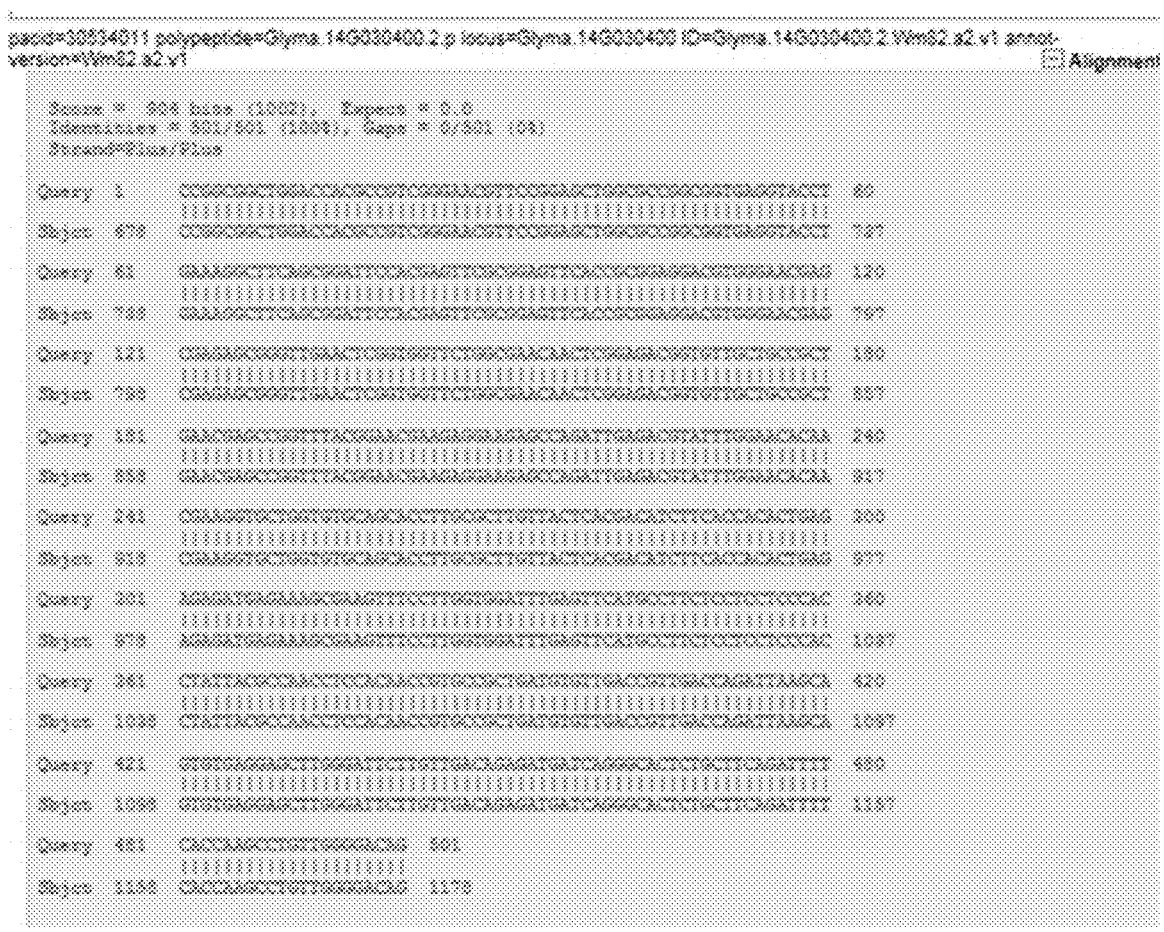
FIG. 4 shows an alignment of an RNAi insert having the nucleotide sequence of SEQ ID NO: 91 and that of a 501-nucleotide sequence corresponding to 678-1178 nucleotides of endogenous soybean HPPD (glyma14g030400) (SEQ ID NO: 89).

FIG. 4 shows an alignment of an RNAi insert having the nucleotide sequence of SEQ ID NO: 91 and that of a 501-nucleotide sequence corresponding to 678-1178 nucleotides of endogenous soybean HPPD (glyma14g030400) (SEQ ID NO: 89) encoding HPPD protein having the amino acid sequence of SEQ ID NO: 92. The nucleotide sequence of SEQ ID NO: 91 used in RNAi cassette of pCPE826 is 100% identical to 678-1178 nucleotides of endogenous soybean HPPD (SEQ ID NO: 89) such that RNA transcribed from the sense and anti-sense strands hybridize to form a hairpin structure that functions as a microRNA targeting HPPD-Gm mRNA (SEQ ID NO: 89) to inhibit the expression of endogenous HPPD-Gm.

Figure 5:
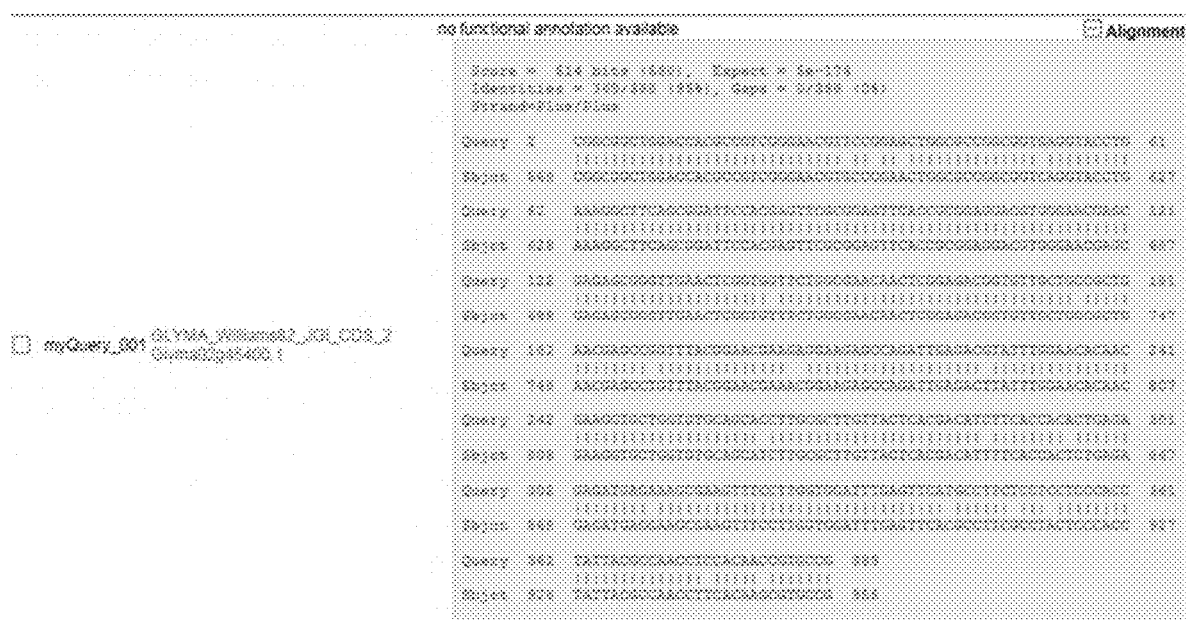
FIG. 5 shows an alignment of an RNAi insert having the nucleotide sequence (2-389) of SEQ ID NO: 91 and 568-955 nucleotides of a second gene, i.e., glyma02g45400 (SEQ ID NO: 90), on chromosome 2 in soybean.

FIG. 5 shows an alignment of an RNAi insert having the nucleotide sequence (2-389) of SEQ ID NO: 91 and 568-955 nucleotides of a second gene, i.e., glyma02g45400 (SEQ ID NO: 90) encoding HPPD protein having the amino acid sequence of SEQ ID NO: 93, on chromosome 2 in soybean. Glyma02g45400 is highly homologous (about 95% identity)

to endogenous soybean HPPD (HPPD-Gm) (SEQ ID NO: 89). According to RNAseq public data, this glyma02g45400 gene (SEQ ID NO: 90) is, in theory, not expressed at the same levels as the endogenous HPPD (HPPD-Gm) (SEQ ID NO: 89). It is possible that, if the endogenous HPPD is silenced, glyma02g45400 may also be silenced.

Generation of Transgenic Events and Herbicide Evaluation in T0 Lines

T0 events were generated by transforming soybean plant cells with pCPE826 (FIG. 3) using Tembotrione as selection marker. All T0 events had a normal phenotype.

To evaluate tolerance to herbicide, sixty-one single copy events were sprayed in the greenhouse with the HPPD inhibitor NOC115 (an HPPD inhibitor compound obtained from Bayer CropScience)

TABLE 1

| Construct | Promoter | GOI |
| --- | --- | --- |
| pCPE826 | CsVMV/PhA748abc | Pf-evo41/HPPD-Gm RNAi |
| pJPL0046 | CsVMV | Pf-evo41 |
| pBay00711 | CsVMV/Ph4A748abc | Pf-evo41 |

Figure 6:
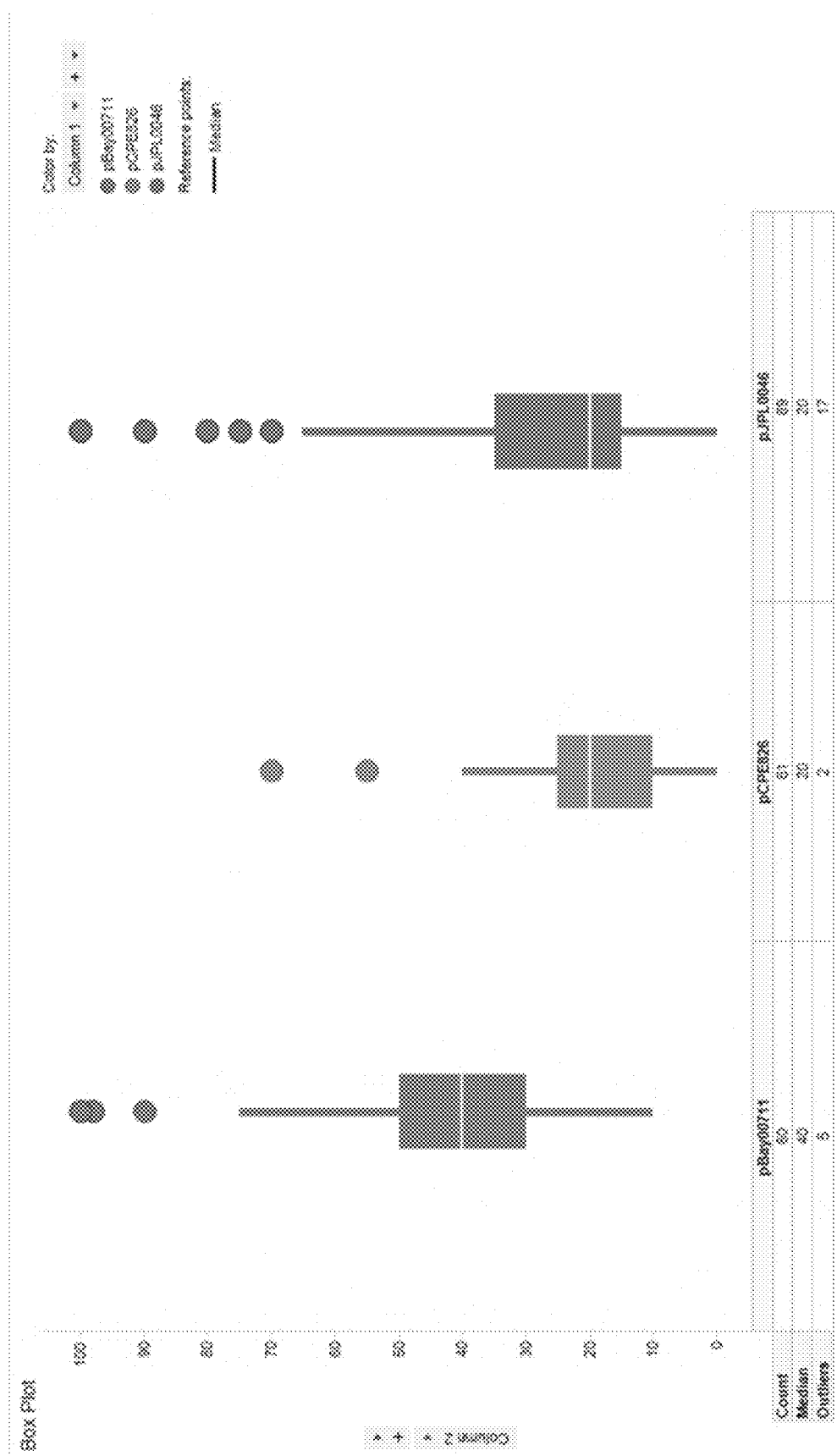
FIG. 6 shows one embodiment of the present disclosure.

FIG. 6 shows the median damage rating for the pCPE826 soybean transformants is about 20, which is better than that of the pBay00711 transformants, i.e., about 40. As shown in Table 1, pBay00711 and pCPE826 each express a single Pf-HPPD-evo41 construct driven by the promoter CsVMV/PhA748abc. The difference between these two constructs includes that pCPE826 expresses the RNAi, i.e., HPPD-Gm RNAi, and pBay00711 does not. Thus, silencing of the putative HPPD genes accounts for a significant increase in tolerance to NOC115.

Similar results are seen when comparing the pCPE826 transformants with soybean plants transformed with a single Pf-HPPD-evo41 construct without the RNAi cassette driven by a different promoter (CsVMV) from pCPE826 and pBay00711 (pJPL0046; Table 1). Although the median damage rating for pJPL0046 transformants is similar to the median damage rating for pCPE826 transformants, several pJPL0046 transformants displayed increased damage when exposed to NOC115, whereas pCPE826 transformants rarely displayed a damage rating higher than 40 (see FIG. 6).

The above T0 data shows a significant improvement in tolerance to HPPD inhibitor pesticide, e.g., NOC115, by inhibiting expression of two HPPD genes.

Figure 7:
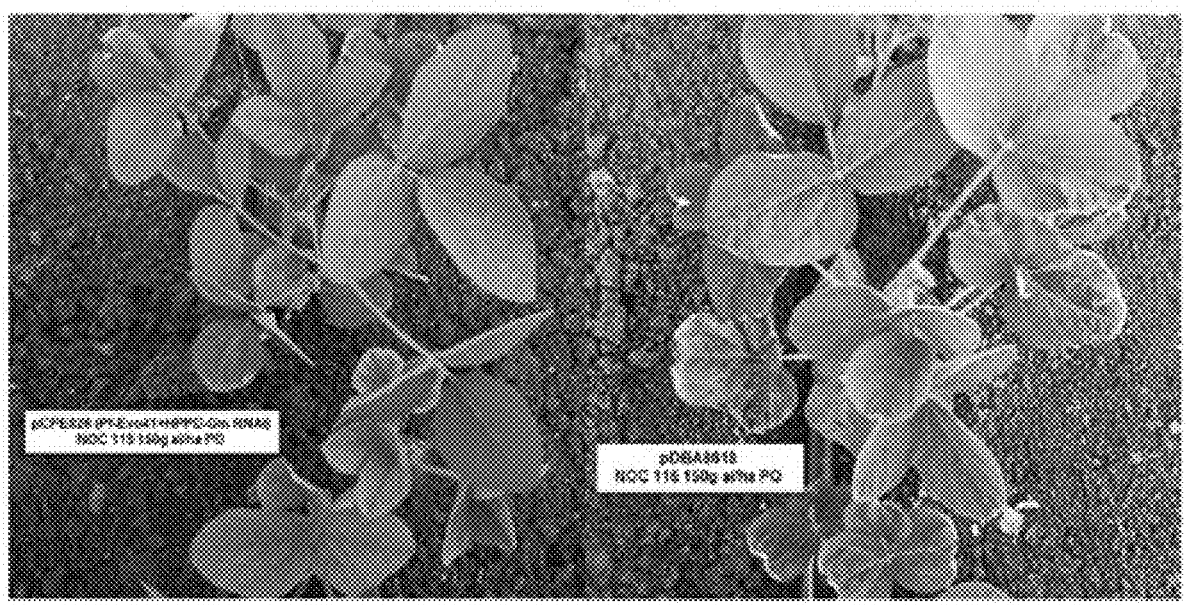
FIG. 7 shows another embodiment of the present disclosure.

The above result was confirmed in a field trial of the T1 generation. Of the constructs tested in Puerto Rico, pMLS0519 (Pf-KGEPHSVV), which is a single cassette construct encoding a variant of *Pseudomonas* HPPD that is more tolerant to HPPD inhibitors, such as NOC115, and pCPE826 (Pf-Evo41+HPPD-Gm RNAi) were the most effective in providing good tolerance to NOC115 and Isoxaflutole (IFT), which is a commercially available HPPD inhibitor compound. Consistently, as shown in FIG. 7, soybean plants transformed by pCPE826 (left panel) had better tolerance to NOC115 than that transformed by the control construct, e.g., pDBA8618 THT, which has the same *Pseudomonas* HPPD expression cassette as pJPL0046 (right panel).

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for conferring tolerance to a 4-hydroxyphenylpyruvate dioxygenase (HPPD) inhibitor herbicide in a plant, comprising reducing expression of at least one endogenous HPPD enzyme in the plant, wherein the method further comprises expressing a mutant HPPD enzyme, wherein the mutant HPPD enzyme is less sensitive to HPPD inhibitors than the corresponding native HPPD enzyme before mutation.

2. The method according to claim 1, wherein the mutant HPPD enzyme has the amino acid sequence of SEQ ID NO: 1 with the following amino acid substitutions:
   (a) a proline at the amino acid position corresponding to amino acid position 335 of SEQ ID NO:1 and a tryptophan at the amino acid position corresponding to amino acid position 336 of SEQ ID NO:1;
   (b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;
   (c) a tryptophan at the amino acid position corresponding to amino acid position 188 of SEQ ID NO:1 and a tryptophan at the amino acid position corresponding to amino acid position 336 of SEQ ID NO:1;
   (d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1; or
   (e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1.

3. The method according to claim 2, wherein the mutant HPPD enzyme has the amino acid sequence of SEQ ID NO: 16.

4. The method according to claim 1, wherein the expression of at least one HPPD enzyme in the plant is reduced by silencing one or more endogenous HPPD genes in the plant.

5. The method according to claim 1, wherein the plant is selected from the group consisting of: maize, sorghum, wheat, sunflower, tomato, crucifers, peppers, potato, cotton, rice, soybean, sugarbeet, sugarcane, tobacco, barley, and oilseed rape.

6. The method according to claim 1, wherein the plant is soybean.

7. The method according to claim 6, wherein the HPPD enzyme is encoded by a nucleic acid having the nucleotide sequence of SEQ ID NO: 89 and/or SEQ ID NO: 90.

8. The method according to claim 6, wherein the method comprises:
  (a) transforming a soybean cell with a DNA construct comprising a RNAi region for inhibiting the expression of one or more endogenous HPPD genes; and
  (b) regenerating a transgenic soybean plant from said transformed soybean cell.

9. The method according to claim 8, wherein the DNA construct comprising a RNAi region for inhibiting the expression of one or more endogenous HPPD genes further comprises a coding region that encodes a mutant HPPD enzyme, wherein the mutant HPPD enzyme mutant is less sensitive to HPPD inhibitors than the native HPPD enzyme before mutation.

10. The method according to claim 9, wherein the mutant HPPD enzyme has the amino acid sequence of SEQ ID NO:1 with the following amino acid substitutions:
  (a) a proline at the amino acid position corresponding to amino acid position 335 of SEQ ID NO:1 and a tryptophan at the amino acid position corresponding to amino acid position 336 of SEQ ID NO:1;
  (b) a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1;
  (c) a tryptophan at the amino acid position corresponding to amino acid position 188 of SEQ ID NO:1 and a tryptophan at the amino acid position corresponding to amino acid position 336 of SEQ ID NO:1;
  (d) a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1; or
  (e) a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1.

11. The method according to claim 9, wherein the coding region encodes the amino acid sequence set forth in any of SEQ ID NOs: 3-59 or fragments thereof.

12. The method according to claim 9, wherein the coding region encodes the amino acid sequence set forth in SEQ ID NO: 16 or fragments thereof.

13. The method according to claim 9, wherein the coding region is a synthetic sequence that has been designed for expression in soybean.

14. A transgenic soybean plant produced by the method of claim 8.

* * * * *

SEQUENCE LISTING

```
<160> NUMBER OF SEQ ID NOS: 94

<210> SEQ ID NO 1
<211> LENGTH: 358
<212> TYPE: PRT
<213> ORGANISM: Pseudomonas fluorescens

<400> SEQUENCE: 1

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
            115                 120                 125
```

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 2
<211> LENGTH: 358
<212> TYPE: PRT
<213> ORGANISM: Artificial Sequence
<220> FEATURE:
<223> OTHER INFORMATION: HPPD mutant - PfG336W

<400> SEQUENCE: 2

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 3
<211> LENGTH: 358
<212> TYPE: PRT
<213> ORGANISM: Artificial Sequence
<220> FEATURE:
<223> OTHER INFORMATION: HPPD mutant - PfHPPDEvo37

<400> SEQUENCE: 3

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Trp Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 4
<211> LENGTH: 358
<212> TYPE: PRT
<213> ORGANISM: Artificial Sequence
<220> FEATURE:
<223> OTHER INFORMATION: HPPD mutant - C0234E6

<400> SEQUENCE: 4

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
           130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 5
<211> LENGTH: 358
<212> TYPE: PRT
<213> ORGANISM: Artificial Sequence
<220> FEATURE:
<223> OTHER INFORMATION: HPPD mutant - C024H11

<400> SEQUENCE: 5

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 6
<211> LENGTH: 358
<212> TYPE: PRT
<213> ORGANISM: Artificial Sequence
<220> FEATURE:
<223> OTHER INFORMATION: HPPD mutant - PfHPPDEvo33

<400> SEQUENCE: 6

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 7
<211> LENGTH: 358
<212> TYPE: PRT
<213> ORGANISM: Artificial Sequence
<220> FEATURE:
<223> OTHER INFORMATION: HPPD mutant - PfHPPDEvo36

<400> SEQUENCE: 7

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Thr Gln Leu Phe Glu Ser Ile Glu Arg Asp Gln Val Arg Arg
            340                 345                 350

Gly Val Leu Thr Ala Asp
        355

<210> SEQ ID NO 8
<211> LENGTH: 358
<212> TYPE: PRT
<213> ORGANISM: Artificial Sequence
<220> FEATURE:
<223> OTHER INFORMATION: HPPD mutant - PfHPPDEvo40

<400> SEQUENCE: 8

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
              130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                    165                 170                 175

Asn Phe Tyr Glu Lys Leu Phe Asn Phe Arg Glu Ala Arg Tyr Phe Asp
                180                 185                 190

Ile Lys Gly Glu Tyr Thr Gly Leu Thr Ser Lys Ala Met Ser Ala Pro
            195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Lys Glu Leu Phe Glu Ser Ile Glu Arg Asp Gln Val Arg Arg
                340                 345                 350

Gly Val Leu Thr Ala Asp
            355

<210> SEQ ID NO 9
<211> LENGTH: 358
<212> TYPE: PRT
<213> ORGANISM: Artificial Sequence
<220> FEATURE:
<223> OTHER INFORMATION: HPPD mutant - CO210d10

<400> SEQUENCE: 9

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Thr Ala Leu Phe Glu Ser Ile Glu Arg Asp Gln Val Arg Arg
            340                 345                 350

Gly Val Leu Thr Ala Asp
        355

<210> SEQ ID NO 10
<211> LENGTH: 358
<212> TYPE: PRT
<213> ORGANISM: Artificial Sequence
<220> FEATURE:
<223> OTHER INFORMATION: HPPD mutant - CO212f3

<400> SEQUENCE: 10

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
            245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Trp
            325                 330                 335

Asn Phe Lys Val Leu Phe Glu Ser Ile Glu Arg Asp Gln Val Arg Arg
            340                 345                 350

Gly Val Leu Thr Ala Asp
        355

<210> SEQ ID NO 11
<211> LENGTH: 358
<212> TYPE: PRT
<213> ORGANISM: Artificial Sequence
<220> FEATURE:
<223> OTHER INFORMATION: HPPD mutant - C644

<400> SEQUENCE: 11

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
            85                  90                  95

Glu Leu Gly Ala Gln Pro Ile His Ile Asp Thr Gly Pro Met Glu Leu
        100                 105                 110

Asn Leu Pro Ala Ile Lys Gly Ile Gly Gly Ala Pro Leu Tyr Leu Ile
    115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ile Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 12
<211> LENGTH: 358
<212> TYPE: PRT
<213> ORGANISM: Artificial Sequence
<220> FEATURE:
<223> OTHER INFORMATION: HPPD mutant - C645

<400> SEQUENCE: 12

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
        130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Ala Arg Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Glu Ser Ser Lys Gly Ala
    210                 215                 220
Gly Gln Ile Glu Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
    290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Ile Gly
                325                 330                 335
Asn Phe Lys Ala Leu Phe Glu Ser Ile Glu Arg Asp Gln Val Arg Arg
            340                 345                 350
Gly Val Leu Thr Ala Asp
        355

<210> SEQ ID NO 13
<211> LENGTH: 358
<212> TYPE: PRT
<213> ORGANISM: Artificial Sequence
<220> FEATURE:
<223> OTHER INFORMATION: HPPD mutant - c0218A5

<400> SEQUENCE: 13

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
            20                  25                  30
Ile Met Gly Phe Thr Lys Val Ala Thr His Arg Ser Lys Asn Val His
        35                  40                  45
Leu Tyr Arg Gln Gly Glu Ile Asn Leu Ile Leu Asn Asn Glu Pro Asn
    50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Ala Ala Leu Phe Glu Ser Ile Glu Arg Asp Gln Val Arg Arg
            340                 345                 350

Gly Val Leu Thr Ala Asp
        355

<210> SEQ ID NO 14
<211> LENGTH: 358
<212> TYPE: PRT
<213> ORGANISM: Artificial Sequence
<220> FEATURE:
<223> OTHER INFORMATION: HPPD mutant - C0216C6

<400> SEQUENCE: 14

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Thr Ala Leu Phe Glu Ser Ile Glu Arg Asp Gln Val Arg Arg
            340                 345                 350

Gly Val Leu Thr Ala Asp
        355

<210> SEQ ID NO 15
<211> LENGTH: 358
<212> TYPE: PRT
<213> ORGANISM: Artificial Sequence
<220> FEATURE:
<223> OTHER INFORMATION: HPPD mutant - c0213H10

<400> SEQUENCE: 15

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly His Trp
                325                 330                 335

Asn Phe Thr Gln Leu Phe Glu Ser Ile Glu Arg Asp Gln Val Arg Arg
            340                 345                 350

Gly Val Leu Thr Ala Asp
        355

<210> SEQ ID NO 16
<211> LENGTH: 358
<212> TYPE: PRT
<213> ORGANISM: Artificial Sequence
<220> FEATURE:
<223> OTHER INFORMATION: HPPD mutant - PfHPPDEvo41

<400> SEQUENCE: 16

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Ala Arg Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Ser Ser Lys Gly Ala
    210                 215                 220
Gly Gln Ile Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
    290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Trp
                325                 330                 335
Asn Phe Ala Gln Leu Phe Glu Ser Ile Glu Arg Asp Gln Val Arg Arg
            340                 345                 350
Gly Val Leu Thr Ala Asp
        355

<210> SEQ ID NO 17
<211> LENGTH: 358
<212> TYPE: PRT
<213> ORGANISM: Artificial Sequence
<220> FEATURE:
<223> OTHER INFORMATION: HPPD mutant - C0228G9

<400> SEQUENCE: 17

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
                20                  25                  30
Ile Met Gly Phe Thr Lys Val Ala Thr His Arg Ser Lys Asn Val His
            35                  40                  45
Leu Tyr Arg Gln Gly Glu Ile Asn Leu Ile Leu Asn Asn Glu Pro Asn
        50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Ile Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
            355

<210> SEQ ID NO 18
<211> LENGTH: 358
<212> TYPE: PRT
<213> ORGANISM: Artificial Sequence
<220> FEATURE:
<223> OTHER INFORMATION: HPPD mutant - C0232D2

<400> SEQUENCE: 18

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Trp Ser Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 19
<211> LENGTH: 358
<212> TYPE: PRT
<213> ORGANISM: Artificial Sequence
<220> FEATURE:
<223> OTHER INFORMATION: HPPD mutant - C0234A4

<400> SEQUENCE: 19

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ala Trp
                325                 330                 335

Asn Phe Ser Gln Leu Phe Glu Ser Ile Glu Arg Asp Gln Val Arg Arg
            340                 345                 350

Gly Val Leu Thr Ala Asp
        355

<210> SEQ ID NO 20
<211> LENGTH: 358
<212> TYPE: PRT
<213> ORGANISM: Artificial Sequence
<220> FEATURE:
<223> OTHER INFORMATION: HPPD mutant - C0235F6

<400> SEQUENCE: 20

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ala Ser
                325                 330                 335

Asn Phe Ser Gln Leu Phe Glu Ser Ile Glu Arg Asp Gln Val Arg Arg
            340                 345                 350

Gly Val Leu Thr Ala Asp
        355

<210> SEQ ID NO 21
<211> LENGTH: 358
<212> TYPE: PRT
<213> ORGANISM: Artificial Sequence
<220> FEATURE:
<223> OTHER INFORMATION: HPPD mutant - C0235E2

<400> SEQUENCE: 21

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Ser Gln Leu Phe Glu Ser Ile Glu Arg Asp Gln Val Arg Arg
            340                 345                 350

Gly Val Leu Thr Ala Asp
        355

<210> SEQ ID NO 22
<211> LENGTH: 358
<212> TYPE: PRT
<213> ORGANISM: Artificial Sequence
<220> FEATURE:
<223> OTHER INFORMATION: HPPD mutant - C0236H7

<400> SEQUENCE: 22

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Trp
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 23
<211> LENGTH: 358
<212> TYPE: PRT
<213> ORGANISM: Artificial Sequence
<220> FEATURE:
<223> OTHER INFORMATION: HPPD mutant - C0236F8

<400> SEQUENCE: 23

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ala Ser
                325                 330                 335

Asn Phe Thr Gln Leu Phe Glu Ser Ile Glu Arg Asp Gln Val Arg Arg
                340                 345                 350

Gly Val Leu Thr Ala Asp
        355

<210> SEQ ID NO 24
<211> LENGTH: 358
<212> TYPE: PRT
<213> ORGANISM: Artificial Sequence
<220> FEATURE:
<223> OTHER INFORMATION: HPPD mutant - C0240D2

<400> SEQUENCE: 24

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ala Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 25
<211> LENGTH: 358
<212> TYPE: PRT
<213> ORGANISM: Artificial Sequence
<220> FEATURE:
<223> OTHER INFORMATION: HPPD mutant - C0240D12

<400> SEQUENCE: 25

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Thr Glu Leu Phe Glu Ser Ile Glu Arg Asp Gln Val Arg Arg
            340                 345                 350

Gly Val Leu Thr Ala Asp
        355

<210> SEQ ID NO 26
<211> LENGTH: 358
<212> TYPE: PRT
<213> ORGANISM: Artificial Sequence
<220> FEATURE:
<223> OTHER INFORMATION: HPPD mutant - C0242D4

<400> SEQUENCE: 26

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Lys Gln Leu Phe Glu Ser Ile Glu Arg Asp Gln Val Arg Arg
            340                 345                 350

Gly Val Leu Thr Ala Asp
        355

<210> SEQ ID NO 27
<211> LENGTH: 358
<212> TYPE: PRT
<213> ORGANISM: Artificial Sequence
<220> FEATURE:
<223> OTHER INFORMATION: HPPD mutant - C0244A2

<400> SEQUENCE: 27

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Gly Cys Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Ser Ser Lys Gly Ala
210                 215                 220
Gly Gln Ile Glu Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Ser
                325                 330                 335
Asn Phe Lys Ala Leu Phe Glu Ser Ile Glu Arg Asp Gln Val Arg Arg
            340                 345                 350
Gly Val Leu Thr Ala Asp
        355

<210> SEQ ID NO 28
<211> LENGTH: 358
<212> TYPE: PRT
<213> ORGANISM: Artificial Sequence
<220> FEATURE:
<223> OTHER INFORMATION: HPPD mutant - C0244F5

<400> SEQUENCE: 28

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
                20                  25                  30
Ile Met Gly Phe Thr Lys Val Ala Thr His Arg Ser Lys Asn Val His
            35                  40                  45
Leu Tyr Arg Gln Gly Glu Ile Asn Leu Ile Leu Asn Asn Glu Pro Asn
        50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Arg Tyr Phe Asp
            180                 185                 190

Ile Lys Gly Glu Tyr Thr Gly Leu Thr Ser Lys Ala Met Ser Ala Pro
            195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Thr Ala Leu Phe Glu Ser Ile Glu Arg Asp Gln Val Arg Arg
            340                 345                 350

Gly Val Leu Thr Ala Asp
        355

<210> SEQ ID NO 29
<211> LENGTH: 358
<212> TYPE: PRT
<213> ORGANISM: Artificial Sequence
<220> FEATURE:
<223> OTHER INFORMATION: HPPD mutant - C0247B6

<400> SEQUENCE: 29

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Ser Arg Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Ser Ser Lys Gly Ala
    210                 215                 220
Gly Gln Ile Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
    290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Gln Ser
                325                 330                 335
Asn Phe Lys Glu Leu Phe Glu Ser Ile Glu Arg Asp Gln Val Arg Arg
            340                 345                 350
Gly Val Leu Thr Ala Asp
        355

<210> SEQ ID NO 30
<211> LENGTH: 358
<212> TYPE: PRT
<213> ORGANISM: Artificial Sequence
<220> FEATURE:
<223> OTHER INFORMATION: HPPD mutant - C0247H7

<400> SEQUENCE: 30

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
                20                  25                  30
Ile Met Gly Phe Thr Lys Val Ala Thr His Arg Ser Lys Asn Val His
            35                  40                  45
Leu Tyr Arg Gln Gly Glu Ile Asn Leu Ile Leu Asn Asn Glu Pro Asn
        50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Trp Ser Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Thr Glu Leu Phe Glu Ser Ile Glu Arg Asp Gln Val Arg Arg
            340                 345                 350

Gly Val Leu Thr Ala Asp
            355

<210> SEQ ID NO 31
<211> LENGTH: 358
<212> TYPE: PRT
<213> ORGANISM: Artificial Sequence
<220> FEATURE:
<223> OTHER INFORMATION: HPPD mutant - C0252F11

<400> SEQUENCE: 31

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Ser Cys Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Ser Ser Lys Gly Ala
    210                 215                 220
Gly Gln Ile Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
    290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Trp
                325                 330                 335
Asn Phe Thr Gln Leu Phe Glu Ser Ile Glu Arg Asp Gln Val Arg Arg
            340                 345                 350
Gly Val Leu Thr Ala Asp
        355

<210> SEQ ID NO 32
<211> LENGTH: 358
<212> TYPE: PRT
<213> ORGANISM: Artificial Sequence
<220> FEATURE:
<223> OTHER INFORMATION: HPPD mutant - C0255B12

<400> SEQUENCE: 32

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
                20                  25                  30
Ile Met Gly Phe Thr Lys Val Ala Thr His Arg Ser Lys Asn Val His
            35                  40                  45
Leu Tyr Arg Gln Gly Glu Ile Asn Leu Ile Leu Asn Asn Glu Pro Asn
        50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Trp Cys Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Ser Ser Lys Gly Ala
210                 215                 220
Gly Gln Ile Glu Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Ser
                325                 330                 335
Asn Phe Lys Gln Leu Phe Glu Ser Ile Glu Arg Asp Gln Val Arg Arg
            340                 345                 350
Gly Val Leu Thr Ala Asp
        355

<210> SEQ ID NO 33
<211> LENGTH: 358
<212> TYPE: PRT
<213> ORGANISM: Artificial Sequence
<220> FEATURE:
<223> OTHER INFORMATION: HPPD mutant - C0255C1

<400> SEQUENCE: 33

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
            20                  25                  30
Ile Met Gly Phe Thr Lys Val Ala Thr His Arg Ser Lys Asn Val His
        35                  40                  45
Leu Tyr Arg Gln Gly Glu Ile Asn Leu Ile Leu Asn Asn Glu Pro Asn
    50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Gly Cys Tyr Phe Asp
            180                 185                 190
Ile Lys Gly Glu Tyr Thr Gly Leu Thr Ser Lys Ala Met Ser Ala Pro
        195                 200                 205
Asp Gly Met Ile Arg Ile Pro Leu Asn Glu Ser Ser Lys Gly Ala
    210                 215                 220
Gly Gln Ile Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
            260                 265                 270
Glu Met Leu Glu Gly Arg Leu Pro Asp His Gly Glu Pro Val Asp Gln
        275                 280                 285
Leu Gln Ala Arg Gly Ile Leu Leu Asp Gly Ser Ser Val Glu Gly Asp
    290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Ser
                325                 330                 335
Asn Phe Thr Glu Leu Phe Glu Ser Ile Glu Arg Asp Gln Val Arg Arg
            340                 345                 350
Gly Val Leu Thr Ala Asp
        355

<210> SEQ ID NO 34
<211> LENGTH: 357
<212> TYPE: PRT
<213> ORGANISM: Artificial Sequence
<220> FEATURE:
<223> OTHER INFORMATION: HPPD mutant - C0255C3

<400> SEQUENCE: 34

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
            20                  25                  30
Ile Met Gly Phe Thr Lys Val Ala Thr His Arg Ser Lys Asn Val His
        35                  40                  45
Leu Tyr Arg Gln Gly Glu Ile Asn Leu Ile Leu Asn Asn Glu Pro Asn
    50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Glu Leu Phe Glu Ser Ile Glu Arg Asp Gln Val Arg Arg Gly
            340                 345                 350

Val Leu Thr Ala Asp
        355

<210> SEQ ID NO 35
<211> LENGTH: 358
<212> TYPE: PRT
<213> ORGANISM: Artificial Sequence
<220> FEATURE:
<223> OTHER INFORMATION: HPPD mutant - C0255E6

<400> SEQUENCE: 35

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ser Ser Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Thr Glu Leu Phe Glu Ser Ile Glu Arg Asp Gln Val Arg Arg
            340                 345                 350

Gly Val Leu Thr Ala Asp
        355

<210> SEQ ID NO 36
<211> LENGTH: 358
<212> TYPE: PRT
<213> ORGANISM: Artificial Sequence
<220> FEATURE:
<223> OTHER INFORMATION: HPPD mutant - C0255E10

<400> SEQUENCE: 36

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ser Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
    210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Thr Ala Leu Phe Glu Ser Ile Glu Arg Asp Gln Val Arg Arg
            340                 345                 350

Gly Val Leu Thr Ala Asp
        355

<210> SEQ ID NO 37
<211> LENGTH: 358
<212> TYPE: PRT
<213> ORGANISM: Artificial Sequence
<220> FEATURE:
<223> OTHER INFORMATION: HPPD mutant - C0256B1

<400> SEQUENCE: 37

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

```
Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Ser
                325                 330                 335

Asn Phe Thr Glu Leu Phe Glu Ser Ile Glu Arg Asp Gln Val Arg Arg
            340                 345                 350

Gly Val Leu Thr Ala Asp
            355

<210> SEQ ID NO 38
<211> LENGTH: 358
<212> TYPE: PRT
<213> ORGANISM: Artificial Sequence
<220> FEATURE:
<223> OTHER INFORMATION: HPPD mutant - C0256G11

<400> SEQUENCE: 38

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ser Ser Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
    210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Lys Gln Leu Phe Glu Ser Ile Glu Arg Asp Gln Val Arg Arg
            340                 345                 350

Gly Val Leu Thr Ala Asp
        355

<210> SEQ ID NO 39
<211> LENGTH: 358
<212> TYPE: PRT
<213> ORGANISM: Artificial Sequence
<220> FEATURE:
<223> OTHER INFORMATION: HPPD mutant - C0256H4

<400> SEQUENCE: 39

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Ser Glu Leu Phe Glu Ser Ile Glu Arg Asp Gln Val Arg Arg
            340                 345                 350

Gly Val Leu Thr Ala Asp
        355

<210> SEQ ID NO 40
<211> LENGTH: 358
<212> TYPE: PRT
<213> ORGANISM: Artificial Sequence
<220> FEATURE:
<223> OTHER INFORMATION: HPPD mutant - C0257C5

<400> SEQUENCE: 40

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Lys Gln Leu Phe Glu Ser Ile Glu Arg Asp Gln Val Arg Arg
            340                 345                 350

Gly Val Leu Thr Ala Asp
        355

<210> SEQ ID NO 41
<211> LENGTH: 358
<212> TYPE: PRT
<213> ORGANISM: Artificial Sequence
<220> FEATURE:
<223> OTHER INFORMATION: HPPD mutant - C0260E11

<400> SEQUENCE: 41

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Thr Glu Leu Phe Glu Ser Ile Glu Arg Asp Gln Val Arg Arg
            340                 345                 350

Gly Val Leu Thr Ala Asp
        355

<210> SEQ ID NO 42
<211> LENGTH: 358
<212> TYPE: PRT
<213> ORGANISM: Artificial Sequence
<220> FEATURE:
<223> OTHER INFORMATION: HPPD mutant - C0260C6

<400> SEQUENCE: 42

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ser Ser Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Thr Glu Leu Phe Glu Ser Ile Glu Arg Asp Gln Val Arg Arg
            340                 345                 350

Gly Val Leu Thr Ala Asp
        355

<210> SEQ ID NO 43
<211> LENGTH: 358
<212> TYPE: PRT
<213> ORGANISM: Artificial Sequence
<220> FEATURE:
<223> OTHER INFORMATION: HPPD mutant - C0262C4

<400> SEQUENCE: 43

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
                260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Gln Leu Phe Glu Ser Ile Glu Arg Asp Gln Val Arg Arg
            340                 345                 350

Gly Val Leu Thr Ala Asp
        355

<210> SEQ ID NO 44
<211> LENGTH: 358
<212> TYPE: PRT
<213> ORGANISM: Artificial Sequence
<220> FEATURE:
<223> OTHER INFORMATION: HPPD mutant - C0262F11

<400> SEQUENCE: 44

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Lys Gln Leu Phe Glu Ser Ile Glu Arg Asp Gln Val Arg Arg
            340                 345                 350

Gly Val Leu Thr Ala Asp
        355

<210> SEQ ID NO 45
<211> LENGTH: 358
<212> TYPE: PRT
<213> ORGANISM: Artificial Sequence
<220> FEATURE:
<223> OTHER INFORMATION: HPPD mutant - C0263B7

<400> SEQUENCE: 45

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Thr Gln Leu Phe Glu Ser Ile Glu Arg Asp Gln Val Arg Arg
            340                 345                 350

Gly Val Leu Thr Ala Asp
        355

<210> SEQ ID NO 46
<211> LENGTH: 358
<212> TYPE: PRT
<213> ORGANISM: Artificial Sequence
<220> FEATURE:
<223> OTHER INFORMATION: HPPD mutant - C0263G12

<400> SEQUENCE: 46

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Gln Trp
                325                 330                 335

Asn Phe Ser Glu Leu Phe Glu Ser Ile Glu Arg Asp Gln Val Arg Arg
            340                 345                 350

Gly Val Leu Thr Ala Asp
        355

<210> SEQ ID NO 47
<211> LENGTH: 358
<212> TYPE: PRT
<213> ORGANISM: Artificial Sequence
<220> FEATURE:
<223> OTHER INFORMATION: HPPD mutant - C0261H2

<400> SEQUENCE: 47

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Ser Ala Leu Phe Glu Ser Ile Glu Arg Asp Gln Val Arg Arg
            340                 345                 350

Gly Val Leu Thr Ala Asp
        355

<210> SEQ ID NO 48
<211> LENGTH: 358
<212> TYPE: PRT
<213> ORGANISM: Artificial Sequence
<220> FEATURE:
<223> OTHER INFORMATION: HPPD mutant - C0264G5

<400> SEQUENCE: 48

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

```
Asp Arg Phe Gly Glu Gly Ser Ser Ile Tyr Asp Ile Asp Phe Val Tyr
            130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Ser Arg Tyr Phe Asp
                180                 185                 190
Ile Lys Gly Glu Tyr Thr Gly Leu Thr Ser Lys Ala Met Ser Ala Pro
                195                 200                 205
Asp Gly Met Ile Arg Ile Pro Leu Asn Glu Ser Ser Lys Gly Ala
210                 215                 220
Gly Gln Ile Glu Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
                260                 265                 270
Glu Met Leu Glu Gly Arg Leu Pro Asp His Gly Glu Pro Val Asp Gln
                275                 280                 285
Leu Gln Ala Arg Gly Ile Leu Leu Asp Gly Ser Ser Val Glu Gly Asp
290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Gln Ser
                325                 330                 335
Asn Phe Thr Glu Leu Phe Glu Ser Ile Glu Arg Asp Gln Val Arg Arg
                340                 345                 350
Gly Val Leu Thr Ala Asp
        355

<210> SEQ ID NO 49
<211> LENGTH: 358
<212> TYPE: PRT
<213> ORGANISM: Artificial Sequence
<220> FEATURE:
<223> OTHER INFORMATION: HPPD mutant - C0264G7

<400> SEQUENCE: 49

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
                20                  25                  30
Ile Met Gly Phe Thr Lys Val Ala Thr His Arg Ser Lys Asn Val His
                35                  40                  45
Leu Tyr Arg Gln Gly Glu Ile Asn Leu Ile Leu Asn Asn Glu Pro Asn
                50                  55                  60
Ser Ile Ala Ser Tyr Phe Ala Ala Glu His Gly Pro Ser Val Cys Gly
65                  70                  75                  80
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
                100                 105                 110
Asn Leu Pro Ala Ile Lys Gly Ile Gly Gly Ala Pro Leu Tyr Leu Ile
                115                 120                 125
```

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ser Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Lys Gln Leu Phe Glu Ser Ile Glu Arg Asp Gln Val Arg Arg
            340                 345                 350

Gly Val Leu Thr Ala Asp
        355

<210> SEQ ID NO 50
<211> LENGTH: 358
<212> TYPE: PRT
<213> ORGANISM: Artificial Sequence
<220> FEATURE:
<223> OTHER INFORMATION: HPPD mutant - C0266A11

<400> SEQUENCE: 50

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Ser Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
210                 215                 220

Gly Gln Ile Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Thr Gln Leu Phe Glu Ser Ile Glu Arg Asp Gln Val Arg Arg
            340                 345                 350

Gly Val Leu Thr Ala Asp
        355

<210> SEQ ID NO 51
<211> LENGTH: 357
<212> TYPE: PRT
<213> ORGANISM: Artificial Sequence
<220> FEATURE:
<223> OTHER INFORMATION: HPPD mutant - Axmi305H-Evo40

<400> SEQUENCE: 51

Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
    130                 135                 140

Asp Val Asp Phe Glu Phe Ile Glu Gly Arg Ser Ala Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
        195                 200                 205

Arg Ala Met Thr Ala Pro Cys Gly Lys Ile Arg Ile Pro Ile Asn Glu
    210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Arg Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
                325                 330                 335

Pro Ser Asn Phe Lys Glu Leu Phe Glu Ser Ile Glu Glu Asp Gln Ile
            340                 345                 350

Arg Arg Gly Val Ile
        355

<210> SEQ ID NO 52
<211> LENGTH: 357
<212> TYPE: PRT
<213> ORGANISM: Artificial Sequence
<220> FEATURE:
<223> OTHER INFORMATION: HPPD mutant - Axmi305H-Evo41

<400> SEQUENCE: 52

Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
                130                 135                 140

Asp Val Asp Phe Glu Phe Ile Glu Gly Arg Ser Ala Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
                180                 185                 190

Glu Ile Arg Tyr Phe Asp Ile Glu Gly Lys Leu Thr Gly Leu Phe Ser
                195                 200                 205

Arg Ala Met Thr Ala Pro Cys Gly Lys Ile Arg Ile Pro Ile Asn Glu
                210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
                260                 265                 270

Asp Thr Tyr Tyr Glu Lys Val Asp Thr Arg Val Ala Gly His Gly Glu
                275                 280                 285

Pro Leu Glu Gln Leu Arg Glu Leu Asn Leu Leu Ile Asp Gly Ala Pro
                290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
                325                 330                 335

Pro Trp Asn Phe Ala Gln Leu Phe Glu Ser Ile Glu Glu Asp Gln Ile
                340                 345                 350

Arg Arg Gly Val Ile
        355

<210> SEQ ID NO 53
<211> LENGTH: 358
<212> TYPE: PRT
<213> ORGANISM: Artificial Sequence
<220> FEATURE:
<223> OTHER INFORMATION: HPPD mutant - Axmi305H-Evo40

<400> SEQUENCE: 53

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
                35                  40                  45

Leu Tyr Arg Gln Gly Ala Ile Asn Leu Ile Leu Asn Asn Glu Pro His
                50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Glu Thr Gly Pro Met Glu Leu
                100                 105                 110

Asn Leu Pro Ala Ile Lys Gly Ile Gly Gly Ala Pro Leu Tyr Leu Ile
                115                 120                 125

```
Asp Arg Phe Gly Glu Gly Ser Ser Ile Tyr Asp Ile Asp Phe Val Phe
    130                 135                 140

Leu Glu Gly Val Asp Arg Asn Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Gln Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ser Arg Gly Ile Leu Leu Asp Gly Ala Ser Asp Lys Glu Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Lys Glu Leu Phe Glu Ser Ile Glu Arg Asp Gln Val Arg Arg
            340                 345                 350

Gly Val Leu Ala Thr Glu
        355

<210> SEQ ID NO 54
<211> LENGTH: 358
<212> TYPE: PRT
<213> ORGANISM: Artificial Sequence
<220> FEATURE:
<223> OTHER INFORMATION: HPPD mutant - Axmi305H-Evo41

<400> SEQUENCE: 54

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Ala Ile Asn Leu Ile Leu Asn Asn Glu Pro His
    50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125
```

Asp Arg Phe Gly Glu Gly Ser Ser Ile Tyr Asp Ile Asp Phe Val Phe
130                 135                 140

Leu Glu Gly Val Asp Arg Asn Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Gln Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ser Arg Gly Ile Leu Leu Asp Gly Ala Ser Asp Lys Glu Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Ala Gln Leu Phe Glu Ser Ile Glu Arg Asp Gln Val Arg Arg
            340                 345                 350

Gly Val Leu Ala Thr Glu
        355

<210> SEQ ID NO 55
<211> LENGTH: 373
<212> TYPE: PRT
<213> ORGANISM: Artificial Sequence
<220> FEATURE:
<223> OTHER INFORMATION: HPPD mutant - Axmi305H-Evo40

<400> SEQUENCE: 55

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

```
Lys Gly Ile Gly Asp Ser Leu Ile Tyr Phe Ile Asp Lys Trp Arg Gly
        130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Val Lys Ser Lys
210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Ser
            340                 345                 350

Asn Phe Lys Glu Leu Phe Glu Thr Met Glu Leu Asp Gln Met Arg Arg
        355                 360                 365

Gly Val Leu Lys Thr
    370

<210> SEQ ID NO 56
<211> LENGTH: 373
<212> TYPE: PRT
<213> ORGANISM: Artificial Sequence
<220> FEATURE:
<223> OTHER INFORMATION: HPPD mutant - Axmi305H-Evo41

<400> SEQUENCE: 56

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
                20                  25                  30

Pro Asp Pro Val Ala Met Gly Gln Leu Phe Glu Arg Met Gly Phe Gln
            35                  40                  45

Ala Ile Ala Lys His Arg Arg Lys Asn Val Thr Leu Tyr Arg Gln Gly
        50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110
```

Gly Tyr Ala Gln Gln Ala Ala Pro Gly Glu Leu Ser Ile Pro Ala Ile
            115                 120                 125

Lys Gly Ile Gly Asp Ser Leu Ile Tyr Phe Ile Asp Lys Trp Arg Gly
    130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
            195                 200                 205

Ile Arg Tyr Phe Asp Ile Glu Gly Gln Ala Thr Gly Val Lys Ser Lys
        210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
            290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Trp
            340                 345                 350

Asn Phe Ala Gln Leu Phe Glu Thr Met Glu Leu Asp Gln Met Arg Arg
        355                 360                 365

Gly Val Leu Lys Thr
    370

<210> SEQ ID NO 57
<211> LENGTH: 357
<212> TYPE: PRT
<213> ORGANISM: Pseudomonas aeruginosa

<400> SEQUENCE: 57

Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser

```
            100                 105                 110
His Ala Asn Phe Gly Glu Leu Asn Ile Pro Ser Leu Glu Gly Ile Gly
            115                 120                 125

Gly Ser Leu Leu Tyr Leu Val Asp Arg Tyr Gly Asp Arg Ser Ile Tyr
        130                 135                 140

Asp Val Asp Phe Glu Phe Ile Glu Gly Arg Ser Ala Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
        195                 200                 205

Arg Ala Met Thr Ala Pro Cys Gly Lys Ile Arg Ile Pro Ile Asn Glu
    210                 215                 220

Ser Ala Asp Asp Thr Ser Gln Ile Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Arg Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
                325                 330                 335

Glu Gly Asn Phe Lys Ala Leu Phe Glu Ser Ile Glu Glu Asp Gln Ile
            340                 345                 350

Arg Arg Gly Val Ile
            355

<210> SEQ ID NO 58
<211> LENGTH: 358
<212> TYPE: PRT
<213> ORGANISM: Pseudomonas agarici

<400> SEQUENCE: 58

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Ala Ile Asn Leu Ile Leu Asn Asn Glu Pro His
    50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Glu Thr Gly Pro Met Glu Leu
            100                 105                 110
```

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Phe
130                 135                 140

Leu Glu Gly Val Asp Arg Asn Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Gln Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ser Arg Gly Ile Leu Leu Asp Gly Ala Ser Asp Lys Glu Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Ala Thr Glu
        355

<210> SEQ ID NO 59
<211> LENGTH: 373
<212> TYPE: PRT
<213> ORGANISM: Comamonas testosteroni

<400> SEQUENCE: 59

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

```
Lys Gly Ile Gly Asp Ser Leu Ile Tyr Phe Ile Asp Lys Trp Arg Gly
        130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Val Lys Ser Lys
    210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
    290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Glu Gly
            340                 345                 350

Asn Phe Lys Ala Leu Phe Glu Thr Met Glu Leu Asp Gln Met Arg Arg
        355                 360                 365

Gly Val Leu Lys Thr
    370

<210> SEQ ID NO 60
<211> LENGTH: 1071
<212> TYPE: DNA
<213> ORGANISM: Pseudomonas aeruginosa

<400> SEQUENCE: 60
atgaacgccg tggccaagat cgaacagcac aatcccatcg gtaccgacgg attcgaattc      60
gtcgagttca ccgcccccga cgccaagggc atcgagcagc tgcgccagct gttcaacatg     120
atgggcttca ccgaaaccgc caagcatcgt tccaaggaag tcttcctgtt ccagcagaac     180
gatatcaaca tcgtgctcaa cggcagccca accgggcatg tccatgaatt cgccctcaag     240
cacggcccga cgcctgcgc catggccttc cgggtgaaga acgcttccca ggccgccgcc     300
tacgccgaat cccagggcgc caagctggtg ggcagccacg ccaacttcgg cgagctgaac     360
atcccttccc tggaaggcat cggcggttcg ctgctgtatc ttgtcgaccg ctacggcgac     420
cgcagcatct atgacgtcga cttcgagttc atcgaaggcc gcagcgccaa cgacaactcg     480
gtcggcctga cctacatcga ccacctcacc cacaacgtca gcgcggcca gatggacgtc     540 tggtccggtt tctacgagcg catcgccaac ttccgcgaga ttcgctactt cgacatcgaa     600
ggcaagctca ccggcctgtt ctcccgcgcc atgaccgcac cttgcgggaa gatccgcatc     660
```

```
ccgatcaacg agtcggccga cgatacctcg cagatcgagg aattcatccg cgaataccat    720
ggcgaaggca tccagcacat cgccctgacc accgacgaca tctatgccac cgtgcgcaag    780
ctgcgcgaca acggcgtgaa gttcatgtcg accccggaca cctactacga aaggtcgac     840 acccgcgtcg ccgggcatgg cgagccgctc gagcaactgc gcgaactgaa cctgctgatc    900
gacggcgccc cgggcgacga cggcatcctg ctgcagatct tcaccgacac ggtgatcggc    960
ccgatcttct tcgagatcat ccagcgcaag ggcaaccagg gcttcggcga gggcaatttc   1020
aaggccctgt tcgagtccat cgaggaagac cagattcgcc gcggcgtgat c            1071

<210> SEQ ID NO 61
<211> LENGTH: 1074
<212> TYPE: DNA
<213> ORGANISM: Pseudomonas agarici

<400> SEQUENCE: 61
atggcagatt tatacgaaaa cccaatgggc ctgatgggct tcgagttcat cgagttcgca     60
tcgccgactc ctggcaccct ggagccgatc ttcgagatca tgggcttcac caaggtcgcg    120
acccaccgtt ccaagaacgt gcacctgtat cgccagggcg cgatcaacct gatcctcaac    180
aacgaacccc acagcgttgc ttcgtacttc gcggctgaac acggcccgtc cgtttgcggc    240
atggcgttcc gggtcaagga ttcgcagaag gcctacaacc gcgcactgga actcggcgcc    300
cagccgatcc acatcgaaac aggcccgatg gagctgaacc tgccggcgat caaaggcatt    360
ggcggcgcgc cgctgtacct gatcgaccgt tcggcgaag gcagctcgat ctatgacatc    420
gacttcgtgt tcctcgaagg cgttgaccgc aacccggtcg gtgccggcct gaagatcatc    480
gaccacctga cccacaacgt gtatcgcggc cgcatggcct actgggccaa cttctacgag    540
aagctgttca cttccgcga gatccgctac ttcgacatca aaggcgaata caccggcctg    600
acctcgaaag cgatgaccgc accggacggc atgatccgca tcccgctcaa cgaagaatcg    660
tcgaagggtg ccgggcagat cgaagagttc ctgatgcagt tcaacggcga aggcatccag    720
cacgtggcgt tcctcaccga cgacctggtc aagacctggg atcagttgaa gaagatcggc    780 atgcgttca tgaccgcgcc gccggacacc tactacgaaa tgctcgaagg ccgcctgccg    840
aaccacggcg agccggtgga tcaactgcaa tcgcgcggca tcctgctcga cggtgcgtcg    900
gataaagaag acaagcgtct gctgctgcag atcttctcgg aaaccctgat gggcccggtg    960
ttcttcgaat tcatccagcg taaaggcgat gatggtttcg gagaaggcaa cttcaaggct   1020
ctgttcgaat cgatcgagcg tgaccaggtg cgtcgtggcg tgctcgctac cgag         1074

<210> SEQ ID NO 62
<211> LENGTH: 1122
<212> TYPE: DNA
<213> ORGANISM: Comamonas testosteroni

<400> SEQUENCE: 62
atgaacgccc cgttgaccca aagcaatgcc agccagttcc agacctggga caaccccatg     60
ggcacggacg gcttcgagtt cgtcgaatac gcggcccccg atcccgtggc catgggtcag    120
ctgttcgagc gcatgggctt tcaggccatt gccaagcacc gccgcaagaa cgtgaccctg    180
tatcgccagg gcgagatcaa cttcatcatc aatgccgaac ccgacagctt tgcccagcgt    240
ttcgcgcgtc tgcacggccc cagcgtctgc gccatcgcca tccgcgtcaa cgacgccaag    300
tacgcctatg agcgcgccac ctcgctgggt gcctgggct atgcccagca ggccgccccc    360
ggcgaactga gcattcccgc catcaagggc attggcgact ccctgatcta tttcatcgac    420
```

```
aaatggcgcg gcaagaatgg cgccaaggac ggtgatctcg gcaatatcag cttcttcgac    480
gtggacttcg agcctctgcc cggtgccgat ctgcatcccg agggcctggg cctgacctat    540
atcgaccacc tgaccaacaa cgtctaccgc ggccgcatgg ccgagctggc cgagttctac    600
gagcgcatct tcaacttccg cgagatccgc tacttcgaca tcgaaggcca ggccacaggc    660
gtcaagagca aggccatgac cagcccctgc ggcaagatcc gcattcccat caacgaggaa    720
ggcaacgaca aggccggcca gattcaggag tatctggaca tgtaccgcgg cgaaggcata    780
cagcacatcg cgctgggatc gaccaatctc tacgacaccg tggacggtct gcagatgaac    840
ggcatcaagc tgctgaacac cagcgagacc tattacgagc tgctgcccaa gcgcatcccg    900
gacctgcagg aacccattcc cgagctgctg gcgcgcaaca tccttgtgga cggccagccc    960
ggcgagctgc tgctgcagat cttcagcgaa aaccagctgg gtcccatctt cttcgagttc    1020
atccagcgca agggcaatag cggctttggc gagggcaatt tcaaggcctt gttcgagacc    1080
atggaactcg accagatgcg ccgcggcgtg ctcaagacct ga                       1122
```

<210> SEQ ID NO 63  
<211> LENGTH: 440  
<212> TYPE: PRT  
<213> ORGANISM: Avena sativa

<400> SEQUENCE: 63

```
Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
```

```
                        245                 250                 255
Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
            275                 280                 285

Leu Glu Tyr His Gly Gly Pro Gly Val Gln His Ile Ala Leu Ala Ser
            290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Gln Ile Lys Glu
                340                 345                 350

Cys Gln Glu Leu Gly Val Leu Val Asp Arg Asp Gln Gly Val Leu
                355                 360                 365

Leu Gln Ile Phe Thr Lys Pro Val Gly Asp Arg Pro Thr Phe Phe Leu
            370                 375                 380

Glu Met Ile Gln Arg Ile Gly Cys Met Glu Lys Asp Glu Val Gly Gln
385                 390                 395                 400

Glu Tyr Gln Lys Gly Cys Gly Gly Phe Lys Gly Asn Phe Ser
                405                 410                 415

Glu Leu Phe Lys Ser Ile Glu Asp Tyr Glu Lys Ser Leu Glu Val Lys
            420                 425                 430

Gln Ser Val Val Ala Gln Lys Ser
            435                 440

<210> SEQ ID NO 64
<211> LENGTH: 439
<212> TYPE: PRT
<213> ORGANISM: Artificial Sequence
<220> FEATURE:
<223> OTHER INFORMATION: HPPD mutant - Avena sativum deletion mutant

<400> SEQUENCE: 64

Met Pro Pro Thr Pro Ala Thr Ala Thr Gly Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
```

```
                    165                 170                 175
Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
            245                 250                 255

Ser Val Val Leu Ala Asn Asn Ser Glu Ala Val Leu Leu Pro Leu Asn
        260                 265                 270

Glu Pro Val His Gly Thr Lys Arg Arg Ser Gln Ile Gln Thr Tyr Leu
    275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
            325                 330                 335

Arg Arg Ile Ala Gly Asp Val Leu Ser Glu Glu Gln Ile Lys Glu Cys
        340                 345                 350

Gln Glu Leu Gly Val Leu Val Asp Arg Asp Gln Gly Val Leu Leu
    355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
            405                 410                 415

Leu Phe Lys Ser Ile Glu Asp Tyr Glu Lys Ser Leu Glu Val Lys Gln
        420                 425                 430

Ser Val Val Ala Gln Lys Ser
    435

<210> SEQ ID NO 65
<211> LENGTH: 444
<212> TYPE: PRT
<213> ORGANISM: Zea mays

<400> SEQUENCE: 65

Met Gly Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95
```

```
Ser Phe Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
            130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
    290                 295                 300

Ser Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Asp Gln Gly Val
        355                 360                 365

Leu Leu Gln Ile Phe Thr Lys Pro Val Gly Asp Arg Pro Thr Leu Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Ala Gln Gly Ser
        435                 440

<210> SEQ ID NO 66
<211> LENGTH: 445
<212> TYPE: PRT
<213> ORGANISM: Arabidopsis thaliana

<400> SEQUENCE: 66

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30
```

```
Val Arg Lys Asn Pro Lys Ser Asp Lys Phe Lys Val Lys Arg Phe His
        35                  40                  45

His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
130                 135                 140

Glu Val Glu Asp Ala Glu Ser Ala Phe Ser Ile Ser Val Ala Asn Gly
145                 150                 155                 160

Ala Ile Pro Ser Ser Pro Ile Val Leu Asn Glu Ala Val Thr Ile
                165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
        210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
            245                 250                 255

Asp Val Gly Thr Ala Glu Ser Gly Leu Asn Ser Ala Val Leu Ala Ser
        260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
        290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Pro Thr Tyr Tyr Gln Asn Leu Lys Lys Arg Val Gly Asp
            340                 345                 350

Val Leu Ser Asp Asp Gln Ile Lys Glu Cys Glu Glu Leu Gly Ile Leu
        355                 360                 365

Val Asp Arg Asp Asp Gln Gly Thr Leu Leu Gln Ile Phe Thr Lys Pro
        370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445
```

<210> SEQ ID NO 67
<211> LENGTH: 434
<212> TYPE: PRT
<213> ORGANISM: Hordeum vulgare

<400> SEQUENCE: 67

```
Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Arg Arg Arg Gly Ala Arg Pro Ala Phe Ala Pro Val Asp Leu Gly
145                 150                 155                 160

Arg Gly Phe Ala Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
    210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Gly Val Leu Leu Pro Leu Asn Glu Pro Val His Gly
            260                 265                 270

Thr Lys Arg Arg Ser Gln Ile Gln Thr Phe Leu Glu His His Gly Gly
        275                 280                 285

Pro Gly Val Gln His Ile Ala Val Ala Ser Ser Asp Val Leu Arg Thr
    290                 295                 300

Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
        355                 360                 365

Pro Val Gly Asp Arg Pro Thr Leu Phe Leu Glu Met Ile Gln Arg Ile
    370                 375                 380
```

Gly Cys Met Glu Lys Asp Glu Arg Gly Glu Glu Tyr Gln Lys Gly Gly
385                 390                 395                 400

Cys Gly Gly Phe Gly Lys Gly Asn Phe Ser Glu Leu Phe Lys Ser Ile
            405                 410                 415

Glu Asp Tyr Glu Lys Ser Leu Glu Ala Lys Gln Ser Ala Ala Val Gln
            420                 425                 430

Gly Ser

<210> SEQ ID NO 68
<211> LENGTH: 442
<212> TYPE: PRT
<213> ORGANISM: Daucus carota

<400> SEQUENCE: 68

Met Gly Lys Lys Gln Ser Glu Ala Glu Ile Leu Ser Ser Asn Ser Ser
1               5                   10                  15

Asn Thr Ser Pro Ala Thr Phe Lys Leu Val Gly Phe Asn Asn Phe Val
            20                  25                  30

Arg Ala Asn Pro Lys Ser Asp His Phe Ala Val Lys Arg Phe His His
            35                  40                  45

Ile Glu Phe Trp Cys Gly Asp Ala Thr Asn Thr Ser Arg Arg Phe Ser
50                  55                  60

Trp Gly Leu Gly Met Pro Leu Val Ala Lys Ser Asp Leu Ser Thr Gly
65                  70                  75                  80

Asn Ser Val His Ala Ser Tyr Leu Val Arg Ser Ala Asn Leu Ser Phe
                85                  90                  95

Val Phe Thr Ala Pro Tyr Ser Pro Ser Thr Thr Thr Ser Ser Gly Ser
            100                 105                 110

Ala Ala Ile Pro Ser Phe Ser Ala Ser Gly Phe His Ser Phe Ala Ala
            115                 120                 125

Lys His Gly Leu Ala Val Arg Ala Ile Ala Leu Glu Val Ala Asp Val
            130                 135                 140

Ala Ala Ala Phe Glu Ala Ser Val Ala Arg Gly Ala Arg Pro Ala Ser
145                 150                 155                 160

Ala Pro Val Glu Leu Asp Asp Gln Ala Trp Leu Ala Glu Val Glu Leu
                165                 170                 175

Tyr Gly Asp Val Val Leu Arg Phe Val Ser Phe Gly Arg Glu Glu Gly
            180                 185                 190

Leu Phe Leu Pro Gly Phe Glu Ala Val Glu Gly Thr Ala Ser Phe Pro
            195                 200                 205

Asp Leu Asp Tyr Gly Ile Arg Arg Leu Asp His Ala Val Gly Asn Val
            210                 215                 220

Thr Glu Leu Gly Pro Val Val Glu Tyr Ile Lys Gly Phe Thr Gly Phe
225                 230                 235                 240

His Glu Phe Ala Glu Phe Thr Ala Glu Asp Val Gly Thr Leu Glu Ser
                245                 250                 255

Gly Leu Asn Ser Val Val Leu Ala Asn Asn Glu Glu Met Val Leu Leu
            260                 265                 270

Pro Leu Asn Glu Pro Val Tyr Gly Thr Lys Arg Lys Ser Gln Ile Gln
            275                 280                 285

Thr Tyr Leu Glu His Asn Glu Gly Ala Gly Val Gln His Leu Ala Leu
            290                 295                 300

Val Ser Glu Asp Ile Phe Arg Thr Leu Arg Glu Met Arg Lys Arg Ser
305                 310                 315                 320

```
Cys Leu Gly Gly Phe Glu Phe Met Pro Ser Pro Pro Thr Tyr Tyr
                325                 330                 335

Lys Asn Leu Lys Asn Arg Val Gly Asp Val Leu Ser Asp Glu Gln Ile
            340                 345                 350

Lys Glu Cys Glu Asp Leu Gly Ile Leu Val Asp Arg Asp Asp Gln Gly
        355                 360                 365

Thr Leu Leu Gln Ile Phe Thr Lys Pro Val Gly Asp Arg Pro Thr Leu
    370                 375                 380

Phe Ile Glu Ile Ile Gln Arg Val Gly Cys Met Leu Lys Asp Asp Ala
385                 390                 395                 400

Gly Gln Met Tyr Gln Lys Gly Gly Cys Gly Gly Phe Gly Lys Gly Asn
                405                 410                 415

Phe Ser Glu Leu Phe Lys Ser Ile Glu Glu Tyr Glu Lys Thr Leu Glu
            420                 425                 430

Ala Lys Gln Ile Thr Gly Ser Ala Ala Ala
        435                 440

<210> SEQ ID NO 69
<211> LENGTH: 380
<212> TYPE: PRT
<213> ORGANISM: Streptomyces avermitilis

<400> SEQUENCE: 69

Met Thr Gln Thr Thr His His Thr Pro Asp Thr Ala Arg Gln Ala Asp
1               5                   10                  15

Pro Phe Pro Val Lys Gly Met Asp Ala Val Phe Ala Val Gly Asn
            20                  25                  30

Ala Lys Gln Ala Ala His Tyr Ser Thr Ala Phe Gly Met Gln Leu Val
        35                  40                  45

Ala Tyr Ser Gly Pro Glu Asn Gly Ser Arg Glu Thr Ala Ser Tyr Val
    50                  55                  60

Leu Thr Asn Gly Ser Ala Arg Phe Val Leu Thr Ser Val Ile Lys Pro
65                  70                  75                  80

Ala Thr Pro Trp Gly His Phe Leu Ala Asp His Val Ala Glu His Gly
                85                  90                  95

Asp Gly Val Val Asp Leu Ala Ile Glu Val Pro Asp Ala Arg Ala Ala
            100                 105                 110

His Ala Tyr Ala Ile Glu His Gly Ala Arg Ser Val Ala Glu Pro Tyr
        115                 120                 125

Glu Leu Lys Asp Glu His Gly Thr Val Val Leu Ala Ala Ile Ala Thr
    130                 135                 140

Tyr Gly Lys Thr Arg His Thr Leu Val Asp Arg Thr Gly Tyr Asp Gly
145                 150                 155                 160

Pro Tyr Leu Pro Gly Tyr Val Ala Ala Pro Ile Val Glu Pro Pro
                165                 170                 175

Ala His Arg Thr Phe Gln Ala Ile Asp His Cys Val Gly Asn Val Glu
            180                 185                 190

Leu Gly Arg Met Asn Glu Trp Val Gly Phe Tyr Asn Lys Val Met Gly
        195                 200                 205

Phe Thr Asn Met Lys Glu Phe Val Gly Asp Asp Ile Ala Thr Glu Tyr
    210                 215                 220

Ser Ala Leu Met Ser Lys Val Val Ala Asp Gly Thr Leu Lys Val Lys
225                 230                 235                 240

Phe Pro Ile Asn Glu Pro Ala Leu Ala Lys Lys Lys Ser Gln Ile Asp
```

```
            245                 250                 255
Glu Tyr Leu Glu Phe Tyr Gly Ala Gly Val Gln His Ile Ala Leu
            260                 265                 270

Asn Thr Gly Asp Ile Val Glu Thr Val Arg Thr Met Arg Ala Ala Gly
            275                 280                 285

Val Gln Phe Leu Asp Thr Pro Asp Ser Tyr Tyr Asp Thr Leu Gly Glu
            290                 295                 300

Trp Val Gly Asp Thr Arg Val Pro Val Asp Thr Leu Arg Glu Leu Lys
305                 310                 315                 320

Ile Leu Ala Asp Arg Asp Glu Asp Gly Tyr Leu Leu Gln Ile Phe Thr
                325                 330                 335

Lys Pro Val Gln Asp Arg Pro Thr Val Phe Phe Glu Ile Ile Glu Arg
                340                 345                 350

His Gly Ser Met Gly Phe Gly Lys Gly Asn Phe Lys Ala Leu Phe Glu
                355                 360                 365

Ala Ile Glu Arg Glu Gln Glu Lys Arg Gly Asn Leu
                370                 375                 380

<210> SEQ ID NO 70
<211> LENGTH: 419
<212> TYPE: PRT
<213> ORGANISM: Mycosphaerella graminicola

<400> SEQUENCE: 70

Met Ala Pro Gly Ala Leu Leu Val Thr Ser Gln Asn Gly Arg Thr Ser
1               5                   10                  15

Pro Leu Tyr Asp Ser Asp Gly Tyr Val Pro Ala Pro Ala Ala Leu Val
                20                  25                  30

Val Gly Gly Glu Val Asn Tyr Arg Gly Tyr His His Ala Glu Trp Trp
            35                  40                  45

Val Gly Asn Ala Lys Gln Val Ala Gln Phe Tyr Ile Thr Arg Met Gly
        50                  55                  60

Phe Glu Pro Val Ala His Lys Gly Leu Glu Thr Gly Ser Arg Phe Phe
65              70                  75                  80

Ala Ser His Val Val Gln Asn Asn Gly Val Arg Phe Val Phe Thr Ser
                85                  90                  95

Pro Val Arg Ser Ser Ala Arg Gln Thr Leu Lys Ala Ala Pro Leu Ala
                100                 105                 110

Asp Gln Ala Arg Leu Asp Glu Met Tyr Asp His Leu Asp Lys His Gly
            115                 120                 125

Asp Gly Val Lys Asp Val Ala Phe Glu Val Asp Val Leu Ala Val
        130                 135                 140

Tyr Glu Asn Ala Val Ala Asn Gly Ala Glu Ser Val Ser Ser Pro His
145                 150                 155                 160

Thr Asp Ser Cys Asp Glu Gly Asp Val Ile Ser Ala Ala Ile Lys Thr
                165                 170                 175

Tyr Gly Asp Thr Thr His Thr Phe Ile Gln Arg Thr Thr Tyr Thr Gly
                180                 185                 190

Pro Phe Leu Pro Gly Tyr Arg Ser Cys Thr Thr Val Asp Ser Ala Asn
            195                 200                 205

Lys Phe Leu Pro Pro Val Asn Leu Glu Ala Ile Asp His Cys Val Gly
        210                 215                 220

Asn Gln Asp Trp Asp Glu Met Ser Asp Ala Cys Asp Phe Tyr Glu Arg
225                 230                 235                 240
```

```
Cys Leu Gly Phe His Arg Phe Trp Ser Val Asp Asp Lys Asp Ile Cys
            245                 250                 255

Thr Glu Phe Ser Ala Leu Lys Ser Ile Val Met Ser Ser Pro Asn Gln
            260                 265                 270

Val Val Lys Met Pro Ile Asn Glu Pro Ala His Gly Lys Lys Lys Ser
        275                 280                 285

Gln Ile Glu Glu Tyr Val Asp Phe Tyr Asn Gly Pro Gly Val Gln His
    290                 295                 300

Ile Ala Leu Arg Thr Pro Asn Ile Ile Glu Ala Val Ser Asn Leu Arg
305                 310                 315                 320

Ser Arg Gly Val Glu Phe Ile Ser Val Pro Asp Thr Tyr Tyr Glu Asn
            325                 330                 335

Met Arg Leu Arg Leu Lys Ala Ala Gly Met Lys Leu Glu Glu Ser Phe
            340                 345                 350

Asp Ile Ile Gln Lys Leu Asn Ile Leu Ile Asp Phe Asp Glu Gly Gly
        355                 360                 365

Tyr Leu Leu Gln Leu Phe Thr Lys Pro Leu Met Asp Arg Pro Thr Val
    370                 375                 380

Phe Ile Glu Ile Ile Gln Arg Asn Asn Phe Asp Gly Phe Gly Ala Gly
385                 390                 395                 400

Asn Phe Lys Ser Leu Phe Glu Ala Ile Glu Arg Glu Gln Asp Leu Arg
            405                 410                 415

Gly Asn Leu

<210> SEQ ID NO 71
<211> LENGTH: 399
<212> TYPE: PRT
<213> ORGANISM: Coccicoides immitis

<400> SEQUENCE: 71

Met Ala Pro Ala Ala Asp Ser Pro Thr Leu Gln Pro Ala Gln Pro Ser
1               5                   10                  15

Asp Leu Asn Gln Tyr Arg Gly Tyr Asp His Val His Trp Tyr Val Gly
            20                  25                  30

Asn Ala Lys Gln Ala Ala Thr Tyr Tyr Val Thr Arg Met Gly Phe Glu
        35                  40                  45

Arg Val Ala Tyr Arg Gly Leu Glu Thr Gly Ser Lys Ala Val Ala Ser
    50                  55                  60

His Val Val Arg Asn Gly Asn Ile Thr Phe Ile Leu Thr Ser Pro Leu
65                  70                  75                  80

Arg Ser Val Glu Gln Ala Ser Arg Phe Pro Glu Asp Glu Ala Leu Leu
            85                  90                  95

Lys Glu Ile His Ala His Leu Glu Arg His Gly Asp Gly Val Lys Asp
            100                 105                 110

Val Ala Phe Glu Val Asp Cys Val Glu Ser Val Phe Ser Ala Ala Val
        115                 120                 125

Arg Asn Gly Ala Glu Val Val Ser Asp Val Arg Thr Val Glu Asp Glu
    130                 135                 140

Asp Gly Gln Ile Lys Met Ala Thr Ile Arg Thr Tyr Gly Glu Thr Thr
145                 150                 155                 160

His Thr Leu Ile Glu Arg Ser Gly Tyr Arg Gly Gly Phe Met Pro Gly
            165                 170                 175

Tyr Arg Met Glu Ser Asn Ala Asp Ala Thr Ser Lys Phe Leu Pro Lys
            180                 185                 190
```

```
Val Val Leu Glu Arg Ile Asp His Cys Val Gly Asn Gln Asp Trp Asp
            195                 200                 205

Glu Met Glu Arg Val Cys Asp Tyr Tyr Glu Lys Ile Leu Gly Phe His
210                 215                 220

Arg Phe Trp Ser Val Asp Asp Lys Asp Ile Cys Thr Glu Phe Ser Ala
225                 230                 235                 240

Leu Lys Ser Ile Val Met Ala Ser Pro Asn Asp Ile Val Lys Met Pro
                245                 250                 255

Ile Asn Glu Pro Ala Lys Gly Lys Lys Gln Ser Gln Ile Glu Glu Tyr
            260                 265                 270

Val Asp Phe Tyr Asn Gly Ala Gly Val Gln His Ile Ala Leu Arg Thr
            275                 280                 285

Asn Asn Ile Ile Asp Ala Ile Thr Asn Leu Lys Ala Arg Gly Thr Glu
290                 295                 300

Phe Ile Lys Val Pro Glu Thr Tyr Tyr Glu Asp Met Lys Ile Arg Leu
305                 310                 315                 320

Lys Arg Gln Gly Leu Val Leu Asp Glu Asp Phe Glu Thr Leu Lys Ser
                325                 330                 335

Leu Asp Ile Leu Ile Asp Phe Asp Glu Asn Gly Tyr Leu Leu Gln Leu
            340                 345                 350

Phe Thr Lys His Leu Met Asp Arg Pro Thr Val Phe Ile Glu Ile Ile
            355                 360                 365

Gln Arg Asn Asn Phe Ser Gly Phe Gly Ala Gly Asn Phe Arg Ala Leu
            370                 375                 380

Phe Glu Ala Ile Glu Arg Glu Gln Ala Leu Arg Gly Thr Leu Ile
385                 390                 395
```

<210> SEQ ID NO 72
<211> LENGTH: 350
<212> TYPE: PRT
<213> ORGANISM: Unknown
<220> FEATURE:
<223> OTHER INFORMATION: Bacterial - Synechococcoideae spp.

<400> SEQUENCE: 72

```
Met Asn Pro Ser Ile Arg Ile Val Gln Gly Ile His His Leu His Phe
1               5                   10                  15

Tyr Leu Trp Asp Leu Pro Arg Trp Arg Glu His Phe Cys Arg Val Trp
                20                  25                  30

Gly Phe Arg Val Ala Ser Asp Ala Gly Asn Thr Leu Glu Leu Glu Gln
            35                  40                  45

Gly Ser Leu Arg Leu Arg Leu Ser Gln Pro Ala Arg Ala Gly Asp Glu
        50                  55                  60

Val Asp Arg His Leu Gln Arg His Gly Pro Gly Val Val Asp Val Ala
65                  70                  75                  80

Leu Ala Val Gly Glu Gln Glu Leu Pro Ala Leu Ala Glu Leu Leu Arg
                85                  90                  95

Gly Arg Gly Ala Gln Leu Ala Trp Ile Pro Ala Ala Ala Leu Cys
            100                 105                 110

Leu His Thr Pro Tyr Gly Ile Arg His Ser Leu Ile Pro Gly Pro Leu
        115                 120                 125

Asp Ala Ala Pro Ala Glu Ala Gly Leu Phe Ser His Trp Asp His Val
130                 135                 140

Val Leu Asn Val Glu Gln Gly Ser Leu Gln Ala Ala Asp Trp Tyr
145                 150                 155                 160
```

```
Gly Arg Val Leu Gly Trp Arg Arg Leu Tyr Arg Tyr Ser Ile Gly Thr
            165                 170                 175

Ala Thr Ser Gly Leu Glu Ser Val Val Gly Asp Pro Glu Ala Gly
        180                 185                 190

Ile Gln Trp Ala Ile Asn Glu Pro Thr Cys Ala Ala Ser Gln Ile Gln
            195                 200                 205

Glu Phe Leu His Ala His Gly Pro Gly Ile Gln His Ala Ala Leu
        210                 215                 220

His Ser Ser Asp Ile Val Ala Ser Leu Arg Arg Leu Arg Gln Gly Gly
225                 230                 235                 240

Val Asp Phe Leu Gln Val Ala Pro Gln Tyr Tyr Thr Ser Leu Glu Arg
            245                 250                 255

Glu Leu Gly Leu Ala Leu Arg Ser Ala Leu Gly Gln Ala Ile Ser Trp
        260                 265                 270

Gln Asp Leu Val Glu Gln Gln Ile Leu Leu Asp Ala Thr Leu Pro Ala
            275                 280                 285

Ser Asp Gly Gln Asp Arg Pro Leu Leu Leu Gln Thr Phe Thr Gln Pro
        290                 295                 300

Leu Phe Gly Arg Pro Thr Phe Phe Glu Val Ile Gln Arg Leu Gly
305                 310                 315                 320

Gly Ala Thr Gly Phe Gly Glu Ala Asn Phe Gln Ala Leu Phe Glu Ala
            325                 330                 335

Leu Glu Arg Gln Gln Arg Gln Arg His Gln Ala Leu Thr Pro
        340                 345                 350

<210> SEQ ID NO 73
<211> LENGTH: 368
<212> TYPE: PRT
<213> ORGANISM: Picrophilus torridus

<400> SEQUENCE: 73

Met Tyr Gly Lys Asn Leu Ile Ser Glu Leu Arg Glu Lys Glu Ile Phe
1               5                   10                  15

Lys Arg Leu His His Val Glu Phe Tyr Val Ser Ser Ala Lys Thr Trp
            20                  25                  30

Ser Tyr Phe Met Asn Arg Gly Leu Gly Phe Lys Thr Val Ala Tyr Ala
        35                  40                  45

Gly Pro Glu Thr Gly Ile Arg Asp Lys Ile Ser Tyr Val Met Ser Gln
    50                  55                  60

Gly Thr Ala Arg Ile Ser Phe Thr Ser Ser Met Asn Asp Asp Ser Tyr
65                  70                  75                  80

Ile Ser Asn His Val Lys Lys His Gly Asp Gly Val Lys Asp Ile Ala
                85                  90                  95

Leu Glu Val Asp Asp Leu Asp Glu Ala Lys Ser Leu Ile Glu Lys Tyr
            100                 105                 110

Gly Thr Lys Val Ser Lys Ile Asn Glu Ile Lys Asp Gly Asn Gly Lys
        115                 120                 125

Ile Arg Thr Ala Glu Ile Lys Thr Tyr Gly Glu Thr Val His Thr Leu
    130                 135                 140

Ile Glu Thr Gly Asp Tyr Asn Gly Val Phe Met Pro Gly Tyr Glu Glu
145                 150                 155                 160

Ser Glu Ile Asn Ser Lys Asn Thr Gly Ile Lys Lys Ile Asp His Ile
                165                 170                 175

Val Gly Asn Val Tyr Glu Gly Glu Met Asp Ser Trp Val Asn Phe Tyr
            180                 185                 190
```

```
Ile Glu Lys Leu Gly Phe Glu His Leu Ile Thr Phe Asp Asp Lys Asp
            195                 200                 205

Ile Arg Thr Asp Tyr Ser Ala Leu Arg Ser Lys Val Val Lys Tyr Asn
210                 215                 220

Asp Asp Ile Val Phe Pro Ile Asn Glu Pro Ala Lys Gly Leu Arg Lys
225                 230                 235                 240

Ser Gln Ile Glu Glu Tyr Leu Asp Tyr Arg Ser Glu Gly Val Gln
            245                 250                 255

His Ile Ala Leu Leu Thr Asp Asp Ile Ile Lys Thr Val Ser Met Met
            260                 265                 270

Glu Glu Asn Gly Ile Glu Phe Leu Lys Thr Pro Gly Ser Tyr Tyr Glu
            275                 280                 285

Ser Leu Ser Ser Arg Ile Gly Ser Ile Asp Glu Asp Leu Asn Glu Ile
            290                 295                 300

Glu Lys His Asn Ile Leu Val Asp Arg Asp Glu Asn Gly Tyr Leu Leu
305                 310                 315                 320

Gln Ile Phe Thr Lys Pro Val Thr Asp Arg Pro Thr Phe Phe Phe Glu
            325                 330                 335

Val Ile Gln Arg Lys Gly Ala Arg Ser Phe Gly Asn Gly Asn Phe Lys
            340                 345                 350

Ala Leu Phe Glu Ala Ile Glu Arg Glu Gln Ala Lys Arg Gly Asn Leu
            355                 360                 365

<210> SEQ ID NO 74
<211> LENGTH: 387
<212> TYPE: PRT
<213> ORGANISM: Kordia algicida

<400> SEQUENCE: 74

Met Ala Ala Glu Ile Lys Asn Leu Lys Asp Leu Gln Asn Thr Glu Tyr
1               5                   10                  15

Gly Leu Lys Lys Leu Phe Asp Glu Ala Glu Asp Phe Leu Pro Leu Leu
            20                  25                  30

Gly Thr Asp Tyr Val Glu Leu Tyr Val Gly Asn Ala Lys Gln Ser Ala
            35                  40                  45

His Phe Tyr Lys Thr Ala Phe Gly Phe Gln Ser Glu Ala Tyr Ala Gly
        50                  55                  60

Leu Glu Thr Gly Leu Thr Asp Arg Val Ser Tyr Val Leu Lys Gln Asp
65                  70                  75                  80

Lys Ile Arg Leu Val Leu Thr Thr Pro Leu Gly Lys Gly Gly Glu Ile
                85                  90                  95

Asn Glu His Ile Asp Leu His Gly Asp Gly Val Lys Val Val Ala Leu
            100                 105                 110

Trp Val Glu Asp Ala Thr Lys Ala Phe Glu Glu Thr Thr Lys Arg Gly
            115                 120                 125

Ala Lys Pro Tyr Met Glu Pro Thr Lys Glu Glu Asp Glu Asn Gly Tyr
            130                 135                 140

Val Ile Arg Ser Gly Ile Tyr Thr Tyr Gly Thr Val His Val Phe
145                 150                 155                 160

Val Glu Arg Lys Asn Tyr Asn Gly Val Phe Leu Pro Gly Tyr Gln Arg
                165                 170                 175

Trp Glu Ser His Tyr Asn Pro Glu Pro Val Gly Leu Lys Phe Ile Asp
            180                 185                 190

His Met Val Gly Asn Val Gly Trp Gly Glu Met Lys Glu Trp Cys Glu
```

```
              195                 200                 205
Phe Tyr Ala Lys Val Met Gly Phe Ala Gln Ile Ile Ser Phe Thr Asp
210                 215                 220

Asp Asp Ile Ser Thr Asp Phe Thr Ala Leu Met Ser Lys Val Met Ser
225                 230                 235                 240

Asn Gly Asn Gly Arg Ile Lys Phe Pro Ile Asn Glu Pro Ala Glu Gly
                245                 250                 255

Lys Lys Lys Ser Gln Ile Glu Glu Tyr Leu Asp Phe Tyr Asn Gly Ser
            260                 265                 270

Gly Val Gln His Ile Ala Val Ala Thr Asp Asn Ile Ile Asp Thr Val
        275                 280                 285

Ser Gln Met Arg Glu Arg Gly Val Glu Phe Leu Tyr Val Pro Asp Thr
    290                 295                 300

Tyr Tyr Asp Asp Leu Leu Glu Arg Val Gly Asp Ile Asp Glu Asp Val
305                 310                 315                 320

Glu Glu Leu Lys Lys His Gly Ile Leu Ile Asp Arg Asp Glu Glu Gly
                325                 330                 335

Tyr Leu Leu Gln Leu Phe Thr Lys Thr Ile Val Asp Arg Pro Thr Met
            340                 345                 350

Phe Phe Glu Val Ile Gln Arg Lys Gly Ala Gln Ser Phe Gly Val Gly
        355                 360                 365

Asn Phe Lys Ala Leu Phe Glu Ala Ile Glu Arg Glu Gln Ala Ala Arg
    370                 375                 380

Gly Thr Leu
385

<210> SEQ ID NO 75
<211> LENGTH: 382
<212> TYPE: PRT
<213> ORGANISM: Blepharisma japonicum

<400> SEQUENCE: 75

Met Thr Tyr Tyr Asp Lys Gln Glu Thr Arg Pro Asp Leu Gly Glu Phe
1               5                   10                  15

Tyr Gly Phe His His Val Arg Phe Tyr Val Ser Asn Ser Glu Gln Ala
                20                  25                  30

Ala Ser Phe Tyr Thr Ser Arg Phe Gly Phe Ser Pro Val Ala Tyr Glu
            35                  40                  45

Gly Leu Glu Thr Gly Asn Gln Lys Phe Cys Thr Asn Val Val Arg Ser
        50                  55                  60

Asn His Val Val Ile Ala Phe Thr Ser Ala Leu Thr Pro Glu Asp Asn
65                  70                  75                  80

Glu Val Asn Arg His Val Gly Lys His Ser Asp Gly Val Gln Asp Ile
                85                  90                  95

Ala Phe Ser Val Ser Asp Ala Arg Gly Met Tyr Glu Lys Ala Ile Ala
            100                 105                 110

Lys Gly Cys Lys Ser Phe Arg Glu Pro Gln Val Leu Gln Asp Gln Phe
        115                 120                 125

Gly Ser Val Ile Ile Ala Ser Leu Gln Thr Tyr Gly Asp Thr Val His
    130                 135                 140

Thr Leu Val Gln Asn Val Asp Tyr Thr Gly Pro Phe Leu Pro Gly Phe
145                 150                 155                 160

Arg Ala Ile Thr Lys Asp Asp Pro Leu Asn Ser Ala Phe Pro Gln Val
                165                 170                 175
```

Asn Tyr Asp Ile Ile Asp His Val Val Gly Asn Gln Pro Gly Gly Asp
                180                 185                 190

Met Thr Pro Thr Val Glu Trp Tyr Glu Lys Tyr Leu Glu Phe His Arg
            195                 200                 205

Tyr Trp Ser Ala Asp Glu Ser Val Ile His Thr Asp Tyr Ser Ala Leu
        210                 215                 220

Arg Ser Val Val Val Ala Asp Trp Asp Glu Val Ile Lys Met Pro Ile
225                 230                 235                 240

Asn Glu Pro Ala Asp Gly Leu Arg Lys Ser Gln Ile Gln Glu Tyr Val
                245                 250                 255

Glu Tyr Tyr Gly Gly Ala Gly Val Gln His Ile Ala Leu Lys Val Asn
            260                 265                 270

Asp Ile Ile Ser Val Ile Ser Thr Leu Arg Ala Arg Gly Val Glu Phe
        275                 280                 285

Leu Glu Val Pro Pro Lys Tyr Tyr Asp Ser Leu Arg Lys Arg Leu Ala
290                 295                 300

His Ser Ala Val Gln Ile Glu Glu Asp Leu Lys Arg Ile Glu Asp Leu
305                 310                 315                 320

His Ile Leu Val Asp Phe Asp Asp Arg Gly Tyr Leu Leu Gln Ile Phe
                325                 330                 335

Thr Lys Pro Val Glu Asp Arg Pro Thr Leu Phe Tyr Glu Ile Ile Gln
            340                 345                 350

Arg His Asn Asn Asn Gly Phe Gly Ile Gly Asn Phe Lys Ala Leu Phe
        355                 360                 365

Glu Ser Leu Glu Gln Glu Gln Glu Arg Arg Gly Asn Leu Ile
370                 375                 380

<210> SEQ ID NO 76
<211> LENGTH: 401
<212> TYPE: PRT
<213> ORGANISM: Rhodococcus sp.

<400> SEQUENCE: 76

Met Thr Ile Glu Gln Thr Leu Thr Asp Lys Glu Arg Leu Ala Gly Leu
1               5                   10                  15

Asp Leu Gly Gln Leu Glu Gln Leu Val Gly Leu Val Glu Tyr Asp Gly
            20                  25                  30

Thr Arg Asp Pro Phe Pro Val Ser Gly Trp Asp Ala Val Val Trp Val
        35                  40                  45

Val Gly Asn Ala Thr Gln Thr Ala His Tyr Phe Gln Ser Ala Phe Gly
50                  55                  60

Met Thr Leu Val Ala Tyr Ser Gly Pro Thr Thr Gly Asn Arg Asp His
65                  70                  75                  80

His Ser Phe Val Leu Glu Ser Gly Ala Val Arg Phe Val Ile Lys Gly
                85                  90                  95

Ala Val Asn Pro Asp Ser Pro Leu Ile Asp His His Arg Thr His Gly
            100                 105                 110

Asp Gly Val Val Asp Ile Ala Leu Ala Val Pro Asp Val Asp Lys Cys
        115                 120                 125

Ile Ala His Ala Arg Ala Gln Gly Ala Thr Val Leu Asp Glu Pro His
130                 135                 140

Asp Val Thr Asp Asp His Gly Thr Val Arg Leu Ala Ala Ile Ala Thr
145                 150                 155                 160

Tyr Gly Asp Thr Arg His Thr Leu Val Asp Arg Ser His Tyr Thr Gly
                165                 170                 175

```
Pro Tyr Leu Pro Gly Tyr Thr Ala Arg Thr Ser Gly His Thr Lys Arg
            180                 185                 190

Asp Gly Ala Pro Lys Arg Leu Phe Gln Ala Leu Asp His Val Val Gly
        195                 200                 205

Asn Val Glu Leu Gly Lys Met Asp His Trp Val Asp Phe Tyr Asn Arg
    210                 215                 220

Val Met Gly Phe Thr Asn Met Ala Glu Phe Val Gly Glu Asp Ile Ala
225                 230                 235                 240

Thr Asp Tyr Ser Ala Leu Met Ser Lys Val Val Ser Asn Gly Asn His
            245                 250                 255

Arg Val Lys Phe Pro Leu Asn Glu Pro Ala Leu Ala Lys Lys Arg Ser
        260                 265                 270

Gln Ile Asp Glu Tyr Leu Asp Phe Tyr Arg Gly Pro Gly Ala Gln His
    275                 280                 285

Leu Ala Leu Ala Thr Asn Asp Ile Leu Thr Ala Val Asp Gln Leu Thr
290                 295                 300

Ala Glu Gly Val Glu Phe Leu Ala Thr Pro Asp Ser Tyr Tyr Glu Asp
305                 310                 315                 320

Pro Glu Leu Arg Ala Arg Ile Gly Asn Val Arg Ala Pro Ile Ala Glu
            325                 330                 335

Leu Gln Lys Arg Gly Ile Leu Val Asp Arg Asp Glu Asp Gly Tyr Leu
        340                 345                 350

Leu Gln Ile Phe Thr Lys Pro Leu Val Asp Arg Pro Thr Val Phe Phe
    355                 360                 365

Glu Leu Ile Glu Arg His Gly Ser Leu Gly Phe Gly Ile Gly Asn Phe
        370                 375                 380

Lys Ala Leu Phe Glu Ala Ile Glu Arg Glu Gln Ala Ala Arg Gly Asn
385                 390                 395                 400

Phe

<210> SEQ ID NO 77
<211> LENGTH: 18
<212> TYPE: DNA
<213> ORGANISM: Artificial Sequence
<220> FEATURE:
<223> OTHER INFORMATION: histidine tag

<400> SEQUENCE: 77
catcaccatc accatcac                                                    18

<210> SEQ ID NO 78
<211> LENGTH: 373
<212> TYPE: PRT
<213> ORGANISM: Artificial Sequence
<220> FEATURE:
<223> OTHER INFORMATION: variant HPPD

<400> SEQUENCE: 78

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60
```

-continued

```
Glu Ile Asn Phe Ile Ile Asn Ala Glu Pro Asp Ser Phe Ala Gln Arg
 65                  70                  75                  80

Phe Ala Arg Leu His Gly Pro Ser Val Cys Ala Ile Ala Ile Arg Val
                 85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

Lys Gly Ile Gly Asp Ser Leu Ile Tyr Phe Ile Asp Lys Trp Arg Gly
130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Val Lys Ser Lys
210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Glu Tyr
            340                 345                 350

Asn Phe Lys Gly Leu Phe Glu Thr Met Glu Leu Asp Gln Met Arg Arg
        355                 360                 365

Gly Val Leu Lys Thr
370
```

<210> SEQ ID NO 79
<211> LENGTH: 373
<212> TYPE: PRT
<213> ORGANISM: Artificial Sequence
<220> FEATURE:
<223> OTHER INFORMATION: variant HPPD

<400> SEQUENCE: 79

```
Met Asn Ala Pro Leu Thr Gln Ser Asn Ala Ser Gln Phe Gln Thr Trp
  1               5                  10                  15

Asp Asn Pro Met Gly Thr Asp Gly Phe Glu Phe Val Glu Tyr Ala Ala
             20                  25                  30

Pro Asp Pro Val Ala Met Gly Gln Leu Phe Glu Arg Met Gly Phe Gln
         35                  40                  45
```

Ala Ile Ala Lys His Arg Arg Lys Asn Val Thr Leu Tyr Arg Gln Gly
        50                  55                  60

Glu Ile Asn Phe Ile Ile Asn Ala Glu Pro Asp Ser Phe Ala Gln Arg
 65                  70                  75                  80

Phe Ala Arg Leu His Gly Pro Ser Val Cys Ala Ile Ala Ile Arg Val
                 85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
            115                 120                 125

Lys Gly Ile Gly Asp Ser Leu Ile Tyr Phe Ile Asp Lys Trp Arg Gly
130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
            195                 200                 205

Ile Arg Tyr Phe Asp Ile Glu Gly Gln Ala Thr Gly Val Lys Ser Lys
210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
            275                 280                 285

Glu Thr Tyr Tyr Glu Leu Leu Pro Lys Arg Ile Pro Asp Leu Gln Glu
290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Glu Tyr
            340                 345                 350

Asn Phe Gly Gly Leu Phe Glu Thr Met Glu Leu Asp Gln Met Arg Arg
            355                 360                 365

Gly Val Leu Lys Thr
        370

<210> SEQ ID NO 80
<211> LENGTH: 373
<212> TYPE: PRT
<213> ORGANISM: Artificial Sequence
<220> FEATURE:
<223> OTHER INFORMATION: variant HPPD

<400> SEQUENCE: 80

Met Asn Ala Pro Leu Thr Gln Ser Asn Ala Ser Gln Phe Gln Thr Trp
 1               5                  10                  15

Asp Asn Pro Met Gly Thr Asp Gly Phe Glu Phe Val Glu Tyr Ala Ala
             20                  25                  30

Pro Asp Pro Val Ala Met Gly Gln Leu Phe Glu Arg Met Gly Phe Gln
            35                  40                  45

Ala Ile Ala Lys His Arg Arg Lys Asn Val Thr Leu Tyr Arg Gln Gly
 50                  55                  60

Glu Ile Asn Phe Ile Ile Asn Ala Glu Pro Asp Ser Phe Ala Gln Arg
 65                  70                  75                  80

Phe Ala Arg Leu His Gly Pro Ser Val Cys Ala Ile Ala Ile Arg Val
                 85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
            115                 120                 125

Lys Gly Ile Gly Asp Ser Leu Ile Tyr Phe Ile Asp Lys Trp Arg Gly
            130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
            195                 200                 205

Ala Arg Tyr Phe Asp Ile Glu Gly Gln Ala Thr Gly Val Lys Ser Lys
            210                 215                 220

Ala Met Thr Ser Pro Cys Gly Lys Ile Arg Ile Pro Ile Asn Glu Glu
225                 230                 235                 240

Gly Asn Asp Lys Ala Gly His Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
            275                 280                 285

Glu Thr Tyr Tyr Glu Leu Leu Pro Lys Arg Ile Pro Asp Leu Gln Glu
            290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Tyr
            340                 345                 350

Asn Phe Lys Gly Leu Phe Glu Thr Met Glu Leu Asp Gln Met Arg Arg
            355                 360                 365

Gly Val Leu Lys Thr
            370

<210> SEQ ID NO 81
<211> LENGTH: 373
<212> TYPE: PRT
<213> ORGANISM: Artificial Sequence
<220> FEATURE:
<223> OTHER INFORMATION: variant HPPD

<400> SEQUENCE: 81

Met Asn Ala Pro Leu Thr Gln Ser Asn Ala Ser Gln Phe Gln Thr Trp
 1                  5                  10                  15

Asp Asn Pro Met Gly Thr Asp Gly Phe Glu Phe Val Glu Tyr Ala Ala
                20                  25                  30

Pro Asp Pro Val Ala Met Gly Gln Leu Phe Glu Arg Met Gly Phe Gln
         35                  40                  45

Ala Ile Ala Lys His Arg Arg Lys Asn Val Thr Leu Tyr Arg Gln Gly
 50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                 85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

Lys Gly Ile Gly Asp Ser Leu Ile Tyr Phe Ile Asp Lys Trp Arg Gly
130                 135                 140

Lys Asn Gly Ala Lys Asp Gly Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ala Arg Tyr Phe Asp Ile Glu Gly Gln Ala Thr Gly Ile Lys Ser Lys
210                 215                 220

Ala Met Thr Ser Pro Cys Gly Lys Ile Arg Ile Pro Ile Asn Glu Glu
225                 230                 235                 240

Gly Asn Asp Lys Ala Gly His Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Tyr
            340                 345                 350

Asn Phe Lys Gly Leu Phe Glu Thr Met Glu Leu Asp Gln Met Arg Arg
        355                 360                 365

Gly Val Leu Lys Thr
        370

<210> SEQ ID NO 82
<211> LENGTH: 373
<212> TYPE: PRT
<213> ORGANISM: Artificial Sequence
<220> FEATURE:
<223> OTHER INFORMATION: variant HPPD

<400> SEQUENCE: 82

```
Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
            35                  40                  45

Ala Ile Ala Lys His Arg Arg Lys Asn Val Thr Leu Tyr Arg Gln Gly
50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
            115                 120                 125

Lys Gly Ile Gly Asp Ser Leu Ile Tyr Phe Ile Asp Lys Trp Arg Gly
130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Gly Ala Glu Leu Ala Glu Phe Tyr Glu Arg Ile Phe Asn Phe Arg Glu
            195                 200                 205

Ile Arg Tyr Phe Asp Ile Glu Gly Gln Ala Thr Gly Val Lys Ser Lys
210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
            245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
            275                 280                 285

Glu Thr Tyr Tyr Glu Leu Leu Pro Lys Arg Ile Pro Asp Leu Gln Glu
            290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
            325                 330                 335

Phe Phe Glu Phe Ile Gln Arg Lys Gly Asn Ser Gly Phe Gly Pro Tyr
            340                 345                 350

Asn Phe Lys Gly Leu Phe Glu Thr Met Glu Leu Asp Gln Met Arg Arg
            355                 360                 365

Gly Val Leu Lys Thr
    370
```

<210> SEQ ID NO 83
<211> LENGTH: 373
<212> TYPE: PRT
<213> ORGANISM: Artificial Sequence
<220> FEATURE:
<223> OTHER INFORMATION: variant HPPD

<400> SEQUENCE: 83

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

Lys Gly Ile Gly Asp Ser Leu Ile Tyr Phe Ile Asp Lys Trp Arg Gly
    130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Val Lys Ser Lys
    210                 215                 220

Ala Met Thr Ser Pro Cys Gly Lys Ile Arg Ile Pro Ile Asn Glu Glu
225                 230                 235                 240

Gly Asn Asp Lys Ala Gly His Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
    290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Leu Gly Pro Ile
                325                 330                 335

Phe Phe Glu Phe Ile Gln Arg Lys Gly Asn Ser Gly Phe Gly Pro Tyr
            340                 345                 350

Asn Phe Lys Gly Leu Phe Glu Thr Met Glu Leu Asp Gln Met Arg Arg
        355                 360                 365

Gly Val Leu Lys Thr
    370

<210> SEQ ID NO 84
<211> LENGTH: 373
<212> TYPE: PRT

<213> ORGANISM: Artificial Sequence
<220> FEATURE:
<223> OTHER INFORMATION: variant HPPD

<400> SEQUENCE: 84

```
Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

Lys Gly Ile Gly Asp Ser Leu Ile Tyr Phe Ile Asp Lys Trp Arg Gly
    130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Ile Lys Ser Lys
    210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
    290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Tyr
            340                 345                 350

Asn Phe Lys Gly Leu Phe Glu Thr Met Glu Leu Asp Gln Met Arg Arg
        355                 360                 365

Gly Val Leu Lys Thr
    370
```

```
<210> SEQ ID NO 85
<211> LENGTH: 373
<212> TYPE: PRT
<213> ORGANISM: Artificial Sequence
<220> FEATURE:
<223> OTHER INFORMATION: variant HPPD

<400> SEQUENCE: 85

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

Lys Gly Ile Gly Asp Ser Leu Ile Tyr Phe Ile Asp Lys Trp Arg Gly
    130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Ile Lys Ser Lys
    210                 215                 220

Ala Met Thr Ser Pro Cys Gly Lys Ile Arg Ile Pro Ile Asn Glu Glu
225                 230                 235                 240

Gly Asn Asp Lys Ala Gly His Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
    290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Tyr
            340                 345                 350

Asn Phe Lys Gly Leu Phe Glu Thr Met Glu Leu Asp Gln Met Arg Arg
        355                 360                 365

Gly Val Leu Lys Thr
```

370

<210> SEQ ID NO 86
<211> LENGTH: 373
<212> TYPE: PRT
<213> ORGANISM: Artificial Sequence
<220> FEATURE:
<223> OTHER INFORMATION: variant HPPD

<400> SEQUENCE: 86

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
                20                  25                  30

Pro Asp Pro Val Ala Met Gly Gln Leu Phe Glu Arg Met Gly Phe Gln
            35                  40                  45

Ala Ile Ala Lys His Arg Arg Lys Asn Val Thr Leu Tyr Arg Gln Gly
        50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
                100                 105                 110

Gly Tyr Ala Gln Gln Ala Ala Pro Gly Glu Leu Ser Ile Pro Ala Ile
            115                 120                 125

Lys Gly Ile Gly Asp Ser Leu Ile Tyr Phe Ile Asp Lys Trp Arg Gly
130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ala Arg Tyr Phe Asp Ile Glu Gly Gln Ala Thr Gly Ser Lys Ser Lys
    210                 215                 220

Ala Met Thr Ser Pro Cys Gly Lys Ile Arg Ile Pro Ile Asn Glu Glu
225                 230                 235                 240

Gly Asn Asp Lys Ala Gly His Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
    290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Leu Gly Pro Ile
                325                 330                 335

Phe Phe Glu Phe Ile Gln Arg Lys Gly Asn Ser Gly Phe Gly Ala Tyr
            340                 345                 350

Asn Phe Lys Ala Leu Phe Glu Thr Met Glu Leu Asp Gln Met Arg Arg

Gly Val Leu Lys Thr
    370

<210> SEQ ID NO 87
<211> LENGTH: 373
<212> TYPE: PRT
<213> ORGANISM: Artificial Sequence
<220> FEATURE:
<223> OTHER INFORMATION: variant HPPD

<400> SEQUENCE: 87

Met Asn Ala Pro Leu Thr Gln Ser Asn Ala Ser Gln Phe Gln Thr Trp
1               5                   10                  15

Asp Asn Pro Met Gly Thr Asp Gly Phe Glu Phe Val Glu Tyr Ala Ala
            20                  25                  30

Pro Asp Pro Val Ala Met Gly Gln Leu Phe Glu Arg Met Gly Phe Gln
        35                  40                  45

Ala Ile Ala Lys His Arg Arg Lys Asn Val Thr Leu Tyr Arg Gln Gly
    50                  55                  60

Glu Ile Asn Phe Ile Ile Asn Ala Glu Pro Asp Ser Phe Ala Gln Arg
65                  70                  75                  80

Phe Ala Arg Leu His Gly Pro Ser Val Cys Ala Ile Ala Ile Arg Val
                85                  90                  95

Asn Asp Ala Lys Tyr Ala Tyr Glu Arg Ala Thr Ser Leu Gly Ala Trp
            100                 105                 110

Gly Tyr Ala Gln Gln Ala Ala Pro Gly Glu Leu Ser Ile Pro Ala Ile
        115                 120                 125

Lys Gly Ile Gly Asp Ser Leu Ile Tyr Phe Ile Asp Lys Trp Arg Gly
    130                 135                 140

Lys Asn Gly Ala Lys Asp Gly Asp Leu Gly Asn Ile Ser Phe Phe Asp
145                 150                 155                 160

Val Asp Phe Glu Pro Leu Pro Gly Ala Asp Leu His Pro Glu Gly Leu
                165                 170                 175

Gly Leu Thr Tyr Ile Asp His Leu Thr Asn Asn Val Tyr Arg Gly Arg
            180                 185                 190

Met Ala Glu Leu Ala Glu Phe Tyr Glu Arg Ile Phe Asn Phe Arg Glu
        195                 200                 205

Ile Arg Tyr Phe Asp Ile Glu Gly Gln Ala Thr Gly Val Lys Ser Lys
    210                 215                 220

Ala Met Thr Ser Pro Cys Gly Lys Ile Arg Ile Pro Ile Asn Glu Glu
225                 230                 235                 240

Gly Asn Asp Lys Ala Gly Gln Ile Gln Glu Tyr Leu Asp Met Tyr Arg
                245                 250                 255

Gly Glu Gly Ile Gln His Ile Ala Leu Gly Ser Thr Asn Leu Tyr Asp
            260                 265                 270

Thr Val Asp Gly Leu Gln Met Asn Gly Ile Lys Leu Leu Asn Thr Ser
        275                 280                 285

Glu Thr Tyr Tyr Glu Leu Leu Pro Lys Arg Ile Pro Asp Leu Gln Glu
    290                 295                 300

Pro Ile Pro Glu Leu Leu Ala Arg Asn Ile Leu Val Asp Gly Gln Pro
305                 310                 315                 320

Gly Glu Leu Leu Leu Gln Ile Phe Ser Glu Asn Gln Leu Gly Pro Ile
                325                 330                 335

Phe Phe Glu Phe Ile Gln Arg Lys Gly Asn Ser Gly Phe Gly Pro Trp

```
                    340                 345                 350
Asn Phe Ala Gln Leu Phe Glu Thr Met Glu Leu Asp Gln Met Arg Arg
                355                 360                 365
Gly Val Leu Lys Thr
            370

<210> SEQ ID NO 88
<211> LENGTH: 358
<212> TYPE: PRT
<213> ORGANISM: Artificial Sequence
<220> FEATURE:
<223> OTHER INFORMATION: variant HPPD

<400> SEQUENCE: 88

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Ala Ile Asn Leu Ile Leu Asn Asn Glu Pro His
    50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Phe
    130                 135                 140

Leu Glu Gly Val Asp Arg Asn Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Gln Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ser Arg Gly Ile Leu Leu Asp Gly Ala Ser Asp Lys Glu Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
```

|  | 325 | | | | 330 | | | | 335 | |
|---|---|---|---|---|---|---|---|---|---|---|

Asn Phe Lys Gly Leu Phe Glu Ser Ile Glu Arg Asp Gln Val Arg Arg
        340                345              350

Gly Val Leu Ala Thr Glu
        355

<210> SEQ ID NO 89
<211> LENGTH: 1473
<212> TYPE: DNA
<213> ORGANISM: Glycine max

<400> SEQUENCE: 89

| | | | | |
|---|---|---|---|---|
| atgcccatgt acactccatc actctccgca ccctcctcca atcacattca accaagtgtc | | | | 60 |
| acactcccct tatatatcac aaccaccaag ctcaatctca agcagcagca tcacaccaca | | | | 120 |
| ccaatgccaa tacccatgtg caacgaaatt caagcccaag cccaagccca agcccaagcc | | | | 180 |
| caacctgggt ttaagctcgt cggtttcaaa aacttcgtcc gaaccaatcc taagtcggac | | | | 240 |
| cgctttcaag tcaaccgctt ccaccacatc gagttctggt gcaccgatgc caccaacgcc | | | | 300 |
| tctcgccgat tctcttgggg acttggaatg cctattgtgg caaaatctga tctctccacc | | | | 360 |
| ggaaaccaaa tccacgcctc ctacctcctc cgctccggcg acctctcctt cctcttctcc | | | | 420 |
| gctccttact ctccctctct ctccgccggc tcctccgctg cctcctccgc ctccattccc | | | | 480 |
| agtttcgacg ccgccacctg ccttgccttc gctgccaaac acggcttcgg cgtccgcgcc | | | | 540 |
| atcgccttgg aagtcgccga cgcggaagcc gctttcagcg ccagcgtcgc gaaggagcc | | | | 600 |
| gagccggcgt cgccgccggt tctcgtcgac gatcgcaccg gcttcgcgga ggtgcgcctc | | | | 660 |
| tacggcgacg tggtgctccg ctacgtcagc tacaaggacg ccgcgccgca ggcgccacac | | | | 720 |
| gcagatccgt cgcggtggtt cctgccggga ttcgaggccg cggcgtcgtc gtcttcgttt | | | | 780 |
| ccggagctgg actacgggat ccggcggctg gaccacgccg tcgggaacgt tccggagctg | | | | 840 |
| gcgccggcgg tgaggtacct gaaaggcttc agcggattcc acgagttcgc ggagttcacc | | | | 900 |
| gcggaggacg tgggaacgag cgagagcggg ttgaactcgg tggttctggc gaacaactcg | | | | 960 |
| gagacggtgt tgctgccgct gaacgagccg gtttacggaa cgaagaggaa gagccagatt | | | | 1020 |
| gagacgtatt tggaacacaa cgaaggtgct ggtgtgcagc accttgcgct tgttactcac | | | | 1080 |
| gacatcttca ccacactgag agagatgaga aagcgaagtt tccttggtgg atttgagttc | | | | 1140 |
| atgccttctc ctcctcccac ctattacgcc aacctccaca ccgtgccgc tgatgtgttg | | | | 1200 |
| accgttgacc agattaagca gtgtgaggag cttgggattc ttgttgacag agatgatcag | | | | 1260 |
| ggcactctgc ttcagatttt caccaagcct gttggggaca ggccaacgat attcatagag | | | | 1320 |
| ataattcaga ggatcgggtg catggtggag gatgaggaag gaaggtgta ccagaagggt | | | | 1380 |
| gcatgtgggg gttttgggaa aggcaatttt tctgagcttt tcaaatccat tgaagaatat | | | | 1440 |
| gagaagactt tggaagctaa aagaaccgcg taa | | | | 1473 |

<210> SEQ ID NO 90
<211> LENGTH: 1266
<212> TYPE: DNA
<213> ORGANISM: Glycine max

<400> SEQUENCE: 90

| | | | | |
|---|---|---|---|---|
| atgcaggaag aggagcgtga gagaagagag tccagcaatg tccaaaccgg gtttaagctc | | | | 60 |
| gttggtttca caaacttcgt ccgaaccaac cctaaatcgg accgctttca agttaaccgc | | | | 120 |
| ttccaccaca tcggcttctg gtgcaccgat gctaccaact cttcccgccg attctcttgg | | | | 180 |

```
ggacttggaa tgcctattgt ggcaaaatcc gatctctcca ccggaaacca aatccacgcc      240
tcctacctcc tccgctccgg tgacctctcc ttcctcttct ccgctgccac cggaggcgcc      300
tccaccgcct cccttccaac cttcgacgcc gccacctgcc tcgccttcgc cgccaagcac      360
ggcttcggcg tccgtgccat cgctttggag gtagccgacg cggaagccgc cttcaacgcc      420
agcgtcgcca acggcgccga gccggcgtct ccaccggctc tcctcgacgg ccgcaccggc      480
ttcgcggagg tacgcctcta cggcgacgtc gtgctccgct acgtaagcca caaggacgcc      540
gcgccgcggg cggatccgtc gcggtggttc ctgccgggat tcgaggccgc gtcgtggtcg      600
tttccggagc tggactacgg gattcggcgg ctggaccacg ccgtcgggaa cgtgcccgaa      660
ctggcgccgg cggtcaggta cctgaaaggc ttcagcggat ccacgagtt cgcggagttc      720 accgcggagg acgtgggaac gagcgagagc gggttgaact cggtgtttct ggcgaacaac      780
tcggagacgg tgttgctggc gctgaacgag cctgtttacg gaacgaaacg gaagagccag      840
attgagactt atttggaaca caacgaaggt gctggtgtgc agcatcttgc gcttgttact      900
cacgacattt tcaccactct gagagagatg aggaagcgaa gtttccttgg tggatttgag      960
ttcacgccct tcgcctactc cacctattac gccaaccttc acaagcgtgc cggtgatgtg     1020
ttgaccacag agatgatcag ggcactctgc ttcagaggat tgggtgcatg gtggaggatg     1080
aggaagggaa ggcgtaccag aagggtgcat gtggggttt tgggaaaggc aatatttccc     1140
aacttgaaga atatgagaag actttggaag ctaaagaac tcagagtgat ctcagctctc     1200
tgcttaaaaa agttccgttg ccgggaatcg aacccgggtc cctgggtga agccagata     1260 tcctaa                                                               1266

<210> SEQ ID NO 91
<211> LENGTH: 501
<212> TYPE: DNA
<213> ORGANISM: Artificial Sequence
<220> FEATURE:
<223> OTHER INFORMATION: hppdGm-hpf1

<400> SEQUENCE: 91
ccggcggctg gaccacgccg tcgggaacgt tccggagctg gcgccggcgg tgaggtacct       60
gaaaggcttc agcggattcc acgagttcgc ggagttcacc gcggaggacg tgggaacgag      120
cgagagcggg ttgaactcgg tggttctggc gaacaactcg gagacggtgt tgctgccgct      180
gaacgagccg gtttacggaa cgaagaggaa gagccagatt gagacgtatt tggaacacaa      240
cgaaggtgct ggtgtgcagc accttgcgct tgttactcac gacatcttca ccacactgag      300
agagatgaga aagcgaagtt tccttggtgg atttgagttc atgccttctc ctcctcccac      360
ctattacgcc aacctccaca accgtgccgc tgatgtgttg accgttgacc agattaagca      420
gtgtgaggag cttgggattc ttgttgacag agatgatcag ggcactctgc ttcagatttt      480
caccaagcct gttggggaca g                                               501

<210> SEQ ID NO 92
<211> LENGTH: 490
<212> TYPE: PRT
<213> ORGANISM: Glycine max

<400> SEQUENCE: 92

Met Pro Met Tyr Thr Pro Ser Leu Ser Ala Pro Ser Ser Asn His Ile
1               5                   10                  15

Gln Pro Ser Val Thr Leu Pro Leu Tyr Ile Thr Thr Lys Leu Asn
```

```
                  20                  25                  30
Leu Lys Gln Gln His His Thr Thr Pro Met Pro Ile Pro Met Cys Asn
             35                  40                  45

Glu Ile Gln Ala Gln Ala Gln Ala Gln Ala Gln Pro Gly Phe
 50                  55                  60

Lys Leu Val Gly Phe Lys Asn Phe Val Arg Thr Asn Pro Lys Ser Asp
 65                  70                  75                  80

Arg Phe Gln Val Asn Arg Phe His His Ile Glu Phe Trp Cys Thr Asp
                 85                  90                  95

Ala Thr Asn Ala Ser Arg Arg Phe Ser Trp Gly Leu Gly Met Pro Ile
                100                 105                 110

Val Ala Lys Ser Asp Leu Ser Thr Gly Asn Gln Ile His Ala Ser Tyr
                115                 120                 125

Leu Leu Arg Ser Gly Asp Leu Ser Phe Leu Phe Ser Ala Pro Tyr Ser
                130                 135                 140

Pro Ser Leu Ser Ala Gly Ser Ser Ala Ala Ser Ser Ala Ser Ile Pro
145                 150                 155                 160

Ser Phe Asp Ala Ala Thr Cys Leu Ala Phe Ala Ala Lys His Gly Phe
                165                 170                 175

Gly Val Arg Ala Ile Ala Leu Glu Val Ala Asp Ala Glu Ala Ala Phe
                180                 185                 190

Ser Ala Ser Val Ala Lys Gly Ala Glu Pro Ala Ser Pro Pro Val Leu
                195                 200                 205

Val Asp Asp Arg Thr Gly Phe Ala Glu Val Arg Leu Tyr Gly Asp Val
                210                 215                 220

Val Leu Arg Tyr Val Ser Tyr Lys Asp Ala Ala Pro Gln Ala Pro His
225                 230                 235                 240

Ala Asp Pro Ser Arg Trp Phe Leu Pro Gly Phe Glu Ala Ala Ala Ser
                245                 250                 255

Ser Ser Ser Phe Pro Glu Leu Asp Tyr Gly Ile Arg Arg Leu Asp His
                260                 265                 270

Ala Val Gly Asn Val Pro Glu Leu Ala Pro Ala Val Arg Tyr Leu Lys
                275                 280                 285

Gly Phe Ser Gly Phe His Glu Phe Ala Glu Phe Thr Ala Glu Asp Val
                290                 295                 300

Gly Thr Ser Glu Ser Gly Leu Asn Ser Val Val Leu Ala Asn Asn Ser
305                 310                 315                 320

Glu Thr Val Leu Leu Pro Leu Asn Glu Pro Val Tyr Gly Thr Lys Arg
                325                 330                 335

Lys Ser Gln Ile Glu Thr Tyr Leu Glu His Asn Glu Gly Ala Gly Val
                340                 345                 350

Gln His Leu Ala Leu Val Thr His Asp Ile Phe Thr Thr Leu Arg Glu
                355                 360                 365

Met Arg Lys Arg Ser Phe Leu Gly Gly Phe Glu Phe Met Pro Ser Pro
                370                 375                 380

Pro Pro Thr Tyr Tyr Ala Asn Leu His Asn Arg Ala Ala Asp Val Leu
385                 390                 395                 400

Thr Val Asp Gln Ile Lys Gln Cys Glu Glu Leu Gly Ile Leu Val Asp
                405                 410                 415

Arg Asp Asp Gln Gly Thr Leu Leu Gln Ile Phe Thr Lys Pro Val Gly
                420                 425                 430

Asp Arg Pro Thr Ile Phe Ile Glu Ile Ile Gln Arg Ile Gly Cys Met
                435                 440                 445
```

```
Val Glu Asp Glu Glu Gly Lys Val Tyr Gln Lys Gly Ala Cys Gly Gly
    450                 455                 460

Phe Gly Lys Gly Asn Phe Ser Glu Leu Phe Lys Ser Ile Glu Glu Tyr
465                 470                 475                 480

Glu Lys Thr Leu Glu Ala Lys Arg Thr Ala
                485                 490

<210> SEQ ID NO 93
<211> LENGTH: 421
<212> TYPE: PRT
<213> ORGANISM: Glycine max

<400> SEQUENCE: 93

Met Gln Glu Glu Glu Arg Glu Arg Glu Ser Ser Asn Val Gln Thr
1               5                   10                  15

Gly Phe Lys Leu Val Gly Phe Thr Asn Phe Val Arg Thr Asn Pro Lys
                20                  25                  30

Ser Asp Arg Phe Gln Val Asn Arg Phe His His Ile Gly Phe Trp Cys
            35                  40                  45

Thr Asp Ala Thr Asn Ser Ser Arg Arg Phe Ser Trp Gly Leu Gly Met
50                  55                  60

Pro Ile Val Ala Lys Ser Asp Leu Ser Thr Gly Asn Gln Ile His Ala
65                  70                  75                  80

Ser Tyr Leu Leu Arg Ser Gly Asp Leu Ser Phe Leu Phe Ser Ala Ala
                85                  90                  95

Thr Gly Gly Ala Ser Thr Ala Ser Leu Pro Thr Phe Asp Ala Ala Thr
            100                 105                 110

Cys Leu Ala Phe Ala Ala Lys His Gly Phe Gly Val Arg Ala Ile Ala
        115                 120                 125

Leu Glu Val Ala Asp Ala Glu Ala Phe Asn Ala Ser Val Ala Asn
130                 135                 140

Gly Ala Glu Pro Ala Ser Pro Pro Ala Leu Leu Asp Gly Arg Thr Gly
145                 150                 155                 160

Phe Ala Glu Val Arg Leu Tyr Gly Asp Val Val Leu Arg Tyr Val Ser
                165                 170                 175

His Lys Asp Ala Ala Pro Arg Ala Asp Pro Ser Arg Trp Phe Leu Pro
            180                 185                 190

Gly Phe Glu Ala Ala Ser Trp Ser Phe Pro Glu Leu Asp Tyr Gly Ile
        195                 200                 205

Arg Arg Leu Asp His Ala Val Gly Asn Val Pro Glu Leu Ala Pro Ala
210                 215                 220

Val Arg Tyr Leu Lys Gly Phe Ser Gly Phe His Glu Phe Ala Glu Phe
225                 230                 235                 240

Thr Ala Glu Asp Val Gly Thr Ser Glu Ser Gly Leu Asn Ser Val Phe
                245                 250                 255

Leu Ala Asn Asn Ser Glu Thr Val Leu Ala Leu Asn Glu Pro Val
            260                 265                 270

Tyr Gly Thr Lys Arg Lys Ser Gln Ile Glu Thr Tyr Leu Glu His Asn
        275                 280                 285

Glu Gly Ala Gly Val Gln His Leu Ala Leu Val Thr His Asp Ile Phe
290                 295                 300

Thr Thr Leu Arg Glu Met Arg Lys Arg Ser Phe Leu Gly Gly Phe Glu
305                 310                 315                 320

Phe Thr Pro Ser Pro Thr Pro Thr Tyr Tyr Ala Asn Leu His Lys Arg
```

```
                        325                 330                 335
Ala Gly Asp Val Leu Thr Thr Glu Met Ile Arg Ala Leu Cys Phe Arg
            340                 345                 350

Gly Leu Gly Ala Trp Trp Arg Met Arg Lys Gly Arg Arg Thr Arg Arg
        355                 360                 365

Val His Val Gly Val Leu Gly Lys Ala Ile Phe Pro Asn Leu Lys Asn
    370                 375                 380

Met Arg Arg Leu Trp Lys Leu Lys Glu Leu Arg Val Ile Ser Ala Leu
385                 390                 395                 400

Cys Leu Lys Lys Phe Arg Cys Arg Glu Ser Asn Pro Gly Leu Leu Gly
                405                 410                 415

Glu Ser Gln Ile Ser
            420

<210> SEQ ID NO 94
<211> LENGTH: 459
<212> TYPE: DNA
<213> ORGANISM: Artificial Sequence
<220> FEATURE:
<223> OTHER INFORMATION: intron1 hppdGm

<400> SEQUENCE: 94
gttcttcatt ttctgcttct tttttttttg ttttttttaat ccctgctaaa caactttatt     60
ataactctca cattctatta gcctagcctt gatgactttt aatttacgtt aaactgtgct    120
ttttattctc ctactttgtt agttttttt tttatataaa attttaattt ttcaattata    180
actttcaata attaacaaat gatgtacagt atagtgttat gtcagaatgg atgtacttga    240
tgtagcagtt catcagagtg tttccctcta caaattgtac ttttgtccct ttcctgacat    300
aaagtttacg acattgaaaa aattgataga taaaagtgca atttatttat cttccgcttt    360
gaactgattg aaagtggtaa aagttagatt aacaatttga cagtgtttgt gtgttggagg    420
gtggtgatta gttaaatgtg ttttgtgttg aattgacag                           459
```